(12) United States Patent
Vahlberg et al.

(10) Patent No.: US 8,131,397 B2
(45) Date of Patent: Mar. 6, 2012

(54) IDENTIFYING ITEMS FOR RESTOCKING OF A DISPENSING DEVICE SYSTEMS AND METHODS

(75) Inventors: John Vahlberg, Mountain View, CA (US); Dan Cohen, San Francisco, CA (US); Jennifer Cartright, Loomis, CA (US); Richard Caldwell, San Francisco, CA (US); Jeff Blank, Cupertino, CA (US)

(73) Assignee: Omnicell, Inc., Mountain View, CA (US)

( * ) Notice: Subject to any disclaimer, the term of this patent is extended or adjusted under 35 U.S.C. 154(b) by 777 days.

(21) Appl. No.: 12/140,975

(22) Filed: Jun. 17, 2008

(65) Prior Publication Data
US 2008/0319580 A1    Dec. 25, 2008

Related U.S. Application Data

(60) Provisional application No. 60/991,547, filed on Nov. 30, 2007, provisional application No. 60/944,995, filed on Jun. 19, 2007.

(51) Int. Cl.
*G06F 17/00* (2006.01)
(52) U.S. Cl. ........................................ 700/236; 700/244
(58) Field of Classification Search ........................ None
See application file for complete search history.

(56) References Cited

U.S. PATENT DOCUMENTS

| | | |
|---|---|---|
| 5,139,321 A | 8/1992 | Beardsley |
| 5,190,185 A | 3/1993 | Blechl |
| 5,377,864 A | 1/1995 | Blechl et al. |
| 5,745,366 A | 4/1998 | Higham et al. |
| 5,805,455 A | 9/1998 | Lipps |
| 5,805,456 A | 9/1998 | Higham et al. |
| 5,905,653 A | 5/1999 | Higham et al. |
| 5,927,540 A | 7/1999 | Godlewski |
| 6,011,999 A | 1/2000 | Holmes |
| 6,039,467 A | 3/2000 | Holmes |
| 6,068,156 A | 5/2000 | Liff et al. |
| 6,112,502 A * | 9/2000 | Frederick et al. ............. 700/237 |
| 6,151,536 A | 11/2000 | Arnold et al. |

(Continued)

FOREIGN PATENT DOCUMENTS
WO    WO 02/03230 A1    1/2002

(Continued)

OTHER PUBLICATIONS

International Search Report and Written Opinion dated Dec. 8, 2008, corresponding to International Application No. PCT/US08/67386, filed Jun. 18, 2008, 17 pages.

(Continued)

*Primary Examiner* — Timothy Waggoner
(74) *Attorney, Agent, or Firm* — Kilpatrick Townsend & Stockton LLP

(57) ABSTRACT

Systems, methods, and devices are described related to the assignment and management of patient-specific bins. A dispensing device at a healthcare facility includes a number of bins for storage of medical supplies, with some of the bins designated as patient-specific bins allocated to be assigned to patients for storage of their medications or certain other supplies. A central server computer system, in communication with a computer of the dispensing device, may monitor and assign current and future patient-specific use of the bins for the dispensing device. The assignment and management of patient-specific bins may be performed by devices distributed through the system.

21 Claims, 49 Drawing Sheets

U.S. PATENT DOCUMENTS

| | | | |
|---|---|---|---|
| 6,170,929 | B1 | 1/2001 | Wilson et al. |
| 6,219,587 | B1 | 4/2001 | Ahlin et al. |
| 6,272,394 | B1 | 8/2001 | Lipps |
| 6,354,783 | B1 | 3/2002 | Stoy et al. |
| 6,385,505 | B1 | 5/2002 | Lipps |
| 6,435,370 | B1 | 8/2002 | Wilson |
| 6,564,121 | B1 | 5/2003 | Wallace et al. |
| 6,604,019 | B2 * | 8/2003 | Ahlin et al. .................. 700/231 |
| 6,609,047 | B1 | 8/2003 | Lipps |
| 6,611,733 | B1 | 8/2003 | De La Huerga |
| 6,636,780 | B1 | 10/2003 | Haitin et al. |
| 6,640,159 | B2 | 10/2003 | Holmes et al. |
| 6,735,945 | B1 * | 5/2004 | Hall et al. ..................... 123/565 |
| 6,760,643 | B2 | 7/2004 | Lipps |
| 6,847,861 | B2 | 1/2005 | Lunak et al. |
| 6,975,922 | B2 | 12/2005 | Duncan et al. |
| 7,080,755 | B2 * | 7/2006 | Handfield et al. ............ 700/237 |
| 7,100,792 | B2 | 9/2006 | Hunter et al. |
| 7,249,688 | B2 | 7/2007 | Hunter et al. |
| 7,348,884 | B2 | 3/2008 | Higham |
| 7,395,945 | B2 * | 7/2008 | Godlewski .................... 221/120 |
| 7,571,024 | B2 | 8/2009 | Duncan et al. |
| 7,588,167 | B2 | 9/2009 | Hunter et al. |
| 7,675,421 | B2 | 3/2010 | Higham |
| 7,728,711 | B2 | 6/2010 | Shoenfeld |
| 2001/0032035 | A1 | 10/2001 | Holmes et al. |
| 2002/0130065 | A1 | 9/2002 | Bloom |
| 2003/0055531 | A1 | 3/2003 | Liff et al. |
| 2003/0074218 | A1 | 4/2003 | Liff et al. |
| 2003/0088333 | A1 | 5/2003 | Liff et al. |
| 2003/0093295 | A1 | 5/2003 | Lilly et al. |
| 2003/0120384 | A1 | 6/2003 | Haitin et al. |
| 2004/0148055 | A1 | 7/2004 | Shoenfeld |
| 2004/0176985 | A1 | 9/2004 | Lilly et al. |
| 2006/0224736 | A1 | 10/2006 | Graziado et al. |
| 2006/0229551 | A1 | 10/2006 | Martinez et al. |
| 2007/0088461 | A1 * | 4/2007 | Haitin et al. .................. 700/241 |
| 2008/0319575 | A1 | 12/2008 | Vahlberg et al. |
| 2008/0319576 | A1 | 12/2008 | Vahlberg et al. |
| 2008/0319577 | A1 | 12/2008 | Vahlberg et al. |
| 2008/0319578 | A1 | 12/2008 | Vahlberg et al. |
| 2008/0319579 | A1 | 12/2008 | Vahlberg et al. |
| 2008/0319581 | A1 | 12/2008 | Vahlberg et al. |
| 2008/0319789 | A1 | 12/2008 | Vahlberg et al. |
| 2008/0319790 | A1 | 12/2008 | Vahlberg et al. |
| 2010/0042437 | A1 | 2/2010 | Levy et al. |

FOREIGN PATENT DOCUMENTS

| | | |
|---|---|---|
| WO | WO 03/081378 A2 | 10/2003 |
| WO | WO 03/105057 A1 | 12/2003 |
| WO | WO 2007/035185 A2 | 3/2007 |

OTHER PUBLICATIONS

McKesson Connect-RN, "Empower Nurses to Optimize Medication Administration", 2005, 2 pages.

McKesson: Empowering Healthcare, "McKesson's Connect-RN Integrates IT and Automation to Ensure Patient Safety and Enhance Nursing Efficiency", Newsroom Release (Business Wire), Mar. 22, 2007, 1 page.

PCT International Search Report and Written Opinion mailed Sep. 7, 2010; International Application No. PCT/US2010/041834, 10 pages.

U.S. Appl. No. 12/140,964, filed Jun. 17, 2008, Office Action mailed Jan. 5, 2011, 12 pages.

U.S. Appl. No. 12/140,970, filed Jun. 17, 2008, Office Action mailed Feb. 16, 2011, 10 pages.

U.S. Appl. No. 12/140,966, filed Jun. 17, 2008, Office Action mailed Mar. 7, 2011, 6 pages.

Search Report and Written Opinion for Singapore Patent Application No. 200908458-3, mailed Jan. 21, 2011, 20 pages.

U.S. Appl. No. 12/140,969, filed Jun. 14, 2008, Office Action mailed Sep. 14, 2010, 12 pages.

European Search Report for Application No. EP 08771396, mailed May 12, 2011, 11 pages.

* cited by examiner

| Bin Type | Bin Storage Space | Bin Security | Bin Location in Cabinet | Med Types Stored | Med Amount | Med Security | Capacity Utilization |
|---|---|---|---|---|---|---|---|
| Bin 4, 6-Bin Sensing | X cm³ | 0 | Zone 1, Drawer 2 | Med 1 | 10 | L1 | M1% |
| Bin 5, 6-Bin Sensing | X cm³ | 0 | Zone 1, Drawer 2 | Med 2 | 12 | L1 | M2% |
| | | | | Med 3 | 3 | L1 | M3% |
| Bin 8, 12-bin Locking | Y cm³ | 2 | Zone 1, Drawer 4 | Med 4 | 23 | L2 | M4% |
| | | | | Med 5 | 14 | L3 | M5% |

IDENTIFYING ITEMS FOR RESTOCKING OF A DISPENSING DEVICE SYSTEMS AND METHODS

CROSS-REFERENCE

This application claims priority from the following U.S. Provisional patent applications: U.S. Patent Application No. 60/944,995, filed on Jun. 19, 2007, entitled "PATIENT-SPECIFIC BINS", and U.S. Patent Application No. 60/991,547, filed on Nov. 30, 2007, entitled "PATIENT-SPECIFIC BIN SYSTEMS, METHODS, AND DEVICES". This application is related to the following U.S. patent applications: U.S. patent application Ser. No. 12/140,964, filed concurrently herewith, entitled "PATIENT-SPECIFIC BIN SYSTEMS, METHODS, AND DEVICES", U.S. patent application Ser. No. 12/140,966, filed concurrently herewith, entitled "STATUS DESIGNATION FOR DISPENSING DEVICE SYSTEMS AND METHODS", U.S. patent application Ser. No. 12/140,969, filed concurrently herewith, entitled "PATIENT-SPECIFIC BIN ASSIGNMENT SYSTEMS, METHODS, AND DEVICES", U.S. patent application Ser. No. 12/140,970, filed concurrently herewith, entitled "MANAGEMENT OF PATENT TRANSFER SYSTEMS, METHODS, AND DEVICES"; U.S. patent application Ser. No. 12/140,971, filed concurrently herewith, entitled "REMOVAL OR RETURN OF ITEMS ASSOCIATED WITH A PATIENT-SPECIFIC BIN SYSTEMS AND METHODS", U.S. patent application Ser. No. 12/140,979, filed concurrently herewith, entitled "BIN ALLOCATION SYSTEMS, METHODS, AND DEVICES", U.S. patent application Ser. No. 12/140,983 now U.S. Pat. No. 8,027,749, filed concurrently herewith, entitled "HANDLING OF PATIENT'S OWN MEDICINE SYSTEMS, METHODS, AND DEVICES", and U.S. patent application Ser. No. 12/140,985 now U.S. Pat. No. 8,073,563, filed concurrently herewith, entitled "HANDLING OF MULTI-USE ITEM SYSTEMS, METHODS, AND DEVICES". This application hereby incorporates by reference herein the content of the aforementioned applications in their entirety and for all purposes.

BACKGROUND

The present invention in general relates to managing the storage and distribution of medications and other medical supplies at a healthcare facility and, in particular, to patient-specific bins.

At many healthcare facilities, it may be beneficial for items to be available for use at specific locations. For example, in hospitals, practitioners may find it convenient to place medications (including pharmaceuticals) and other supply items near where patients are being treated. A nursing station is one such location, as nurses may find it more efficient to have certain medications readily available. Depending on the type of items to be dispensed, the environment where the items are to be used, and the like, a variety of dispensing cabinets have been employed.

Typically, medications are placed in dispensing units which each store a specific item to be used for a number of different patients. However, this type of storage configuration often leads to storage of supplies at multiple locations, which may give rise to delivery inefficiencies. This item-specific storage and distribution model may also give rise to billing discrepancies and inventory control challenges. It would therefore be beneficial to create systems, methods, or devices which address one or more of the issues raised above, while still providing for distributed storage of medications.

SUMMARY

Systems, methods, and devices are described for the storage and distribution of medications and other supplies at a healthcare facility. A dispensing device (e.g., a cabinet) at the facility includes a number of bins for storage of medications and other supplies, and some of the bins may be allocated as patient-specific bins available to be assigned for patient-specific storage and dispensing functions.

A central server computer system, in communication with a computer of the dispensing device, may assign and monitor current and future patient-specific use of the bins for the dispensing device. Both the stocking and removal of items from patient-specific bins may be managed by the central server computer system. The central server computer system may also manage the handling of medications and bin assignments during the transfer or discharge of a patient. Management of multi-use items and items brought to the healthcare facility by the patient is provided for, as well.

A central dispensing unit, such as a pharmacy, may be in communication with the central server computer system and dispensing device computer to stock or restock the dispensing device at the appropriate levels. In some embodiments, the assignment and management of patient-specific bins may be performed by devices (e.g., the dispensing device) distributed through the system.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 24 is a diagram of a table of bin configuration data that may be stored, analyzed, and transmitted according to various embodiments of the invention.

DETAILED DESCRIPTION

Systems, methods, and devices are described for storing and distributing medications from a dispensing device which includes patient-specific bins. A dispensing device, such as a cabinet, includes a number of bins for storing and dispensing medications. Some of the bins are allocated to be assigned to a patient for exclusive use by the patient, and these bins may be referred to herein as patient-specific bins. In contrast, item-specific bins of the dispensing device are bins allocated for storage of one or more units of a medication independent of a relationship to a particular patient. The medication stored in such bins may be available for use by a number of patients.

The following description provides example embodiments only, and is not intended to limit the scope, applicability, or configuration of the invention. Rather, the ensuing description of the embodiments will provide those skilled in the art with an enabling description for implementing embodiments of the invention. Various changes may be made in the function and arrangement of elements without departing from the spirit and scope of the invention as set forth in the appended claims.

Thus, various embodiments may omit, substitute, or add various procedures or components as appropriate. For instance, it should be appreciated that in alternative embodiments, the methods may be performed in an order different than that described, and that various steps may be added, omitted, or combined. Also, features described with respect to certain embodiments may be combined in various other embodiments. Different aspects and elements of the embodiments may be combined in a similar manner.

It should also be appreciated that any of the following systems, methods, devices, and software may be a component of a larger system, wherein other procedures may take precedence over or otherwise modify their application. Also, a number of steps may be required before, after, or concurrently with the following embodiments.

Figure 1A:
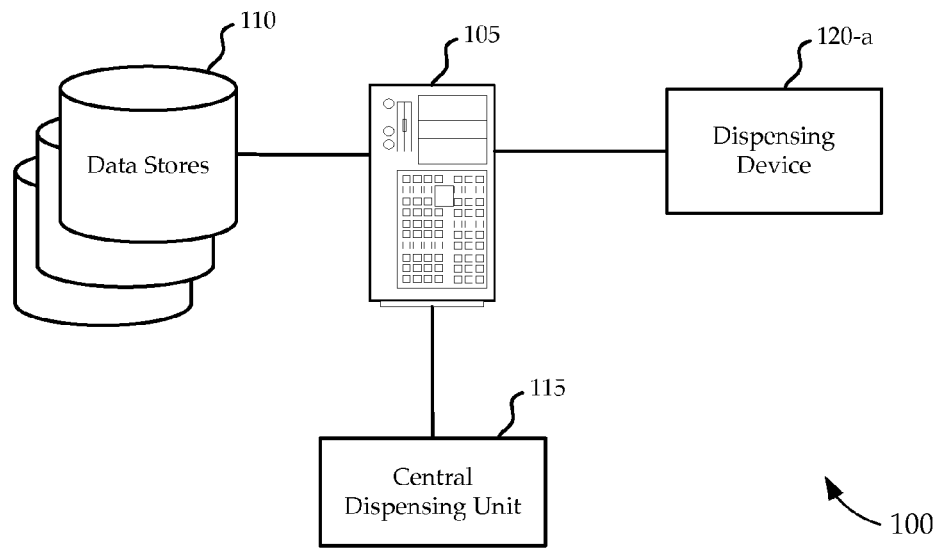
FIGS. 1A-1B are block diagrams illustrating various medical supply storage and distribution systems including patient-specific bins configured according to various embodiments of the present invention.

Referring to FIG. 1A, an example of a system 100 is illustrated for storing and distributing medical supplies from a dispensing device which includes PSBs. The system 100 includes a dispensing device 120-*a* (e.g., a cabinet with a number of bins) for dispensing medical supplies. As used herein, medical supplies include pharmaceuticals, other medications, or other supplies provided for care or service of a patient at a healthcare facility. The system also includes a central server computer system 105, which is communicatively connected with data stores 110, a central dispensing unit 115, and the dispensing device 120-*a*. In some embodiments, one or more of these components may be removed or substituted with other devices.

In one embodiment, the dispensing device 120-*a* includes one or more patient-specific bins (PSBs) and one or more item-specific bins (ISBs). PSBs are assigned to a patient for exclusive use during a determined, or undetermined, period of time. A PSB may be used for the storage and distribution of medications and other medical supplies for the assigned patient. An ISB is a bin which is assigned to an item independent of the item's relation to a patient (e.g., it may be for use among two or more patients). A "dispensing device" may be any cabinet or other device for dispensing medications or other medical supplies to patients in a healthcare facility. In other embodiments, aspects of the system may be used in different settings to dispense a range of other items. A "dispensing device" may be stationary, such as a nursing cabinet serving a particular area of a hospital, or may be mobile. The dispensing device 120-*a* may be in wired or wireless communication with the central server computer system 105.

A "bin" may be any container, mechanism, location, or zone in a dispensing device 120-*a* or unit therein, including locations in locking and sensing drawers. A "bin" may, for example, include a set of storage locations within a drawer or area of a cabinet. Other types of bins include dispensers, shelves, racks, and so on. In one embodiment, only a subset of the bins in a given dispensing device may be designated as available for PSBs. In another embodiment, the bins available for assignment as PSBs may be variable depending, for example, on the existing or future assignments of bins to PSBs or ISBs in a given cabinet.

The dispensing device 120-*a* may be located at a nursing station serving a number of rooms, at an operating room, at an emergency room, at an intensive care unit, or at a number of other locations as evident to those skilled in the art. The dispensing device 120-*a* may be mobile as well. The dispensing device 120-*a* may include a computer and console configured to manage the storage and distribution of medical supplies at the dispensing device, and networked to communicate with the central server computer system 105. There may be different levels of security for particular bins within the bins of a given dispensing device 120-*a*.

The dispensing device 120-*a* may be made up of one or more dispensing mechanisms that are secured within the device 120-*a*, with the mechanisms configured to dispense items from associated bins. Thus, mechanisms may be used to give access to the bins to only authorized individuals. A dispensing mechanism may be configured with connections to a variety of bins that each hold items to be dispensed. Such an arrangement may be well suited for items that need to be secured, such as medications, drugs, and the like. If a user is authorized, such items may be dispensed from the dispensing device 120-*a* using the mechanism, where they may fall into a dispense drawer that may be pulled to access the dispensing items. Depending on the particular configuration, one or more bins of a dispensing mechanism may be assigned as a PSB or ISB.

A dispensing device 120-*a* may include a dispenser frame with reconfigurable dividers. In this way, a wide variety of bin and dispensing mechanism arrangements may be provided by reconfiguring the dividers and/or the location of the dispensing mechanisms on the dividers. Further, various types of dispensing mechanisms may be accommodated. As noted above, one or more bins and associated mechanisms may be assigned as a PSB or ISB.

Various sensing or detecting systems may be used to determine the configuration of the dividers and the addresses of the bins and dispensing mechanisms on the dividers so that the dispensing device 120-*a* computer (and central server computer system 105) may associate one or more items with particular bins. For example, when reconfiguring locations, a sensing mechanism, such as a button, may be pressed on the dispensing mechanism to indicate the new location of the dispensing mechanism.

The patient dispensing device 120-*a* is communicatively connected (perhaps over a network) with a central server computer system 105. The communication may be wired, wireless, or a combination thereof. The central server computer system 105 may include, for example, one or more server computers, personal computers, workstations, web servers, or other suitable computing devices. The central server computer system 105 may be configured to communicate with the dispensing device 120-a, and perform and monitor the patient and bin assignments. The central server computer system 105 may allocate bins as ISBs or PSBs, and may either assign a patient to a bin or set of bins (e.g., making an assignment of a patient to a bin upon check-in or transfer) or receive patient assignment information (e.g., from the dispensing device 120-a computer). The central server computer system 105 may identify items to be stocked, restocked, or removed from a bin and transmit this information, and/or receive identification of items which are or will be stocked, restocked, or removed (e.g., from the dispensing device 120-a computer).

The central server computer system 105 may also manage at least part of the transfer or discharge of a patient, modifying patient bin assignments as appropriate. The central server computer system 105 may identify the locations (e.g., return to bin, return to pharmacy, return to patient) for items to be destocked or otherwise removed with patient transfer or discharge. The central server computer system 105 may also be configured to manage the cleanup or other removal of items from PSBs or ISBs independent of any patient transfer or discharge.

The central server computer system 105 may be configured to track inventory of medical supplies at the central dispensing unit 115 and the dispensing device 120-a. The central server computer system 105 may be configured to consolidate and filter data received from the dispensing devices 120 at one or more healthcare facilities, and produce and/or transmit audit or action reports based thereon. Using received data, the central server computer system 105 may be configured to generate restocking lists.

When a stocking or restocking list is generated (e.g., by a central server computer system 105, or perhaps by the patient dispensing device 120-a), the dispensing device 120-a (or other computing device) may receive the list. To initially stock a bin or set of bins in the dispensing device 120-a, a sensing mechanism, such as a button, may be pushed to identify the location. The type and quantity of the item stocked may then be entered into the computer associated with the dispensing device 120-a. By pressing the button, the computer may detect the bin or set of bins being accessed and the item assigned to that address. A count may be verified, the bin or set of bins restocked, and the quantity entered (and perhaps transmitted to the central server computer system 105). In some embodiments, the central server computer system 105 or the patient dispensing device 120-a computer may automatically direct the user to the PSB for the item to be stocked.

To restock, a restock list may be generated. The dispensing device 120-a computer may be coupled to a network to permit various restock information to be downloaded to the computer (e.g., from the central server computer system 105). Alternatively, the computer on the dispensing device 120-a may locally generate the list. This information may be stored at the computer, or else accessed when needed over the network. Visual indicators, such as lights, LEDs, or the like, on the dispensing locations that are to be restocked may then be actuated to guide the restock user or pharmacist through the restocking process. The button on the dispensing mechanism may be pushed to identify the dispensing mechanism that is being restocked, and the expected quantity may be displayed on the display screen. A count may be verified, the dispensing mechanism restocked, and the quantity entered (and perhaps transmitted to the central server computer system 105). In some embodiments, the central server computer system 105 or the patient dispensing device 120-a computer may automatically direct the user to the PSB for the item to be restocked.

In one embodiment, the central server computer system 105 is communicatively connected (perhaps over a network) to a set of data stores 110 stored in local or remote memory. The data stores 110 may be one, or more, relational databases or components of relational databases (e.g., tables), object databases or components of object databases, spreadsheets, text files, internal software lists, or any other type of data structure suitable for storing data. Thus, it should be appreciated that data stores 110 may each be multiple data storages (of the same or different type), or may share a common data storage with other data stores. The central server computer system 105 may query the data stores 110 for information to produce any of the output described above. The data stores 110 may store information on which bins in each of any number of dispensing devices are available to be allocated as PSBs and which bins are presently allocated as PSBs or ISBs, and may also list characteristics (type, size, location, security, etc.) of each bin. The data stores 110 may also store information on the patient assignments for such bins.

The data stores 110 may also store information on which dispensing devices are associated with a room or area of the healthcare facility. The data stores 110 may store status information on particular assigned PSBs (e.g., identifying whether a dispensing device 120-a is an active cabinet, an interim or otherwise temporary cabinet, or an inactive cabinet).

The data stores 110 may store information regarding particular patients, and the particular medication orders and other supplies currently prescribed for the patient. The data stores 110 may store information on the past, current, or future associations between a patient, his or her past, active, or future medication orders, and his or her assigned room and PSBs (e.g., identifying inventory of medical supplies for the patient at a PSB). In one embodiment, an "active medication order" is a medication order that has a start date/time that occurs in the past and a stop date/time that occurs in the future (or is indefinite in time); a "future medication order" is a medication order that has a start date/time that occurs in the future and a stop date/time that occurs in the future (or is indefinite in time); a "discontinued medication order" is a medication order that is neither active nor future and, thus, is inactive and/or has a stop date that occurs in the past. As used herein, the term "medication order" may be an order associated with one, or more, medications. Thus, a number of medication orders may be analyzed for a particular patient at a given time at a device 120, or a single medication order may be analyzed including a number of medications. Thus, it may be assumed that a reference herein to a "medication order" may be an order associated with a number of medications, or to a number of orders each associated with one or more medications.

In one embodiment, the central server computer system 105 is communicatively connected (perhaps over a network) to one or more central dispensing units 115. A central dispensing unit 115 may, for example, be a pharmacy storage and retrieval system which has a number of automated aspects. Thus, a central dispensing unit 115 may receive stocking or restocking information from the central server computer system 105 (or, perhaps from a computer on the patient dispensing device 120), and dispense the medications specified in an automated or partially automated fashion for cart-fills, or for cart-less or other environments. The computer system associated with the central dispensing unit 115 may be independent from the central server computer system, or there may be various levels of integration. The central dispensing unit 115 may be any automated packaging distribution device, controlled substance distribution device, automated medication dispensing device, or other device or mechanism that distributes medications or other supplies to patient dispensing devices 120. Thus, the central dispensing unit 115 may be a centralized medication distributor located in a healthcare facility pharmacy. In one embodiment, the central dispensing unit 115 may be a local or remote computing device configured to identify and track the dispensation of medication.

Figure 1B:
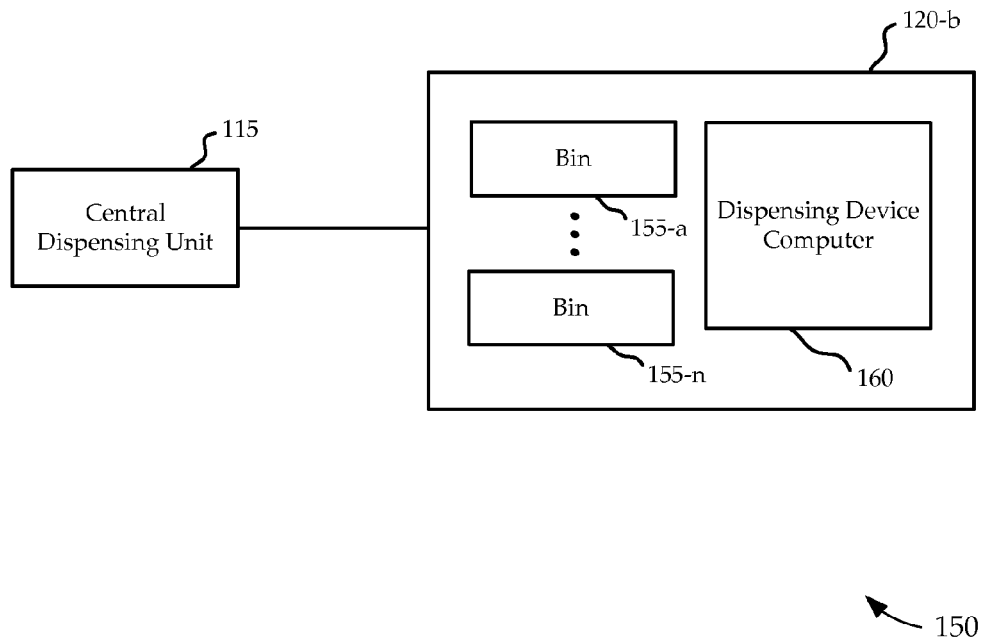

Referring next to FIG. 1B, an example of an alternative system 150 is illustrated for storing and distributing medical supplies from a dispensing device which includes PSBs. The system 150 includes a dispensing device 120-b for dispensing medical supplies (e.g., pharmaceuticals or other medications). The dispensing device 120-b of FIG. 1B may be implemented to include the functions of the patient dispensing device 120-a described with reference to FIG. 1A, and thus in one embodiment may be implemented in the system of FIG. 1A.

The dispensing device 120-b, which may, for example, be configured as a cabinet, includes a number of bins 155 for dispensing medical supplies to patients. One or more of the bins 155, or a subpart of such a bin 155, may be allocated for use as a PSB and assigned to a patient. The dispensing device 120-b also includes a computer 160. The dispensing device computer 160 may be configured to complete any of the functions (or any subset thereof) that may be performed by the central server computer system 105 of FIG. 1. Therefore, functions described above to be performed by the central server computer system 105 of FIG. 1 may be performed, in whole or in part, by a computer 160 local to a dispensing device 120-b. In this way, all or part of a system may be configured to operate in a centralized, or more distributed manner.

By way of example, the dispensing device computer 160 may be configured to allocate bins as ISBs or PSBs, and may either assign a patient to a bin or set of bins 155 or receive patient assignment information. The dispensing device computer 160 may also manage at least part of the transfer or discharge of a patient, modifying patient bin assignments as appropriate. The dispensing device computer 160 may also manage and direct the cleaning or other removal of items from a device 120-b independently from the transfer or discharge process. The dispensing device computer 160 may identify the locations for items to be removed (e.g., return bin, return to pharmacy, return to patient) with patient transfer, discharge, or other triggering event. The dispensing device computer 160 may be configured to track inventory of medical supplies. The dispensing device computer 160 may transmit information on its actions to the central server computer system 105.

Similarly, the dispensing device computer 160 may include memory which may store any of the information that is stored in the data stores 110 of FIG. 1A. The memory of the dispensing device computer 160 may include information limited to the associated dispensing device 120-b, or it may include information on other patient dispensing devices (e.g., covering an area making up a subset of an entire facility).

The system 150 may also include a central dispensing unit 115 communicatively connected to the patient dispensing device 120-b, perhaps over a network. The central dispensing unit 115 could receive stocking or restocking information from the patient dispensing device 120-b, and dispense the medications specified in an automated or partially automated fashion for cart-fills, or for cart-less or other environments.

Figure 2:
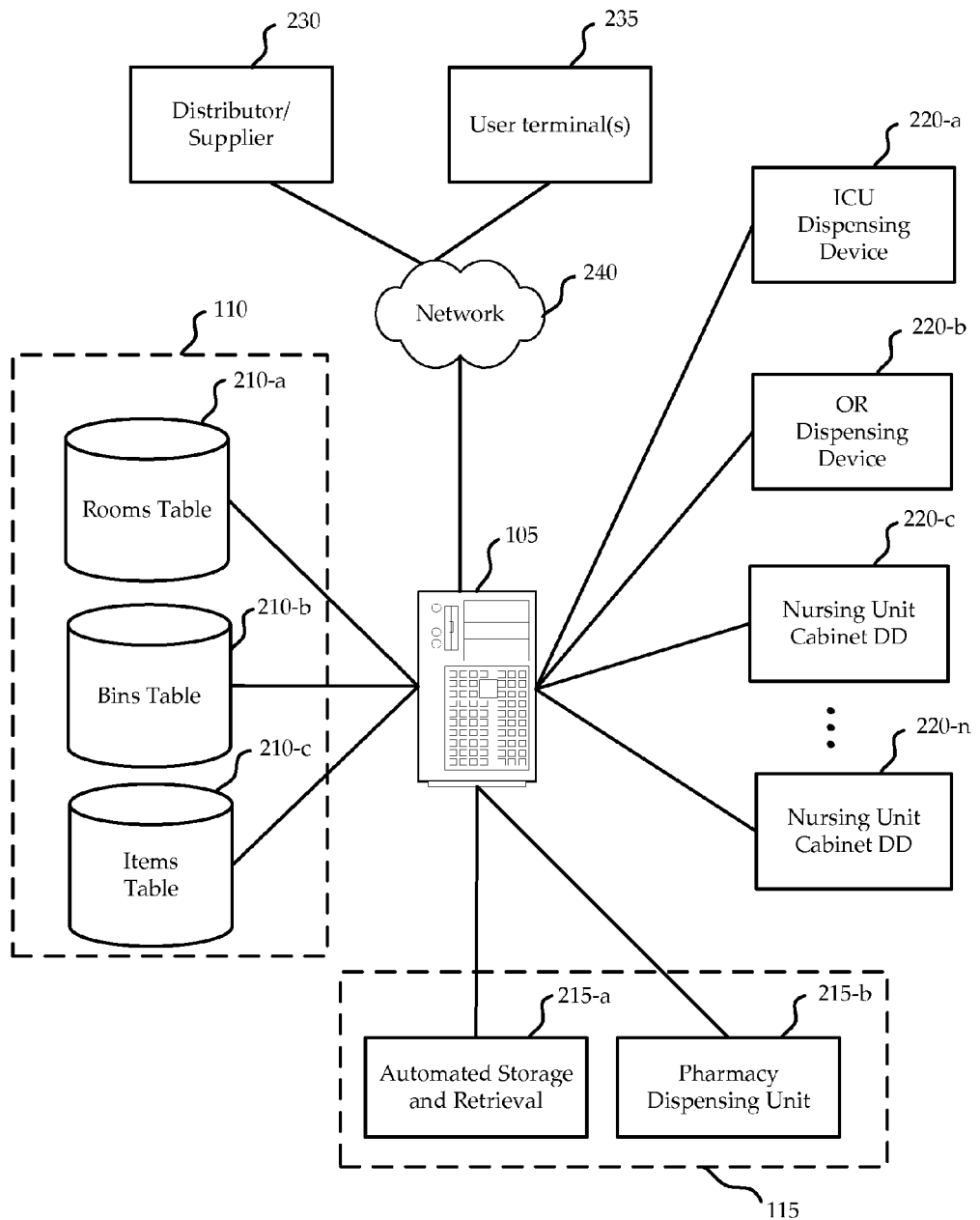
FIG. 2 is a block diagram illustrating an alternative medical supply storage and distribution system with patient-specific bins configured according to various embodiments of the present invention.

Turning next to FIG. 2, a block diagram shows a system 200 for storing and distributing medications and other supplies from dispensing devices which include PSBs. The system 200 of FIG. 2 illustrates one embodiment of the system 100 described with reference to FIG. 1A. The system 200 of FIG. 2 includes a number of patient dispensing devices 220, including an intensive care device ("ICU") dispensing device 220-a, an operating room ("OR") dispensing device 220-b, and a number of nursing unit cabinet dispensing devices 220-c to 220-n (which may be referred to hereinafter as nursing unit cabinets). These may also be mobile dispensing devices, such as carts (not shown). PSBs in a mobile dispensing device may serve to store and deliver medications to the PSBs for the patient at a stationary device (e.g., via a cart-fill or during a patient transfer). These patient dispensing devices 220 may be generally configured as described for the dispensing devices 120 of FIG. 1A or 1B. Dispensing devices 220 may include only PSBs, only ISBs, or a combination of PSBs and ISBs. Also, a dispensing device 220 may be made up of a number of distinct physical cabinets logically linked together in a room, area, or healthcare facility.

The system 200 of FIG. 2 also includes a central server computer system 105, which is communicatively connected to each of the dispensing devices 220. The central server computer system 105 of FIG. 2 may perform any of the functions described with reference to FIG. 1A, for each of the dispensing devices 220. The system 200 of FIG. 2 also includes a central dispensing unit 115, which in this embodiment is located in the healthcare facility pharmacy and is communicatively connected to the central server computer system 105. The central dispensing unit 115 includes an automated storage and retrieval device 215-a and an additional pharmacy dispensing unit 215-b.

The central server computer system 105 may generate audit reports with information received from one or more of the dispensing devices 220, and may also generate stocking or restocking lists to be transmitted to and filled at the central dispensing unit 115. The central server computer system 105 may use the received information to efficiently allocate stocking and restocking across different carts (which may each serve one or more dispensing devices 220, and run at different intervals). The audit functions and list generation may also be performed by the computer associated with a particular dispensing device 220.

In this embodiment, the central server computer system 105 is communicatively connected (perhaps over a network) to data stores 110 stored in local or remote memory. The data stores 110 may include a rooms table 210-a, which identifies rooms (or other areas) in the healthcare facility, and identifies the dispensing device or devices 220 associated with each room (or associated with an area in which the room is located). Typically, a dispensing device 220 may be associated with a number of rooms, which may be illustrated in the rooms table 210-a. There may also be a primary association and one or more secondary associations. The rooms table 210-a may also include a listing of the patient associated with the room, and may indicate any PSBs associated or assigned to the room and/or patient.

The data stores 110 may also include a bins table 210-b, which includes a listing of which bins may be allocated for patient assignment. The bins table 210-b may, thus, include information on which bins in each of any number of dispensing devices 220 are available to be allocated as PSBs and which bins are presently allocated as PSBs or ISBs, and may also list characteristics (type, size, location, control level, security, etc.) of each bin. The bins table 210-b may also store information on the particular patients assigned to each such bin (e.g., listing the patient assigned to the bin as well as any other bins to which the patient is assigned).

In one embodiment, when a bin at a dispensing device is allocated for use as a PSB, it may also be associated with an item group. There may be a range of different item groups for each healthcare facility. Each item group may be defined as including a set of items of a certain class (e.g., respiratory, refrigerated, ambulance, etc.). Information about the item group or groups associated with a PSB may be stored in the bins table 210-b, as well. Only items belonging to the matching group(s) will be allowed to be stored in the PSB. A number of different item groups may be defined (e.g., in another table in data stores 110 associating each group with a one or more different items). One item group may be a default or "general" group, including all items not associated with other groups. Each item at a healthcare facility may be associated with a group.

In one embodiment, a user will be granted access to a set of one or more item groups. When a user attempts to access a PSB, group access will be enforced in addition to control level access. For some item groups, there may be no user access restrictions. A dispensing device 120 or central server computer system 105 may enforce the PSB group designation rules such that all PSBs in the same physical access area have the same group designation.

Therefore, the bins table 210-b may associate a bin with different storage and access restrictions. A first type of storage and access restriction may be related to Drug Enforcement Agency drug classifications, limiting the type (control level) of medications that may be stored in certain bins, and limiting access to those bins to only certain users. A second type of storage and access restriction may be related to the item group associated with the bin. The healthcare facility or other entity may establish rules limiting the type of medications that may be stored in bins associated with each item group, and limiting access to those bins to certain users (e.g., only those users granted access to bins of those groups). For a PSB associated with each type of storage and access restriction, a user would have to have control level and item group access to be granted access.

The data stores 110 may also include an items table 210-c. The items table 210-c may be configured to store information and track which items are assigned to which bins. The items table 210-c may include information on the inventory level, the control level, the item group, and on whether the item is under an active or future medication order. The items table 210-c may include information regarding whether the bin is a PSB or an ISB, and on whether the bin is assigned to a patient (and perhaps identify the assigned patient).

The data stores 110 may store consolidated information on the current associations between a patient, his or her past, active, or future medication orders, and his or her past, present, or future assigned room(s) and PSBs. It is also worth noting that the data stores 110 may store status information on particular assigned PSBs (e.g., identifying whether a dispensing device 120-a is an active cabinet, an interim or otherwise temporary cabinet, or an inactive cabinet). The data stores 110 may also store information identifying each user's item group access privileges and control level access privileges.

In one embodiment, the central server computer system 105 is communicatively connected via a network 240 to a distributor/supplier 230. The central server computer system 105 (or a particular dispensing unit 220) may access the data stores 110 and the central dispensing unit 115 to determine inventory levels and active and future orders for certain supplies, and communicate order levels to the distributor/supplier 230 so that certain inventory levels are maintained. One or more user terminals 235 may program or administer the system, and order or request audit or restocking reports.

Figure 3:
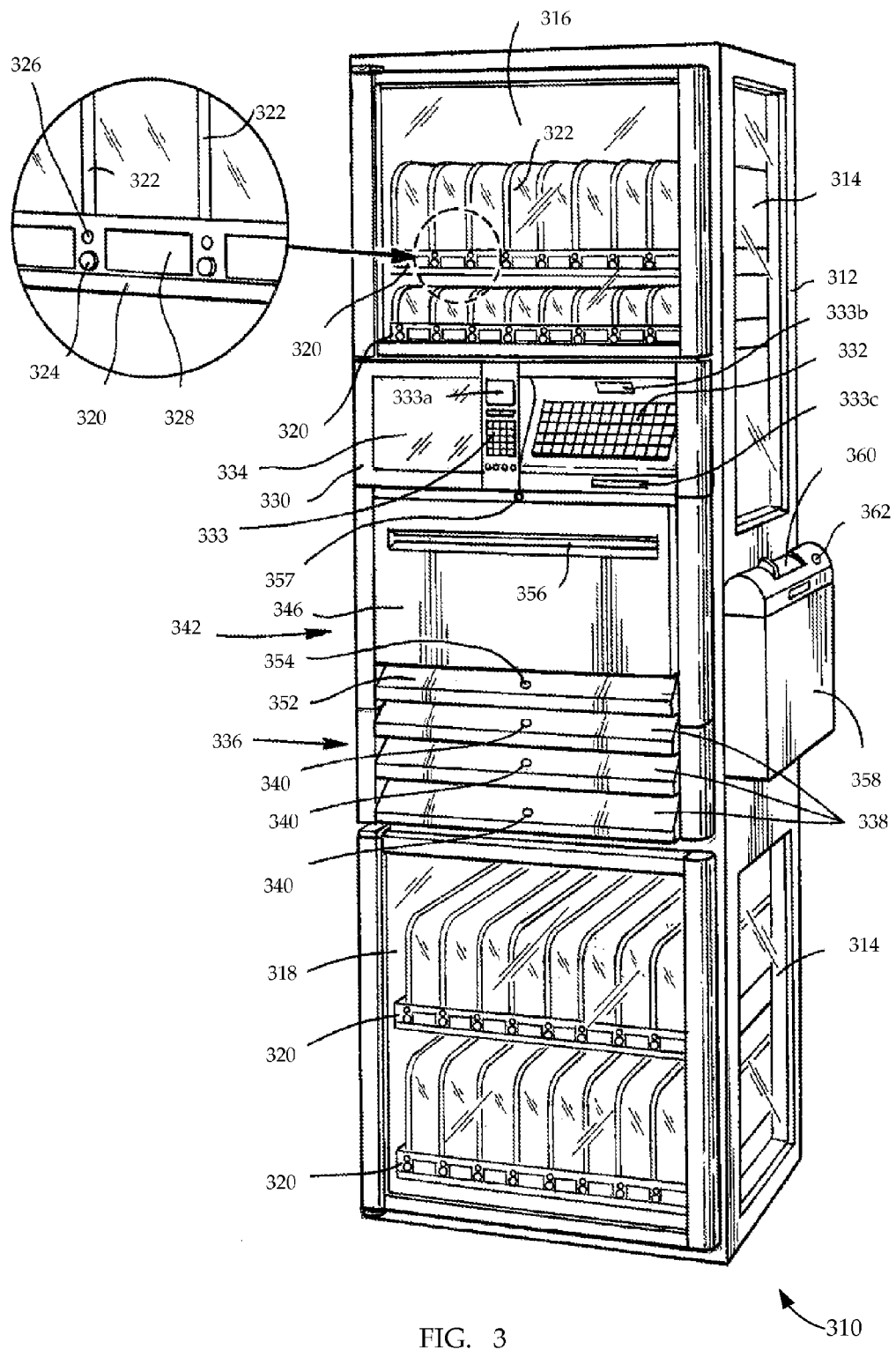
FIG. 3 illustrates a front perspective of a cabinet dispensing device according to various embodiments of the invention.

One example of a patient dispensing device 120 is illustrated in FIG. 3. The patient dispensing device in this embodiment is a cabinet 310, which may be constructed from a cabinet frame 312 with various transparent panels 314. Cabinet 310 further includes a pair of doors 316 and 318 that enclose a series of shelves 320 within the cabinet 310. These enclosed areas may be temperature-controlled or refrigerated in various embodiments. Shelves 320 may be divided into various storage locations using adjustable dividers 322. Further, associated with each storage location may be an item button 324 that may be pressed to record the removal of items from or placement of items into each storage location. A light 326 may also be positioned adjacent each item button to guide the user to a specific storage location. Further, a label 328 may be associated with each storage location and may include information on the items stored in a particular storage location. Optionally, doors 316 and 318 may be locked and only opened when appropriate identification information has been entered into a computer 330. Hence, to remove an item from one of the shelves 320, a user (e.g., a nurse user or other caregiver user) may enter appropriate identification information into computer 330. In other embodiments, the storage locations or zones could vary in size, configuration, and security. The locations may be allocated for assignment to patients as PSBs, and the locations available may be adjusted depending on current and projected use levels and occupancy factors. PSB allocation and patient bin assignment may be made by the computer 330, or received from a remote location (e.g., central server computer system 105 of FIG. 1A).

To facilitate the entry of information, the computer 330 may include a traditional keyboard 332 and a key pad 333 containing numeric keys. A touch pad 333a may be disposed above key pad 333 and used to control a pointer on a display screen 334. Disposed below key pad 333 are keys to control the contrast of display screen 334 and to control the sound that may be emitted from a speaker 333b. Disposed below keyboard 332 is a receipt port 333c through which printed receipts or labels may pass. The panel containing keyboard 332 may be rotated downward to gain access to the receipt printer. The illustrated computer configuration is for purposes of example only; in other embodiments, any subset of the features may be employed, and particular implementations and input devices may vary.

One use of the various input devices on the computer 330 is to permit the user to select one or more items that are to be removed. A list of items, generated by the computer 330 or received from the central server computer system 105, may be displayed on the display screen 334. Further, display screen 334 may be a touch screen display that permits various items to be selected simply by touching them on a display screen 334. Computer 330 may be coupled to any type of computer network to permit various information to be supplied to computer 330 (e.g., by the central server computer system 105 of FIG. 1A). For example, stock or restock lists may be transmitted from the central server computer system 105, as may lists for cleaning or other removal of items.

When the appropriate items have been selected, doors 316 and 318 may be unlocked (in cases where doors 316 and 318 are already locked) and the appropriate lights 326 may be lighted to guide the user to the items selected. Upon removal of the items, the user may press item buttons 324 a number of times corresponding to the number of items removed. A similar process may be used for restocking items into the storage locations.

A cabinet 310 may further include a pharmacy section 336 with various drawers 338 for holding pharmaceutical items or other types of items that need additional security. When appropriate information has been entered into computer 330, the appropriate drawers 338 may be unlocked and lights 340 on the drawers lighted to guide the user to the appropriate doors. Drawers 338 may conveniently include various bins (e.g., allocated as PSBs or ISBs) which may optionally have lockable lids to provide additional security to the items. The lids corresponding to bins that have the selected items may be unlocked and users may be guided to the unlocked bins using lights in a manner similar to that described with shelves 320.

In one embodiment, pharmacy section 336 further includes a dispensing unit area 342. Briefly, dispensing unit area 342 includes a dispensing unit frame that is insertable into cabinet frame 312 of cabinet 310. Coupled to the dispensing unit frame is a door 346 that may be opened to provide access to dispenser frame. Although dispensing mechanisms may typically be associated with items for use by a number of patients, particular bins associated with dispensing mechanisms may be assigned to patients in some embodiments. Below dispenser frame is a dispense drawer 352 that receives items that fall from dispensing mechanisms after such items have been selected at computer 330. Bins within the dispense drawer 352 may be assigned as PSBs on a temporary or more permanent basis to specific patients. The dispense drawer 352 may include a light 354 to guide the user to the dispense drawer 352 during dispensing operations. A handle 356 may be provided on door 346 to facilitate opening of door 346. The door 346 may include a light 357 to guide the user to the door 346 during dispensing operations.

In some cases, dispensed items may need to be returned to cabinet 310. In some situations, various laws, regulations, or facility policies prohibit dispensed items from being placed back into cabinet 310. As such, attached to (or otherwise integrated into) cabinet 310 may be a return unit 358 having a slidable (or rotatable) door 360 that may be opened to permit the item to be placed into the return unit 358. When returning the item, information regarding the return may be entered into computer 330. A light 362 on the return unit 358 may be lighted to indicate to the user that the item may be returned. The return unit 358 is preferably configured so that once an item is placed into the unit, the item cannot be retrieved from the return unit 358 unless a restock user or technician is authorized to gain access. For example, a restock technician may be required to enter appropriate information into computer 330 to cause the return unit 358 to unlock to allow access to the items within.

Although one specific arrangement of cabinet 310 has been described, it will be appreciated that any subset or combination of the above PSB components may be used with a variety of dispensing cabinets. For example, a dispensing mechanism and unit may be placed within a cabinet that is used solely for dispensing pharmaceuticals and may only include drawers similar to drawers 338. As another alternative, such mechanisms and units may be placed in a cabinet that only includes shelves that are similar to shelves 320. Further, such mechanisms and units may be used in cabinets having multiple shelves and/or drawers that are placed side-by-side in a vertical arrangement. Also, a dispensing cabinet may include multiple dispensing unit areas 342. These may be sized to the same size, or may be different sizes. Still further, in some cases such dispensing cabinets may include other types of shelves, racks, drawers, and the like to facilitate the storage of items.

Figure 4:
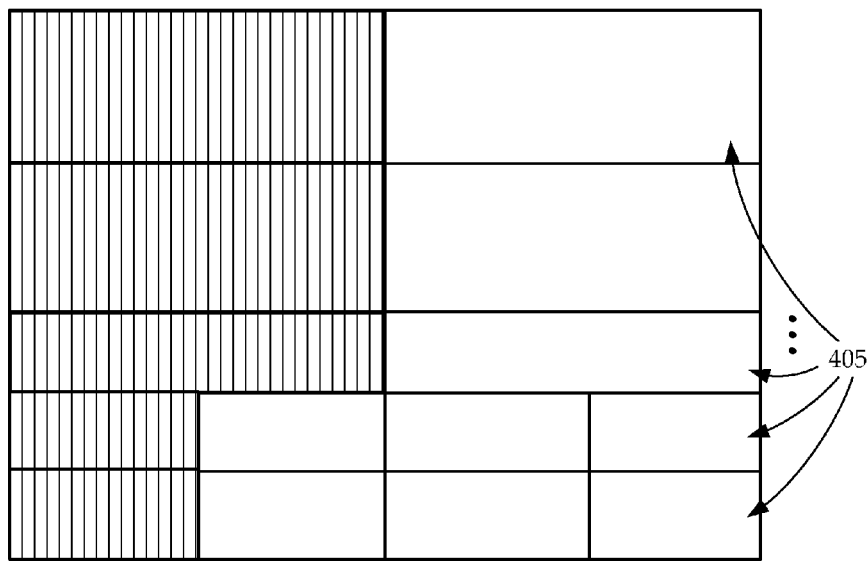
FIG. 4 illustrates a drawer of a cabinet dispensing device including patient-specific and item-specific bins according to various embodiments of the invention.

Referring next to FIG. 4, an illustration of one embodiment of a drawer 338 from FIG. 3 is shown. The allocations and patient assignments described with reference to the drawer 338 may be employed in other embodiments. In one embodiment, the drawer 338 includes a number of bins 405. There are a first subset 415 of the bins 405 that may be allocated to be assigned to patients, and a second subset 410 that may be allocated for assignment to items. In one embodiment, the computer 330 (or perhaps the central server computer system 105) may vary the allocations according to current and/or projected future inventory and use levels. In other embodiments, a drawer may be configured of only PSBs.

Figure 5:
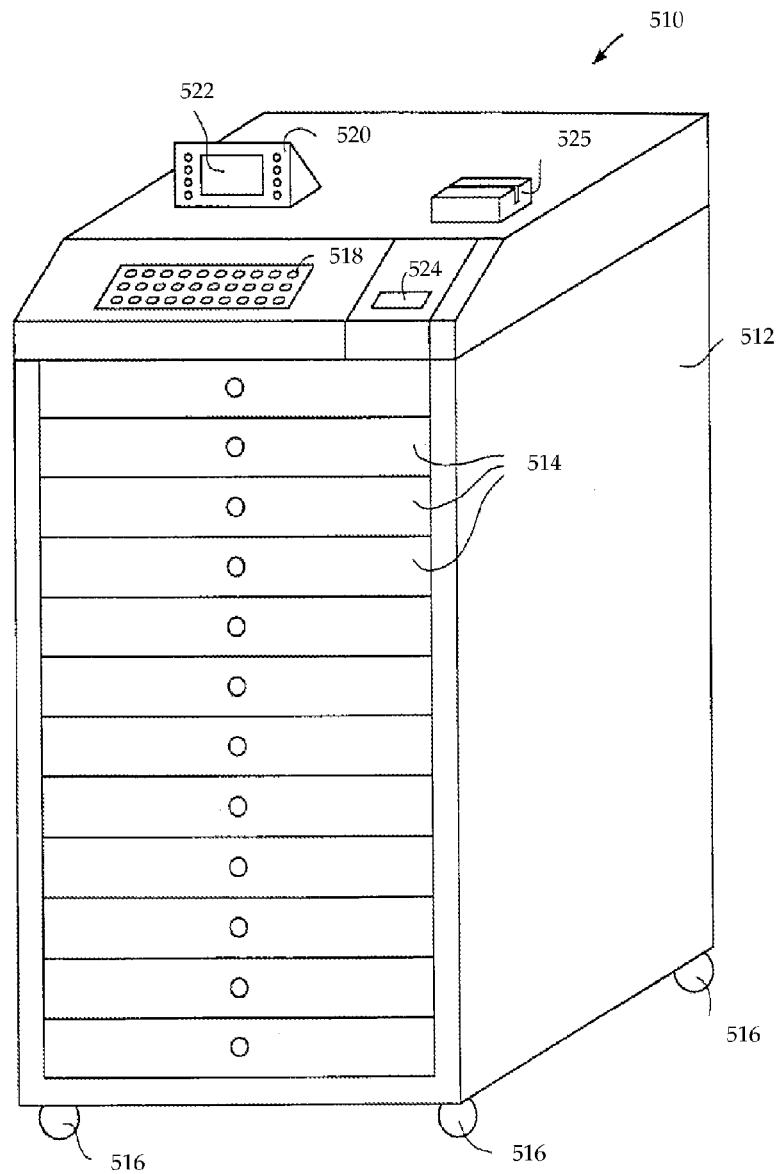
FIG. 5 illustrates a front perspective of an alternative cabinet dispensing device according to various embodiments of the invention.

There are a number of different configurations of other types of dispensing devices 120, and FIG. 5 illustrates yet another example of such a device. The illustrated dispensing device 510 may include one or all of the functions of the patient dispensing devices 120 described with reference to the system 100 of FIG. 1A or the system 150 of FIG. 1B, and thus may be implemented in either system. Thus, the device 510 may be in wired or wireless communication with the central server computer system 105.

The dispensing device 510 includes a cabinet 512 having a number of retractable drawers 514. Although shown with 12 drawers, the number of drawers may be varied. The cabinet 512 may rest upon wheels 516, which allow the dispensing device 510 to be wheeled throughout the healthcare facility. The cabinet may be battery powered and configured to communicate wirelessly (e.g., to allow communication while in transit). The cabinet 512 may be fashioned with various dimensions.

The dispensing device 510 further includes an integrated computer (hidden within cabinet 512) and a keyboard 518 for entering various information into the computer. For example, keyboard 518 may be employed to enter patient identification information, user identification information, requests for item stocking and removal, and the like into the computer. Optionally, the dispensing device 510 may further include a second entry device 520 which is connected to the computer and includes a screen 522 which allows the user to scroll through various lists of information in order to select a highlighted item. For example, a caregiver may scroll through a list of patient names or item names in order to select a certain patient or to enter an item removal or stocking request. In one embodiment, the screen may be a color touch screen. The touch screen may be configured to allow a user to interact with the dispensing cabinet, with or without having to use the keyboard, mouse, or other traditional methods, as the touch screen functionality allows a user to touch their selection directly. The touch screen may be a color touch screen, and color distinctions may inform and guide the user (e.g., alerts or warnings in yellow, item unavailability in grey, next steps in green).

A printer 524 may be provided on cabinet 512 to print various reports or labels generated by the computer. In other embodiments, some of the computing functionality for a device 510 (e.g., display, input device, reader, etc.) may be detachable or otherwise separate from the device 510, and may communicate wirelessly with the device 510 or central server computer system 105.

The cabinet 512 may further include a magnetic, bar code, RFID, data collector or other reader 525 which is connected (directly or wirelessly) to the computer. Such a reader 525 may be employed on any of the dispensing devices 120 described herein. It may be configured to manually or automatically scan for types and associated quantities or levels then provide the data to the cabinet 512 or to the central computer system 105. The reader 525 may be provided to allow a user, a patient, or particular medications or other supplies to be identified. For example, an identifier (e.g., magnetic, bar code, RFID, or other identifier) may be read from a medication container when an item is stocked, restocked, or removed. The identifier (and amount) may then be transmitted to the central server computer system 105 or otherwise stored, for purposes of tracking inventory. Similarly, an identifier (e.g., magnetic, bar code, RFID, or other identifier from an access card or other instrument) may be read from the user of the device or patient associated with the device. The reader 525 may also be employed to read an identification device associated with the drawers, as well.

To retrieve or remove items of a particular patient, a user (e.g., a nurse user or other caregiver, patient, automated system, etc.) may enter user identification (e.g., a password, PIN, smart card, RFID, combination thereof, etc.) using keyboard 518, reader 525, or entry device 520. The user (or the computer 330) may then identify the patient. The patient identification may be entered by the user using keyboard 518, reader 525, or entry device 520. The user may select the desired medication or other supplies, or the computer (or a central server computer system 105) may direct the user (via lights or a listing, for example). The user may also enter the number of items of the selected type that are to be removed or retrieved for the patient. The user may then retract the proper drawer and will be led to the correct bin. There may also be a step of verifying the count of specific items taken, by prompting the user to enter via keyboard 518 or entry device 520 the number of items of the specific type that were removed or supplied and the number remaining. A record of this event may also be maintained within the computer, or may be transmitted to the central server computer system 105 of FIG. 1A or 1B, or elsewhere. A variety of other removal alternatives may be used, as well.

For stocking and restocking of items into dispensing device 510, the pharmacy or other central dispensing unit (e.g., central dispensing unit 115 of FIG. 1A or 1B) may prepare all items for a particular cart fill at a particular PSB or set of PSBs together in a set of packages or other container. For example, all of the medications for a given PSB may be gathered and consolidated at the pharmacy or other central dispensing unit before they are placed in the cart. The computer for the cabinet 510, or perhaps the central server computer system 105 of FIG. 1A or 1B, may transmit the restock list to the pharmacy, or a list may be processed locally at the pharmacy. The process of gathering and consolidating the supplies for a particular PSB may therefore take place at the pharmacy or other central dispensing unit, instead of at the dispensing device 510. This may provide a more secure environment, and result in less loss. It may also be more efficient for a pharmacist instead of a nurse user to perform these tasks.

To stock or restock a PSB, the user may enter user, patient, and/or packages/container identification (e.g., a password, PIN, label, serial number, bar code, identification device, smart card, RFID, etc.) using keyboard 518, reader 525, or entry device 520. Thus, the entry of user, patient, or packages/container identification information (or any combination thereof) may trigger the restocking process. The computer for the cabinet 510 (perhaps controlled by the central server computer system 105 of FIG. 1A or 1B), may direct the user (e.g., via lights or screen information) to place the packages/container in the appropriate PSB. The action may be logged, and perhaps transmitted to the central server computer system 105.

In other embodiments, instead of having the pharmacy or other dispensing entity consolidate the restocking items, individual items may be placed in a PSB or ISB on an item-by-item basis at the dispensing device 510. For example, the pharmacy or other central dispensing unit (e.g., central dispensing unit 115 of FIG. 1A or 1B), or central server computer system 105 of FIG. 1A or 1B, may be in frequent contact with dispensing devices. Information may be exchanged with the dispensing devices, and in particular information on the current quantity on hand for each item in each dispensing device. At regular intervals (e.g., every morning) a restock list may be generated for each dispensing device, detailing the total quantity of each item to be taken to the dispensing devices to bring the quantity in each receptacle (e.g., PSB or ISB) up to a predetermined (or dynamically calculated) par level.

As another alternative, a pre-stocked liner for one or more bins may be prepared at the pharmacy, central dispensing unit, or elsewhere. The replacement liner may be configured to have the same arrangement of bins and items or a different arrangement of bins and items. A variety of other restocking systems may be used, as well. Although the retrieval and stocking are described with reference to the cabinet 510 of FIG. 5, these procedures may be applied to other dispensing devices (e.g., the dispensing device 120 of FIG. 1A or 1B), as well. The stocking or restocking may be performed when a patient first checks into a hospital, when there is a need for refills, or in managing a transfer, to name a few instances.

Figure 6:
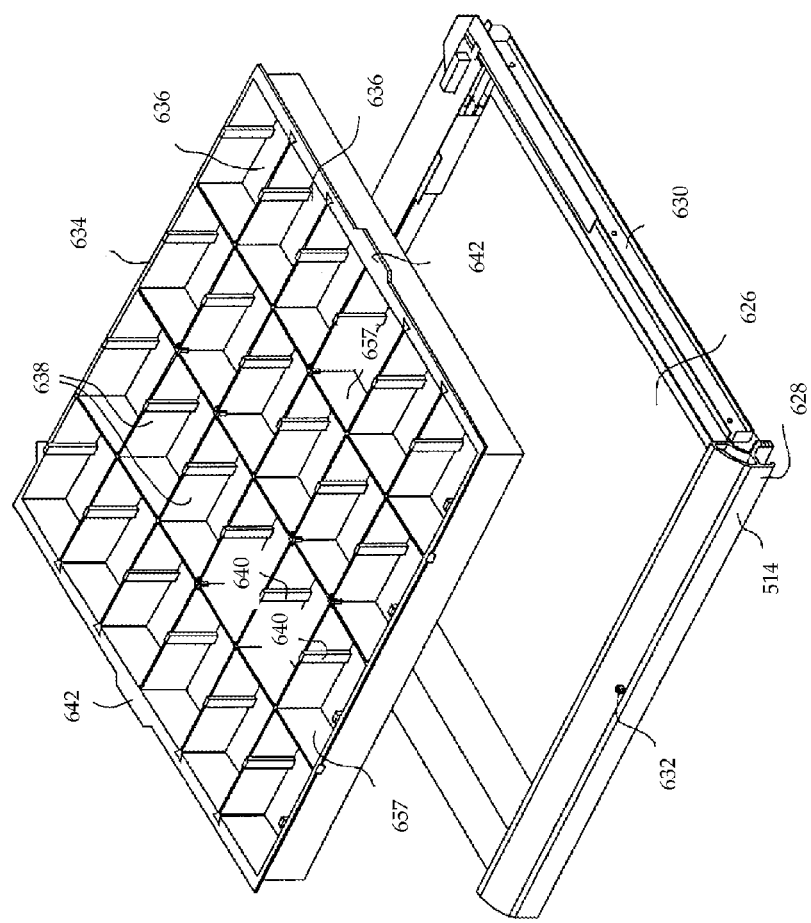
FIG. 6 illustrates a perspective view of a drawer of a cabinet dispensing device according to various embodiments of the invention.

Referring now to FIG. 6, an example of one of the drawers 514 from FIG. 5 will be described in greater detail. This drawer embodiment may be employed in a number of alternative dispensing devices, as well. Moreover, in other embodiments, a variety of different drawer configurations may be utilized, and this configuration is for purposes of example only. Drawer 514 of FIG. 6 includes a frame 626 having a handle 628 and a track 630 which allows the tray to be slid in and out of cabinet 512. A visual indicator 632, such as an LED, is provided on the drawer 514 to allow a specific drawer to be identified upon entering or otherwise receiving an item removal or stocking request. The drawer 514 may be configured to receive a removable liner 634 which holds the items to be dispensed. Liner 634 is divided into a number of bins 636 (which may be allocated or assigned as PSBs or ISBs, as described above). The bins in this embodiment include adjustable transverse dividers 638 and longitudinal dividers 657. Attached to at least some of the dividers are light pipes 640 which are employed to guide a user to a specific bin. Liner 634 is configured to rest within the frame 626 and may be removed by simply lifting the liner from drawer 514 by handles 642.

Figure 7:
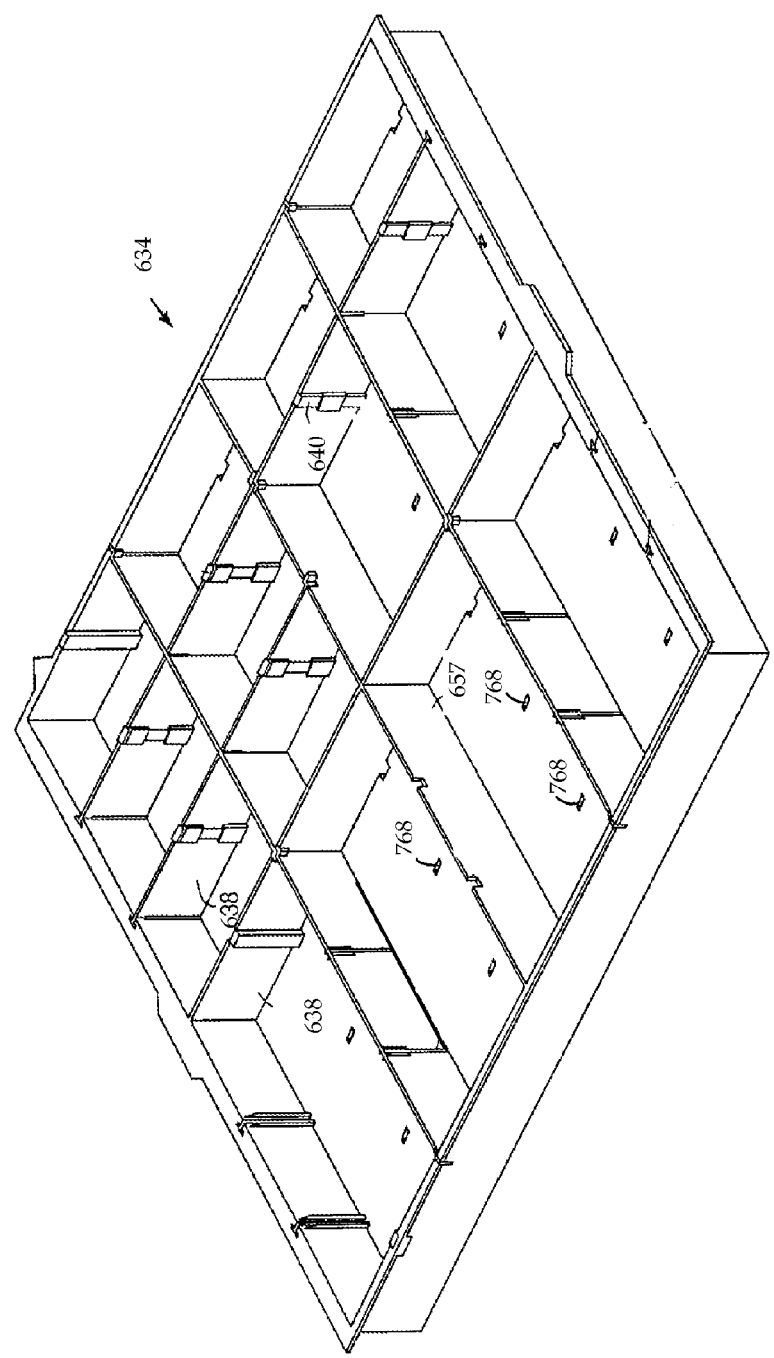
FIG. 7 illustrates a perspective view of a liner of a drawer of a cabinet dispensing device according to various embodiments of the invention.

Referring now to FIG. 7, an example of one of the liners 634 from FIG. 6 will be described in greater detail. In other embodiments, a variety of other liner configurations may be utilized, and this configuration is for purposes of example only. Within the liner, there are a number of apertures 768 for receiving light pipes 640. Apertures 768 are large enough to allow light pipes 640 to pass through liner 634. Apertures 768 are in a two-dimensional array so that an aperture 768 will be present for each light pipe 640 in a number of divider 638 configurations. In one embodiment, two light pipes 640 attached to separate dividers 638 (perhaps opposite each other) will be associated with each bin. In another embodiment, a single light pipe may uniquely identify each bin.

Figure 8:
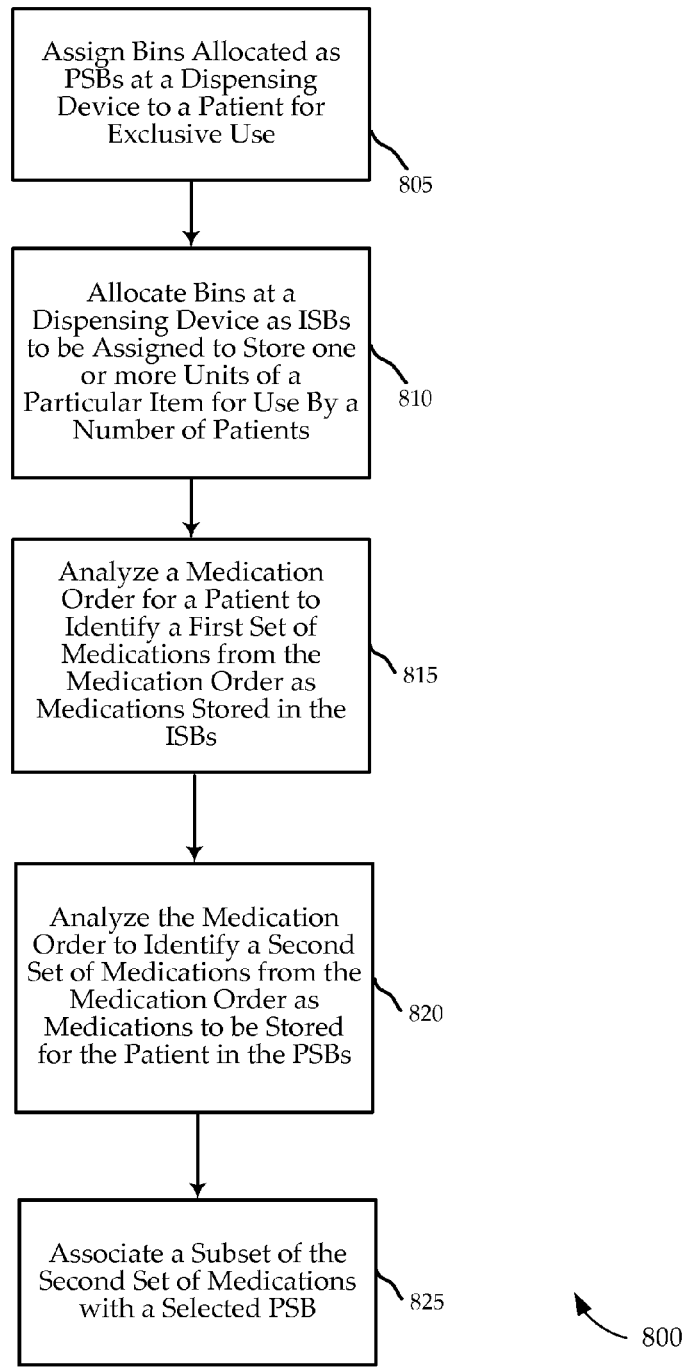
FIG. 8 is a flow diagram illustrating a method of assigning bins for dispensing devices according to various embodiments of the invention.

Referring next to FIG. 8, one embodiment of a method 800 of associating medications with bins in a dispensing device is described. This method 800 may, for example, be performed in whole or in part by the central server computer system 105 of FIG. 1A or 2. Alternatively, the method 800 may, for example, be performed in whole or in part by a computer associated with a dispensing device 120 or 220 of FIG. 1A, 1B, or 2.

At block 805, one or more bins at a dispensing device associated with a patient are allocated for PSB use and/or assigned to a patient for use as PSBs. At block 810, one or more different bins at the dispensing device are allocated for use as ISBs to be assigned to hold one or more units of a particular item for use by a number of patients. At block 815, one or more medication orders for the patient are analyzed to identify a first set of medications from the medication order(s) as medications stored in the ISBs. At block 820, the medication order(s) are analyzed to identify a second set of medications from the medication order(s) as medications to be stored for the patient in PSBs. The medication order(s) may be compared to a listing of items stored in the item-specific bins to identify the second set of medications. At block 825, a subset of the second set of medications is associated with a selected one of the PSBs. The selected PSB may be identified automatically, or may be selected by a user.

The medication order information for the patient may be received from other devices in the system. In one embodiment, the medication order information may be used to determine automatically which items to place in the selected PSB for the patient. The identifying data may then be transmitted (e.g., to the dispensing device 120 or central dispensing unit 115 of FIG. 1). The inventory at the selected PSB may be tracked by monitoring stocking and removal (e.g., when a central server computer system 105 receives stocking and removal information transmitted from a dispensing device 120). Items to be restocked in the selected PSB may be identified, based in part on the received medication order information and the tracked inventory.

The foregoing discussion provides a generalized description of a range of novel aspects of a system including PSBs. In turning to specific embodiments, additional novel aspects will now be discussed in Sections I-XIII. Although the system 100 of FIG. 1 is directly or indirectly referenced in the following description of certain embodiments of the invention, it must be emphasized that all illustrated components need not be used. Similarly, components not illustrated in the system 100 of FIG. 1 may be used in certain embodiments. For example, similar components (e.g., the central server computer system 105) of the system 200 in FIG. 2 may be used. Therefore, it should be recognized that any description related to FIG. 1 is for purposes of example only. Moreover, although many of the functions may be described as being performed by the central server computer system 105, the functions described (or any subset thereof) may be performed by the computer of patient dispensing device 120 of FIG. 1A or 1B or dispensing device 220 of FIG. 2.

In the following discussion, the items to be dispensed are often described as medications. However, this is for purposes of example only, as the principles set forth may be applied to the storage of other medical supplies, as well. In a number of embodiments described below, the system 100 includes a patient dispensing device 120-*a* (e.g., a nursing unit cabinet), with a subset of bins allocated for assignment to a patient as PSBs. While it may not be noted in each instance, there may also be ISBs available for assignment to a particular type of item to be used by a number of patients. In this application, the term "PSB" is used interchangeably with the term "patient-specific bin," and the term "ISB" is used interchangeably with the term "item-specific bin."

I. Status Designation for Dispensing Device: In one set of embodiments, a patient may be associated with dispensing devices at two different physical locations at the same time. Referring initially back to the system 100 of FIG. 1, the system 100 may be configured to address the instances when a patient's physical location is mobile or transitory within a healthcare facility. Each dispensing device 120 may have a different designated status defining the services to be provided at the respective device. A system 100 may, therefore, be configured to be flexible to address patient needs at different locations, and in instances when a location (e.g., a room or area) associated with a patient is a future, past, temporary, or mobile location. Status designation may also address circumstances when the patient's actual location is uncertain or unknown.

Therefore, in one embodiment, a central server computer system 105 of FIG. 1A associates a different status to two or more dispensing devices 120 associated with a patient. In doing so, when a PSB in the dispensing device is assigned to the patient, the status designation of the dispensing device 120 may define the status of the PSB, as well. Thus, status designations may be attributed to a particular dispensing device 120 or a PSB. A status designation may indicate which services are to be provided to a patient at a given location.

Figure 9:
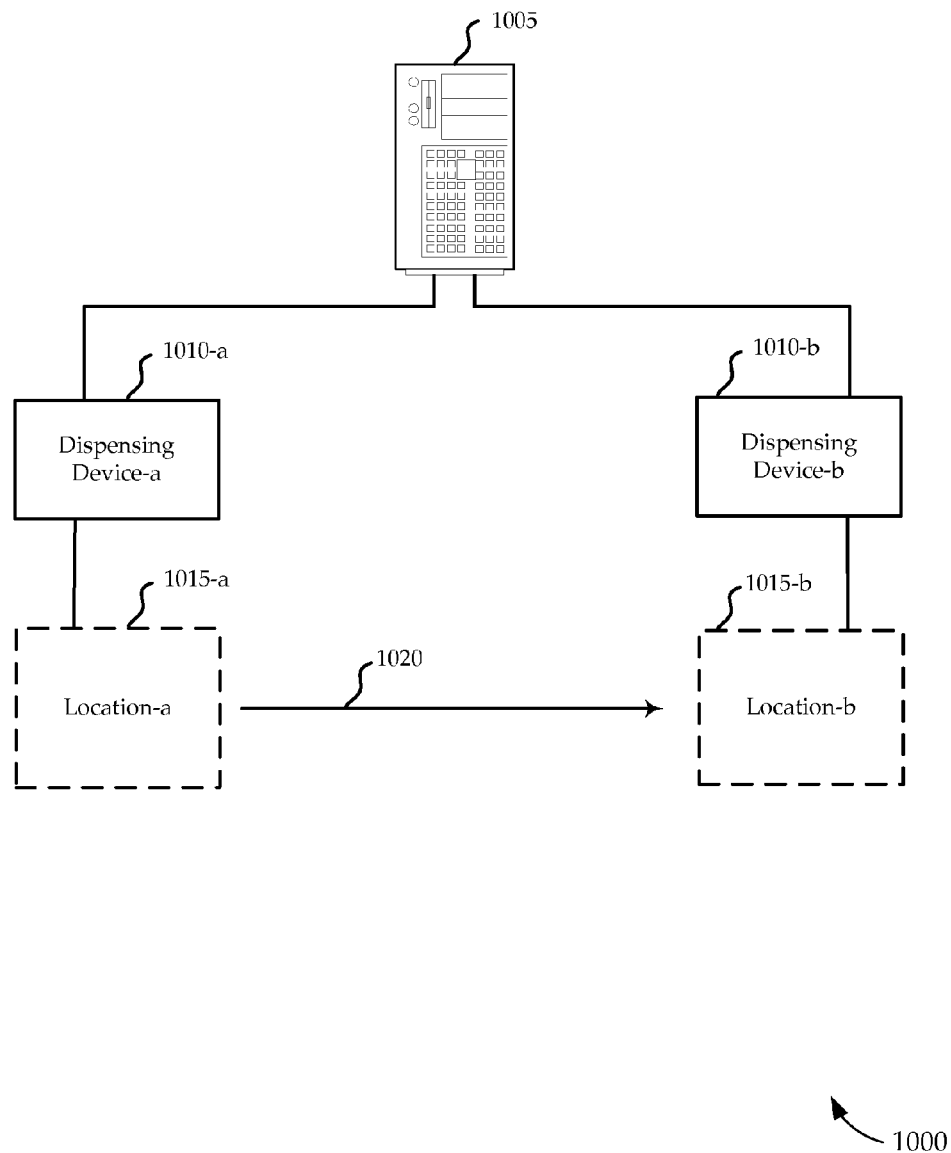
FIG. 9 is a block diagram illustrating a system for status designation at dispensing devices according to various embodiments of the invention.

Turning to FIG. 9, an example of a system 1000 is illustrated for designating the status of a dispensing device which includes patient-specific bins. The illustrated system 1000 includes two dispensing devices, dispensing device-a 1010-*a* and dispensing device-b 1010-*b*. Each device may, for example, be a dispensing device 120 or 220 of FIG. 1A, 1B, or 2, and thus may be a cabinet with a number of bins for dispensing medical supplies (e.g., pharmaceuticals, other medications, or other supplies for a patient at a healthcare facility). The system 1000 also includes a central server computer system 1005, which is communicatively connected with each dispensing device 1010. The central server computer system 1005 may be the central server computer system 105 of FIG. 1A, 1B, or 2. The system may include any other number of connected dispensing devices (not shown), and thus the illustrated embodiment is for purposes of example only.

Dispensing device-a 1010-*a* may be associated with location-a 1015-*a*. This association may indicate that dispensing device-a 1010-*a* is a cabinet at a nursing station serving a set of rooms which include location-a 1015-*a*. The patient may be physically located within one of the rooms of location-a 1015-*a*, and the central server computer system 1005 may reflect this association. However, in some embodiments, location-a 1015-*a* may be a past or future location for the patient, or be another type of room or location (e.g., an operating room, emergency room, a transitory location between two rooms, etc.).

Dispensing device-b 1010-*b* may be associated with location-b 1015-*b*. This association may also indicate that dispensing device-b 1010-*b* is a cabinet at a nursing station serving a set of rooms which include location-b 1015-*b*. The patient may again be associated with location-b 1015-*b*, as the location-b 1015-*b* may be a past, present, or future location of the patient, either in fact or as represented by the central server computer system 1005.

Therefore, because a patient may be associated with dispensing devices 1010 at two different locations 1015-*a* and 1015-*b*, the patient medication and other supply needs may be served from each location. However, in one embodiment, there is a different status associated with each dispensing device 1010-*a* and 1010-*b*, the status providing an indication of the services which are allowed (or are required) to be provided at each device 1010 (and thereby at one or more PSBs therein). The different status designations may concurrently be in effect. Each status designator may, therefore, provide different limitations and/or requirements on the services that may be provided at each location at a given time (e.g., user behavior may be restricted based on a first status designation at one device 1010-*a*, but not at another device with a different designation 1010-*b*).

The central server computer system 1005 (or, perhaps, a computer for each device 1010) may designate, change and store the status associated with each device 1010. The status designations may be mutually exclusive, or the system may be configured to share designations among different devices.

There may be any number of status designations available for a given system 1000. The following designations are possible, but are only for purposes of example, as those skilled in the art will recognize the range of possibilities:

- Active: designated to a dispensing device 1010 associated with the patient's room in the rooms table, although not necessarily where the patient is physically located;
- Interim: designated to a dispensing device 1010 associated with the room where the patient was located before a new cabinet was designated as the active cabinet. The interim cabinet may, but need not necessarily be, where the patient is physically located;
- Inactive: designated to a dispensing device 1010 after confirmation is received that a patient has physically moved from a previously active device 1010 and/or his medication and other supplies at the device have been physically removed;
- Temporary: designated to a dispensing device 1010 in a room or location that the patient will occupy only temporarily (e.g., 4 hours or less, 6 hours or less, etc.). An operating room or other temporary procedure area (e.g., an x-ray or therapy room) might have this designation;
- Transitory: designated to a dispensing device 1010 associated with a patient who is being moved (e.g., between healthcare facilities, or within a healthcare facility); or
- Delivery: designated to a mobile dispensing device 1010 used for delivering medications and associated with the patient.

For each status designation, a different set of services may be allowed, prohibited, required, etc. For example, a status may require that certain services be provided, and/or may limit the services that are provided to certain users. The set of services that are associated with a given status may be set, or they may be programmed or modified by an administrator. Certain users may be given the ability to override the set of services mandated or allowed at a device of a given status.

In one embodiment, all or any subset of the following functions may be limited or mandated at a device 120 or PSB based on a given status designation: item removal, item return, return location, item destock, PSB control level, PSB attribute modification, restock and/or restock supply level, supplemental restock and supplemental restock supply level, item assign or un-assign, patient bin assign or un-assign, PSB designation or reallocation, transfer patient medications, receive patient medications, expiration tracking, item bar code confirmation, quantity verification, witness requirements and/or receive or remove patient's own medications. By way of example, a status designation at a location may dictate where a restock list is to be sent, which items are to be restocked at respective locations, what quantities (days' supply) are to be restocked, when a cabinet should be cleaned, which items are to be removed, where removed items should be placed, whether a patient is being transferred or discharged, which patient care services may be provided at the location, and so on.

The status designations may be entered by a user, or may be entered or modified automatically (e.g., the central server computer system 1005 or computer for the device 1010). For example, consider an example of a patient moving 1020 from location-a 1015-*a* to location-b 1015-*b*. The status designation of a first device 1010-*a* may be changed automatically upon receiving information confirming the patient has physically arrived at location-b 1015-*b*. The status designation of the first device 1010-*a* may be changed automatically upon receiving information confirming the patient has physically departed from location-a 1015-*a*, or that the patient's physical location has otherwise changed. Thus, a status designation change may be automatically triggered by a confirmation of a physical location change (departure, arrival, other change). The changed status designation may trigger removal of items stored in a PSB for the patient at dispensing device-a 1010-*a* (e.g., triggering immediate removal, or simply when a user next uses the device 1010-*a*).

Figure 10:
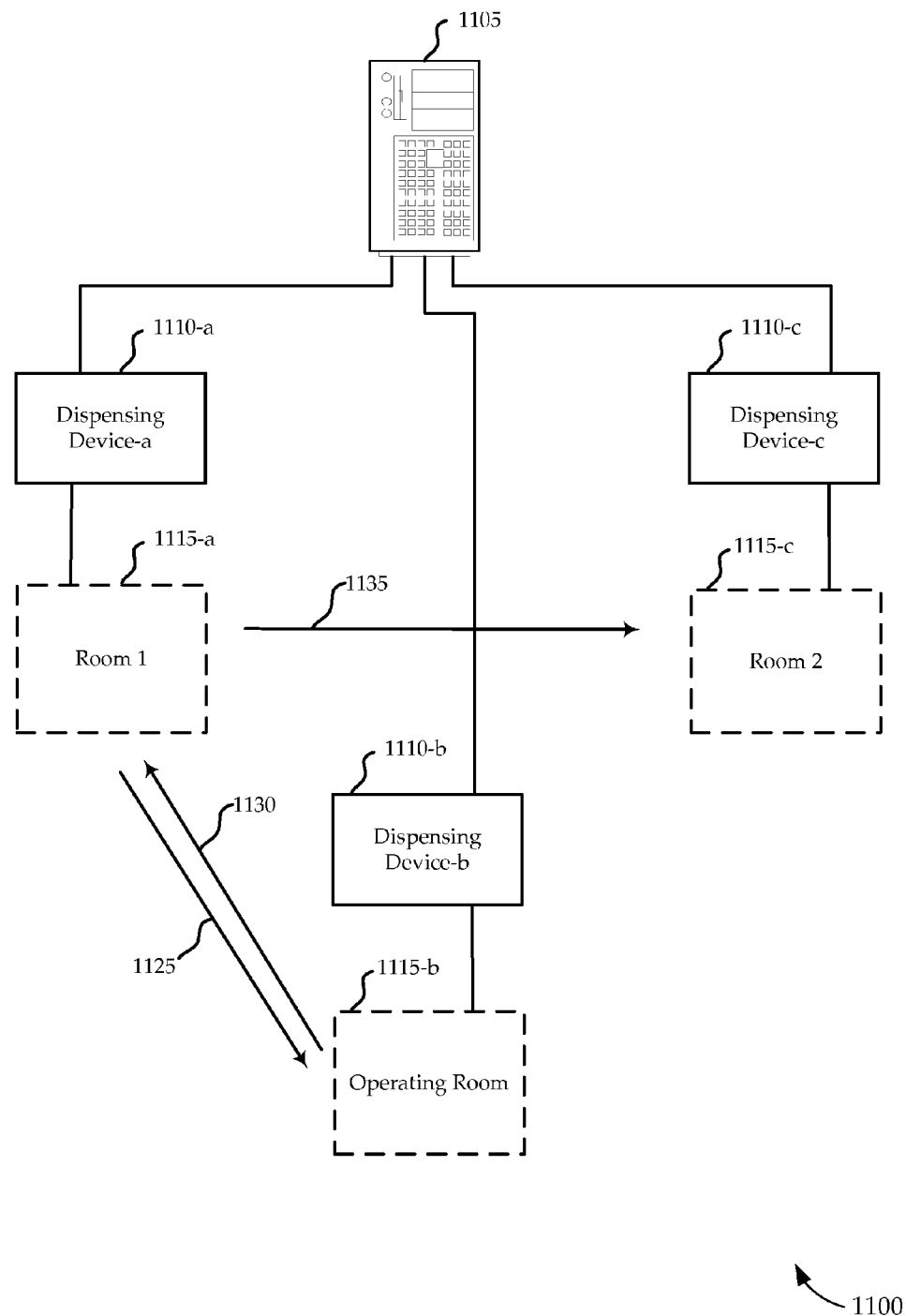
FIG. 10 is a block diagram illustrating an alternative system for status designation at dispensing devices according to various embodiments of the invention.

Referring next to FIG. 10, an example of a system 1100 is illustrated for designating the status of dispensing devices which include PSBs. The illustrated system 1100 includes three such dispensing devices, dispensing device-a 1110-*a*, dispensing device-b 1110-*b*, and dispensing device-c 1110-*c*. Each device may, for example, be a dispensing device 120 or 220 of FIG. 1A, 1B, or 2, and thus may be a cabinet with a number of bins for dispensing medical supplies (e.g., pharmaceuticals, other medications, or other supplies for a patient at a healthcare facility). The system 1100 also includes a central server computer system 1105, which is communicatively connected with each dispensing device 1110. The central server computer system 1105 may be the central server computer system 105 of FIG. 1A, 1B, or 2. The central server computer system 1105 may include any other number of communicatively connected dispensing devices (not shown), and thus the illustrated embodiment is for purposes of example only.

Dispensing device-a 1110-*a* is associated with room 1 1115-*a* (e.g., in the rooms table 210-*a* of FIG. 2). This association may indicate that dispensing device-a 1110-*a* is a cabinet at a nursing station serving a set of rooms which include room 1 1115-*a*. In this example, the patient is initially physically located within room 1 1115-*a*, and the central server computer system 1105 reflects this association. In the current example, dispensing device-a 1110-*a* is designated with an active status, indicating that the dispensing device provides full functionality to the patient.

Dispensing device-b 1110-*b* is associated with an operating room 1115-*b* (e.g., in the rooms table 210-*a* of FIG. 2). This association may indicate that dispensing device-b 1110-*b* is a cabinet at the operating room 1115-*b* or a nursing station serving the operating room 1115-*b*. When the patient is moved 1125 to have a procedure performed in the operating room 1115-*b*, the central server computer system 1105 may reflect this association (e.g., for a future operation, or when the operation is occurring). Dispensing device-b 1110-*b* may be designated with a temporary status, indicating that the dispensing device provides functionality to the patient (e.g., restocking) for only the scheduled operating time plus a margin. This may mean that the amount of restocking is limited, and/or that certain types of restocking lists should be routed only to the active dispensing device 1110-*a*. Other limitations or requirements may be associated with the temporary status, as well. Once it has been confirmed that the patient has physically left 1130 the operating room 1115-*b* or returned 1130 to room 1 1115-*a* after an operation, dispensing device-b 1110-*b* could be designated with an inactive status, triggering the cleaning of dispensing device-b 1110-*b*.

Dispensing device-c 1110-*c* is associated with room 2 1115-*c* (e.g., in a rooms table 210-*a* of FIG. 2). This association may indicate that dispensing device-c 1110-*c* is a cabinet at a nursing station serving a set of rooms which include room 2 1115-*c*. The central server computer system 1105 may receive information that the patient is to be transferred 1135 to room 2 1115-*c*, and may reflect this association. Dispensing device-c 1110-*c* is designated with an active status, indicating that the dispensing device provides full functionality to the patient. There may not yet be confirmation that the patient has vacated room 1 1110-*a*. An interim status may, therefore, be designated to dispensing device-a 1110-*a* (i.e., the room where the patient was located before a transfer). Note that stocked items at the interim PSB may not have been transferred, and the patient may not yet have been physically transferred. A dispensing device with interim status may provide some subset of the functionality provided by the device with active status. After receiving confirmation that the patient and/or his medication and other supplies at dispensing device-a 1010-*a* have been physically transferred (e.g., a confirmation received by the central server computer system 105), dispensing device-a 1010-*a* may be designated with inactive status for the patient.

Figure 11:
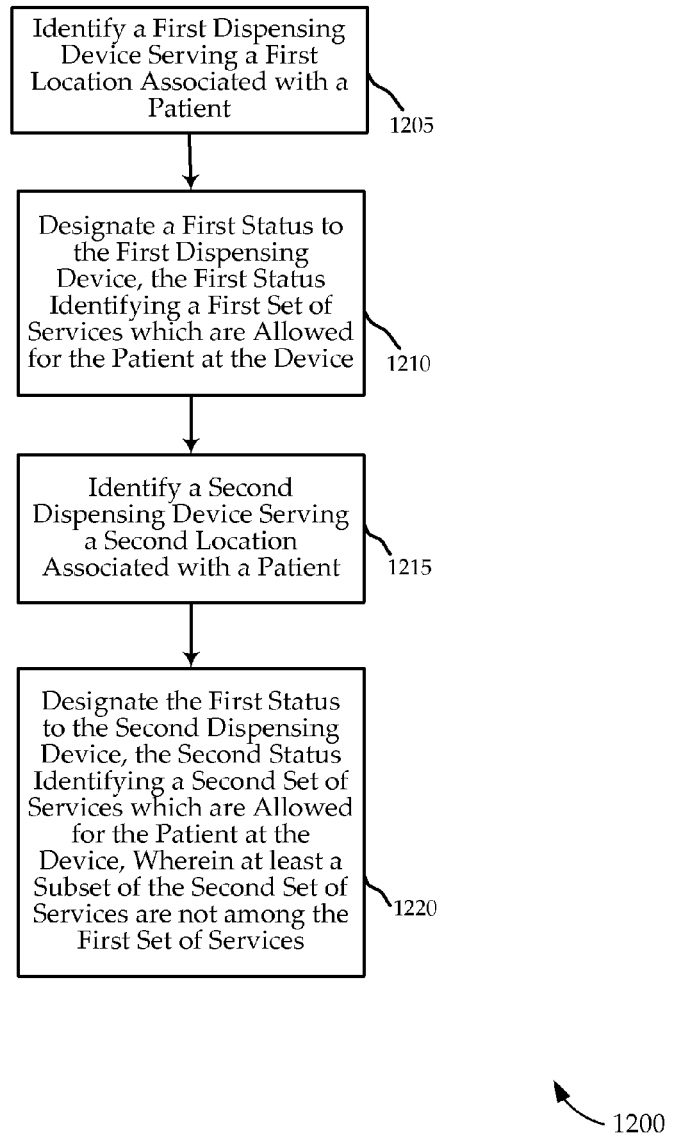
FIG. 11 is a flow diagram illustrating a method of status designation for dispensing devices according to various embodiments of the invention.

Referring next to FIG. 11, one embodiment of a method 1200 of designating status to dispensing devices is illustrated. This method 1200 may, for example, be performed in whole or in part by the central server computer system 105 of FIG. 1A or 2. Alternatively, the method 1200 may, for example, be performed in whole or in part by a computer associated with a dispensing device 120 or 220 of FIG. 1A, 1B, or 2. In this embodiment, the dispensing device 120 is a cabinet.

At block 1205, a first dispensing device serving a first location associated with a patient is identified. This may, for example, be a cabinet serving an area which includes a room that is currently assigned to the patient. Alternatively, this may be a cabinet serving an area which includes a room that was previously assigned to a patient, when the system lacks confirmation that the patient has left the room. This may also be a mobile cabinet serving a patient in transit (e.g., within or outside a healthcare facility), a temporary cabinet (e.g., assigned during a procedure), or a cabinet that will be assigned in the future. At block 1210, a first status is designated to the first dispensing device, the first status identifying a first set of services which are allowed for the patient at the device.

At block 1215, a second dispensing device serving a second location associated with a patient is identified. This may, for example, be a cabinet serving an area which includes a room that is currently or was previously assigned to the patient, or be a mobile, temporary, or future cabinet. At block 1220, a second status is designated to the second dispensing device, the second status identifying a second set of services which are allowed for the patient at the device. At least a subset of the second set of services is not among the first set of services. In one embodiment, therefore, different status designations may specify the different services allowed for a device.

Figure 12:
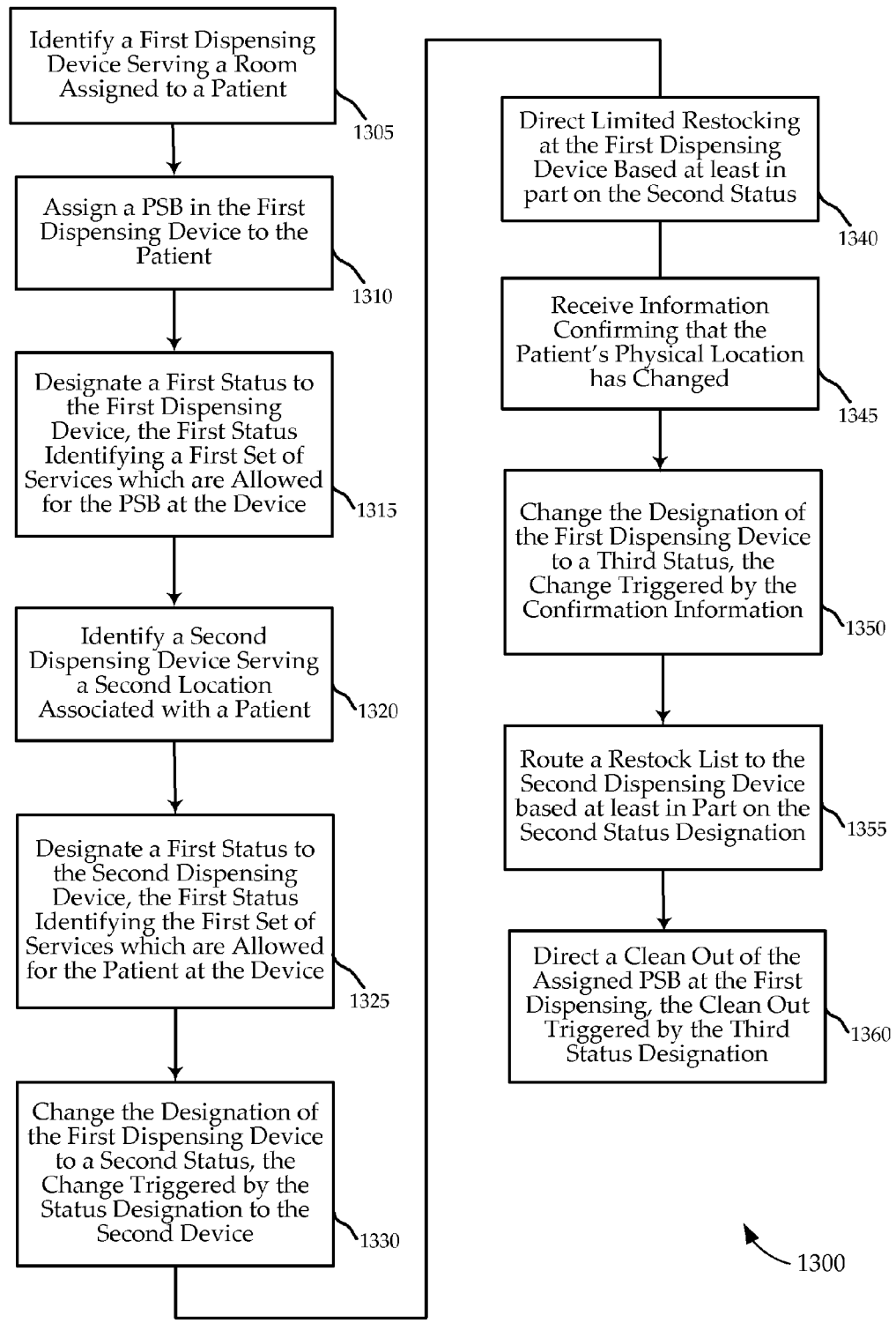
FIG. 12 is a flow diagram illustrating an alternative method of status designation for dispensing devices according to various embodiments of the invention.

Referring next to FIG. 12, an alternative embodiment of a method 1300 of designating status to dispensing devices is illustrated. This method 1300 may, for example, be performed in whole or in part by the central server computer system 105, the computer associated with a dispensing device 120 or 220, or any combination thereof. Each step may be performed automatically (without user or operator action or involvement), or may in whole or in part be initiated and/or performed by a user providing input to the applicable computing device. In this embodiment, the dispensing device 120 is a cabinet.

At block 1305, a first dispensing device is identified as serving a room assigned to a patient. At block 1310, a PSB in the first dispensing device is assigned to the patient. At block 1315, a first status is designated to the first dispensing device, the first status identifying a set of services which are allowed for the PSB at the device. The allowed services may be identified indirectly (for example, via a listing of allowed services stored at the central server computer system 105, the listing corresponding to the status).

At block 1320, a second dispensing device is identified as serving a second location associated with a patient. At block 1325, the first status is designated to the second dispensing device, the first status again identifying the first set of services which are allowed for the patient at the device. At block 1330, the designation of the first dispensing device is changed to a second status, the change triggered by the status designation at the second dispensing device. In one embodiment, at least some of the status designators are mutually exclusive; in other embodiments, the status designator may be shared. At block 1340, a limited restocking is directed to the first dispensing device, the limited restocking based at least in part on the second status. A "limited restocking" may mean that only certain items and/or only smaller quantities of a given item are restocked at the device.

Figure 13:
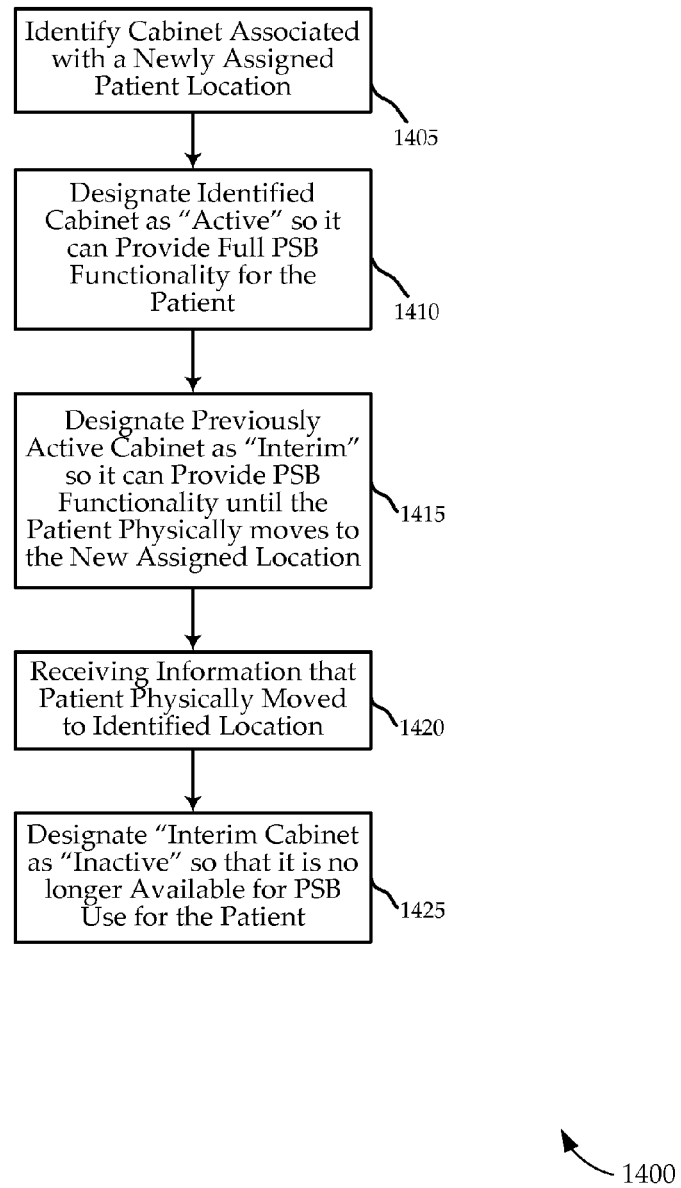
FIG. 13 is a flow diagram illustrating yet another alternative method of status designation for dispensing devices according to various embodiments of the invention.

At block 1345, information is received confirming that the patient's physical location has changed (e.g., that the patient has left the first location or that the patient has arrived at the second location. At block 1350, the designation of the first dispensing device is changed to a third status, the change triggered by the confirmation information. At block 1355, a restock list is routed to the second dispensing device based at least in part on the second status designation At block 1360, a clean out directive for the assigned PSB is routed to the first dispensing device, the clean out directive triggered by the third designation Referring next to FIG. 13, one embodiment of a method 1400 of designating status to dispensing devices is illustrated. This method 1400 may, for example, be performed in whole or in part by the central server computer system 105, the computer associated with a dispensing device 120 or 220, or any combination thereof. In this embodiment, the dispensing device 120 is a cabinet.

At block 1405, a cabinet associated with a newly assigned patient location is identified (e.g., via the rooms table 210-*a* of FIG. 2). At block 1410, the identified cabinet is identified as the "active" cabinet, so it can provide full PSB functionality for the patient. At block 1415, the previously "active" cabinet is designated as "interim" so it can continue to provide PSB functionality (either full functionality or perhaps limited to certain items or quantities) until the patient physically moves to the new assigned location. Thus, in certain embodiments, the activities that may be performed from the interim cabinet may be limited due to the "interim" designation.

After the patient physically moves to a new assigned location, at block 1420 information is received indicating that the patient has been physically moved. At block 1425, the designation of the interim cabinet is changed to "inactive" so that it is no longer available for PSB use for the patient. This designation may, for example, trigger the cleaning of the inactive cabinet.

II. Identifying Items for Restocking of a Dispensing Device: For another set of embodiments, various systems, methods, and devices are described for identifying items in a medication order that are to be reordered. The items from one or more medication orders may be compared to the items in common stock (e.g., in ISBs) at a dispensing device, to identify items that are to be stored in PSBs for the patient. Of those items to be stored in the PSBs, those that are at or below reorder levels may be identified for a restock list to be generated for a dispensing device 120 or 220 of FIG. 1A, 1B, or 2.

A set of example embodiments will now be described with reference to FIG. 2. It is worth noting, however, that the functions described may be performed by the central server computer system 105 of FIG. 1A or 2, the computer associated with a dispensing device 120 or 220 of FIG. 1A, 1B, or 2, or any combination thereof. A system 200 includes a number of dispensing devices 220 in communication with a central server computer system 105 at a healthcare facility. Each dispensing device 220 may be associated with one or more rooms or areas. A patient is assigned a room, and thus a nursing unit cabinet 220-c may be associated with the room assigned to the patient (e.g., via rooms table 210-a). In other embodiments, a range of other types of dispensing devices 120 or 220 may be used.

In one embodiment, the nursing unit cabinet 220-c includes one or more PSBs assigned for exclusive use to a patient of a plurality of patients, and one or more ISBs each allocated for an item available to be used by the plurality of patients. An ISB is a bin which is assigned to an item independent of the item's relation to a patient (e.g., it may be for use among two or more patients). The central server computer system 105 may dynamically allocate the bins for patient- or item-specific use, or the allocation may be static.

In one embodiment, a medication order is generated or received by the central server computer system 105. The order may identify a medication or medications to be administered for or otherwise used by a patient, based on current or future needs (e.g., the medication order may be an active or future order). While the medication order may be generated internally (by the central server computer system 105 or a dispensing device 120 computer), it may alternatively be received from an external source (e.g., an external source of patient information and medication orders). The medication order may be compared to a listing of medications stored in the one or more ISBs at the nursing cabinet 220-c (e.g., the common stock), to determine those items of the medication order to be stored in the one or more PSBs at the cabinet 220-c (e.g., the items in the medication order not in common stock). There may be items that are not in common stock at the cabinet 220-c, and yet which are not to be stored in PSBs (e.g., excluded items). The items to be stored in PSBs may already be stocked for the patient or may be new items that were not previously stocked.

The central server computer system 105 may identify a reorder level for one or more of the items to be stored in a PSB at the cabinet 220-c, the reorder level triggering reorder of respective items. The central server computer system 105 may then determine whether the one or more PSBs for the patient at the cabinet 220-c are at or below the identified reorder levels. A central server computer system may receive data from the cabinet 220-c, or elsewhere, identifying current levels of supply for the items of the medication order to be stocked in PSBs. Thus, the central server computer system 105 (or the dispensing device 120 computer) may monitor the actual usage and actual quantity on hand in both PSBs and ISBs to provide updated information. In one embodiment, the data is used in the determination of whether the PSBs for the patient at the device are at or below the identified reorder levels. It is worth noting that a particular medication order may be associated with one, or more, medications. Thus, a number of medication orders may be analyzed for a particular patient at a given time at a device 220, or a single medication order may be analyzed including a number of medications.

The central server computer system 105 may be further configured to identify, for items determined to be at or below the identified reorder levels, a reorder amount for the patient at the dispensing device. The central server computer system 105 may identify a target level at which to bring the items for the patient in restocking the dispensing device. Thus, the central server computer system 105 may identify a reorder amount for the patient for each item by comparing the target level to a current level of supply.

Figure 14:
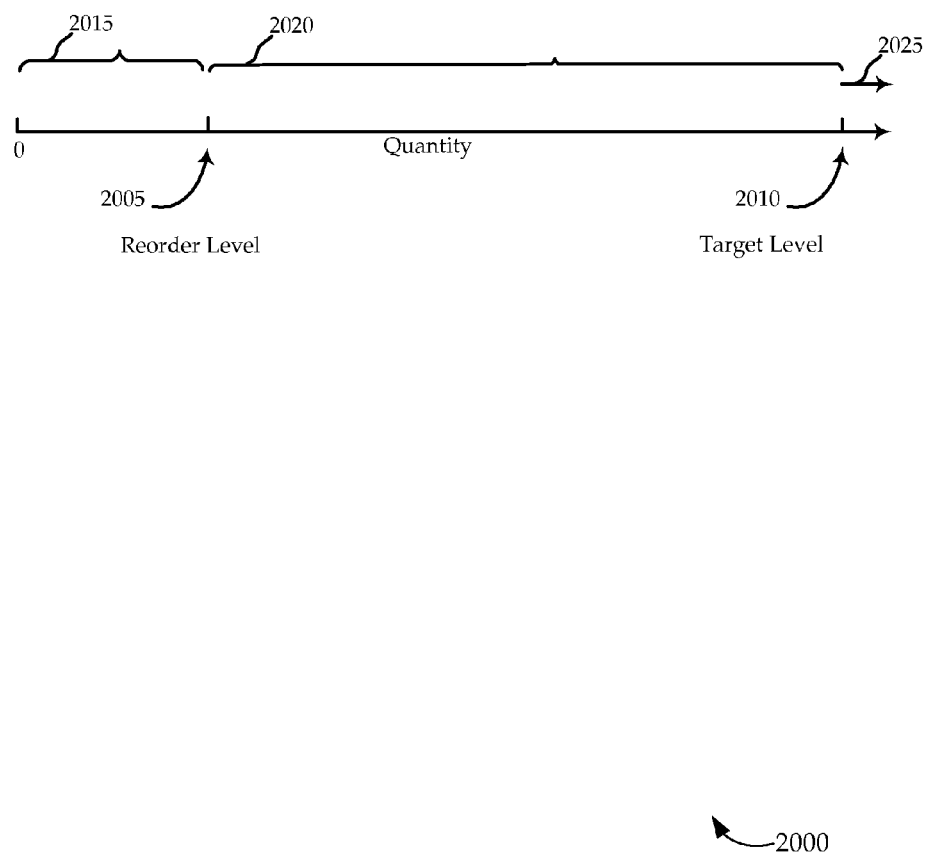
FIG. 14 is a diagram illustrating a reorder level and a target level for an item to be stored for a patient at a patient-specific bin at a dispensing device according to various embodiments of the invention.

Referring next to FIG. 14, an example diagram 2000 illustrates a reorder level 2005 and a target level 2010 for an item to be stored for a patient at a PSB at a dispensing device (e.g., the dispensing device 120 of FIG. 1A, or cabinet 220-c of FIG. 2). The following functionality may, for example, be undertaken by the central server computer system 105. At specified times (e.g., one or two times daily), one or more medication orders may be analyzed to determined the use requirements of a patient for an item to be stocked in a PSB at a dispensing device.

Based, for example, on consumption rates and a minimum supply amount (e.g., measured in time), a reorder level 2005 may be identified. The reorder level may be the supply level triggering reorder. A current level of supply of the item at the PSB may also be identified. If the current quantity of the item in the PSB is at a lower level 2015 than the reorder level 2005 when the medication order is processed, a reorder for the item is triggered. Based, for example, on consumption rates and a desired re-supply amount (e.g., measured in time), a target level 2010 may be identified. The target level 2010 may be the supply level to which to bring the quantity upon restock. The reorder quantity may be the difference between the current level of supply and the target level 2010. If the quantity of the items in the bin(s) is at a higher level 2020 than the reorder level 2005 when the medication order is processed, no reorder is triggered. If the medication order changes, and the current supply of items is at a higher level 2025 than the target level 2010, the dispensing device 120 may (or may not) be directed to have the items removed (e.g., during cleaning or at other times), depending on the amount of overage and estimated remaining use of the items by the patient (e.g., as set forth in a current or future medication order). Those skilled in the art will recognize the many implementation options for such a system.

The medication order or other consumption information (e.g., based on an estimate using past use rates for the patient or like patients) may be used to determine a rate of use by the patient for each item, and the rate of use may be used to identify the reorder level and/or the target level. A central server computer system 105 may, for example, identify a reorder days supply and a target days supply for the one or more items at the dispensing device 120. The target days supply may be used in conjunction with the consumption information to identify the target level. Similarly, the reorder days supply may be used in conjunction with the consumption information to identify the reorder level. Additionally, the reorder level or target level may be modified if the rate of use changes, as a modified rate of use would change the number of days supply (for a given level of supply).

Table 1 illustrates an example of reorder and target levels, based on a days supply calculation. Table 1 is a table for Drug A, with a medication order indicating that Drug A is to be administered three times per day (at 9:00 a.m., 1:00 p.m., and 8:00 p.m.) for ten days. The reorder time is at 8:00 a.m. The reorder level is one days supply, and the target level is four days supply. For the above medication order (setting forth administration three times per day), the reorder level is three items (1 day×3 items), and the target level is twelve items (4 days×3 items). The system may be able to identify current levels in analyzing reorder quantities, and thus may identify when an administration was skipped (e.g., day 3).

TABLE 1

| Day # | Day of week | | | | | | | | | | Med order stopped |
|---|---|---|---|---|---|---|---|---|---|---|---|
| | Mon Dy 1 | Tues Day 2 | Wed Day 3 | Thur Day 4 | Fri Day 5 | Sat Day 6 | Sun Day 7 | Mon Day 8 | Tues Day 9 | Wed Day 10 | |
| Reorder Qty-Doses needed 8 am | 12 | 0 | 0 | 0 | 11 | 0 | 0 | 6 | 0 | 0 | |
| QOH | 12 | 9 | 6 | 4 | 12 | 9 | 6 | 9 | 7 | 4 | |
| Dose given 9 am | 1 | 1 | 0 | 1 | 1 | 1 | 1 | 1 | 1 | 1 | |
| Dose given 1300 | 1 | 1 | 1 | 1 | 1 | 1 | 1 | 1 | 1 | 1 | |
| Dose given 2100 | 1 | 1 | 1 | 1 | 1 | 1 | 1 | 0 | 1 | 1 | |
| QOH | 9 | 6 | 4 | 1 | 9 | 6 | 3 | 7 | 4 | 1 | |

Table 1, therefore, illustrates an example of an embodiment in which the reorder levels and target levels may be measured in terms of days of use. The actual reorder levels and target levels may vary depending on the rate of use and amount of the medication order remaining to be taken. For example, if the medication order changed, the reorder level and target level may change as a function thereof.

The reorder process described herein may include both active and future medication orders. Table 2 illustrates an example of a series of active and future medication orders for Drug B. It also illustrates how amounts attributable to a days supply (either target or reorder) may vary over time. Drug B is to be administered, in decreasing amounts, 1 time per day (at 9:00 a.m.) for 6 days.

TABLE 2

| MO # | Med Order | Item | MO Dose | QTY | MO Start time | MO Stop time |
|---|---|---|---|---|---|---|
| 1 | Drug B 30 mg × 1 | Drug B 10 mg | 30 mg | 3 | Oct. 1, 2007 0900 | Oct. 1, 2007 0900 |
| 2 | Drug B 20 mg × 1 | Drug B 20 mg | 20 mg | 1 | Oct. 2, 2007 0900 | Oct. 2, 2007 0900 |
| 3 | Drug B 10 mg × 1 | Drug B 10 mg | 10 mg | 1 | Oct. 3, 2007 0900 | Oct. 3, 2007 0900 |
| 4 | Drug B 5 mg × 1 | Drug B 5 mg | 5 mg | 1 | Oct. 4, 2007 0900 | Oct. 4, 2007 0900 |
| 5 | Drug B 2.5 mg × 1 | Drug B 2.5 mg | 2.5 mg | 1 | Oct. 5, 2007 0900 | Oct. 5, 2007 0900 |
| 6 | Drug B 1 mg × 1 | Drug B 1 mg | 1 mg | 1 | Oct. 6, 2007 0900 | Oct. 6, 2007 0900 |

To determine the target level on Oct. 1, 2007, medication orders 1, 2, and 3 would be considered. To determine the target level on Oct. 2, 2007, medication orders 2, 3, and 4 would be considered. To determine the target level on Oct. 5, 2007, medication orders 5 and 6 would be considered. Table 2, therefore, also illustrates how varied use rates and ending dates may impact days supply calculations.

In one embodiment, a reorder quantity may be updated before an identified reorder quantity is delivered to a dispensing device. For this example, refer to FIG. 1A and consider an instance when a first medication order is processed by the central server computer system 105. A reorder quantity to bring the supply up to the target level is identified and transmitted (e.g., to a central dispensing unit 115 of FIG. 2). Assume, for purposes of this example, that the items have been dispensed and labeled, but not delivered to the cabinet (e.g., they are still located at the central dispensing unit 115).

A second medication order may then be received before the cabinet 220-*c* is restocked. In certain circumstances, the reorder quantities may be changed before restock by the processing of the second medication order. In one embodiment, if the current supply at the cabinet plus the reorder quantity from the first medication order is below the reorder level, the modified reorder quantity will be identified and transmitted. However, if the current supply at the cabinet plus the reorder quantity from the first medication order is above the reorder level and below the target level, the reorder quantity will not be changed. If the current supply at the cabinet plus the reorder quantity from the first medication order is above the target level, the reorder quantity will be changed and transmitted only if the items to be stocked would not be used by the patient. A number of other reorder scenarios are possible as well. For example, a medication order may be discontinued or the patient discharged after the initial order list has been gathered at a central dispensing unit 115 but before the cabinets are restocked. In this scenario, the restock update may direct a user to remove items for discontinued medication orders and discharged patients from the restock list before proceeding to the cabinets.

Turning to a restock list generated by and received from an external system, there may be certain additional steps in processing such a list. When lists are received from external sources, items and patients may be validated to check whether any subset of the patients or items on the list cannot be handled. Once an external list is so filtered, any of the steps described above may be performed to generate a restocking list of items and quantities to restock.

Figure 15:
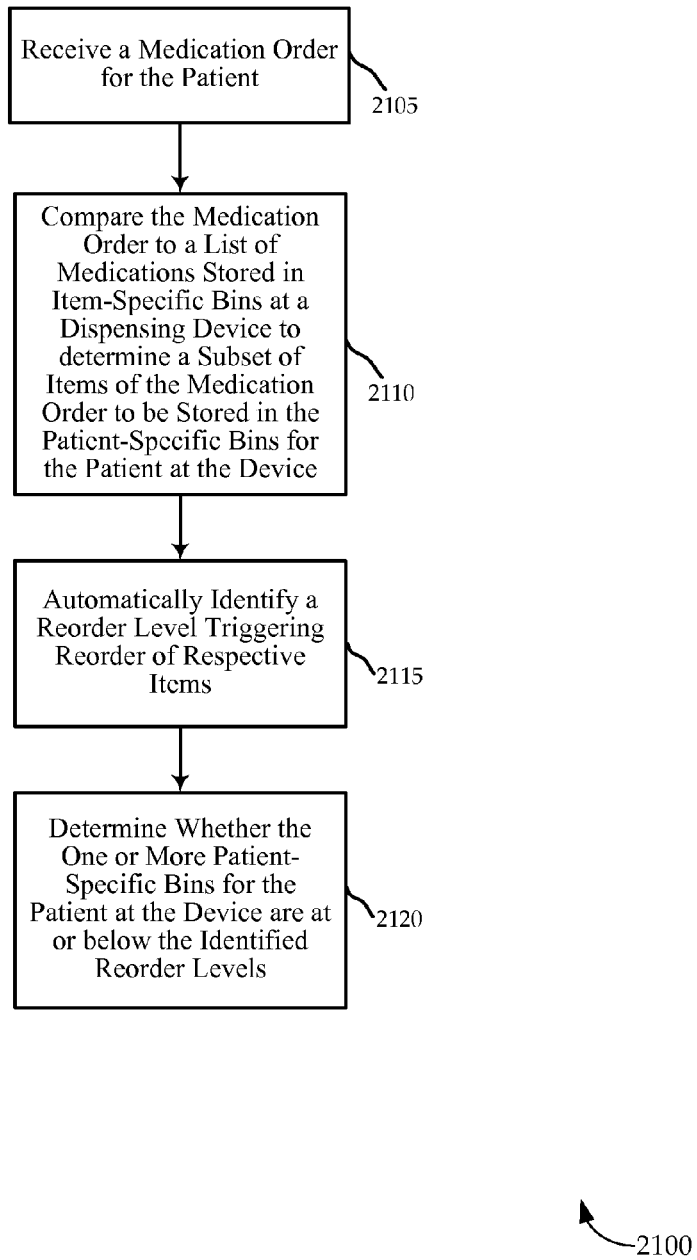
FIG. 15 is a flow diagram illustrating a method of identifying items of a medication order to be reordered for a patient according to various embodiments of the invention.

Referring next to FIG. 15, a flow diagram illustrates an embodiment of a method 2100 of identifying items of a medication order to be reordered for a patient. This method 2100 may, for example, be performed in whole or in part by the central server computer system 105 of FIG. 1A or 2. Alternatively, the method 2100 may be performed in whole or in part by a computer associated with a dispensing device 120 or 220 of FIG. 1A, 1B, or 2.

At block 2105, a medication order is received for the patient. At block 2110, the medication order is compared to a list of medications stored in ISBs at a dispensing device to determine a subset of items of the medication order to be stored in the PSBs for the patient at the device. At block 2115, a reorder level triggering reorder of respective items is automatically identified. At block 2120, a determination is made for the items as to whether the one or more PSBs for the patient at the device are at or below the identified reorder levels.

Figure 16:
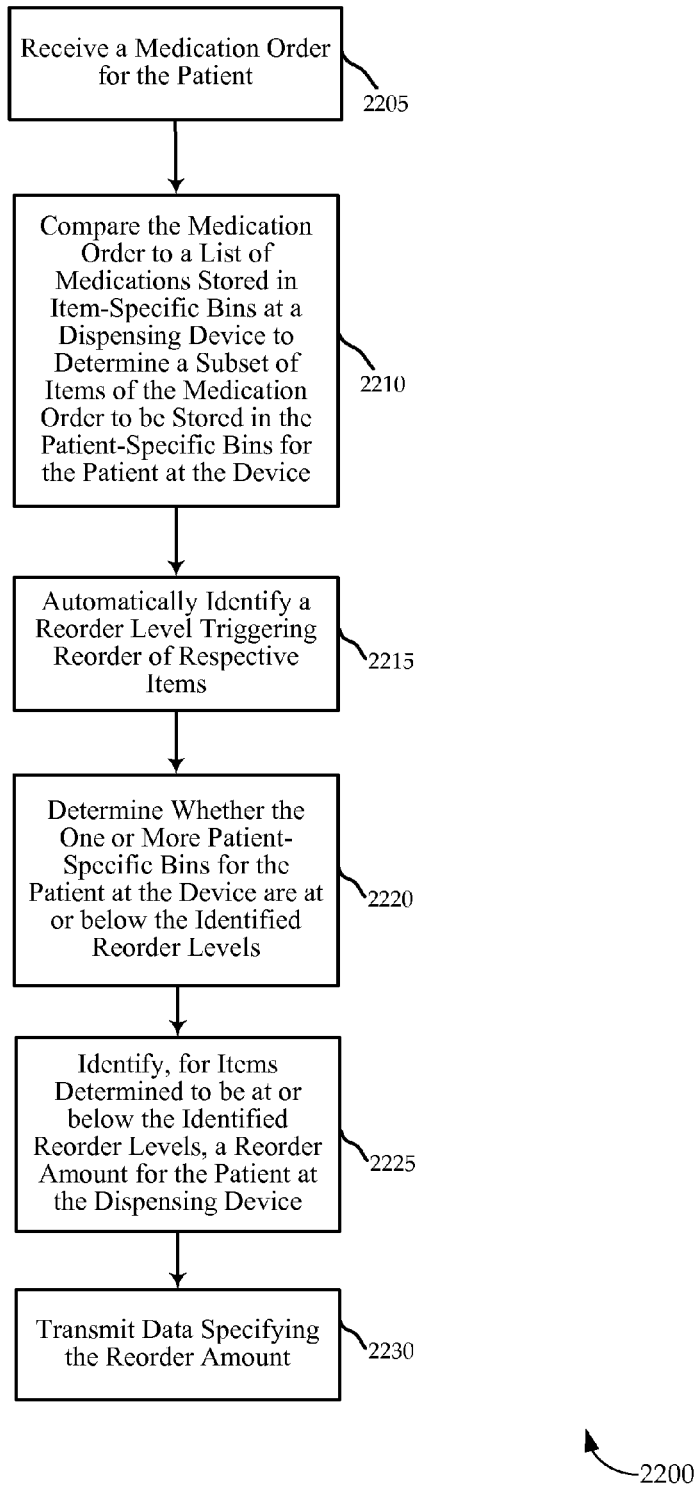
FIG. 16 is a flow diagram illustrating an alternative method of identifying items of a medication order to be reordered for a patient according to various embodiments of the invention.

Referring next to FIG. 16, another embodiment is shown of a method 2200 of identifying items of a medication order to be reordered for a patient. This method 2200 may, for example, be performed in whole or in part by the central server computer system 105, the computer associated with a dispensing device 120 or 220, or any combination thereof.

At block 2205, a medication order is received for the patient (e.g., by a receiving unit of the central server computer system configured to receive data). At block 2210, the medication order is compared to a list of medications stored in ISBs at a dispensing device to determine a subset of items of the medication order to be stored in the PSBs for the patient at the device. At block 2215, a reorder level triggering reorder of respective items is automatically identified. At block 2220, a determination is made for the items as to whether the one or more PSBs for the patient at the device are at or below the identified reorder levels. At block 2225, for items determined to be at or below the identified reorder levels, a reorder amount is determined for the patient at the dispensing device.

At block 2230, data specifying the reorder amount may be transmitted (e.g., by a transmitting unit of the central server computer system). For example, the data specifying the reorder amount may be transmitted to a pharmacy to generate a restocking list, or be transmitted in the form of a restocking list.

Figure 17:
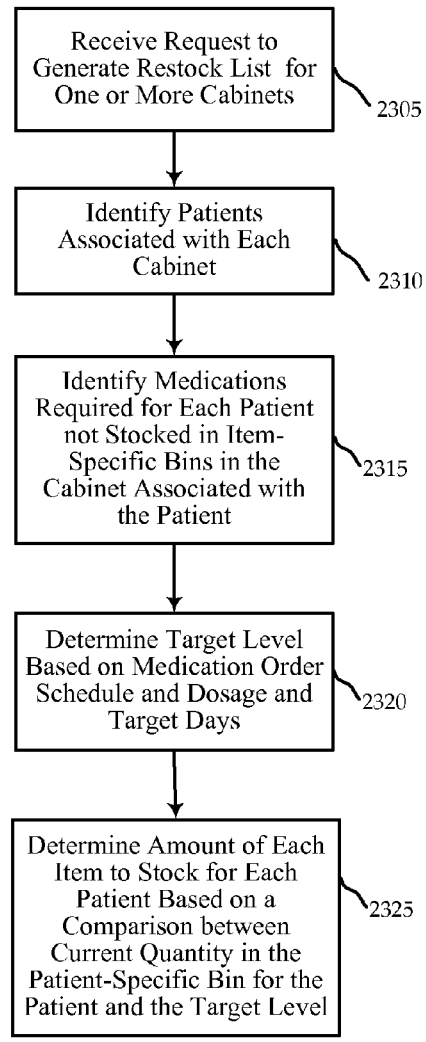
FIG. 17 is a flow diagram illustrating an alternative method of generating a restocking list for one or more cabinets according to various embodiments of the invention.

Referring next to FIG. 17, an embodiment of a method 2300 of generating a restocking list for one or more cabinets is described. This method 2300 may, for example, be performed in whole or in part by the central server computer system 105, the computer associated with a dispensing device 120 or 220, or the central dispensing unit 115. In this embodiment, the dispensing device is a cabinet.

At block 2305, a request is received to generate a restock list for one or more cabinets. At block 2310, patients associated with each cabinet are identified (e.g., using rooms table 210-a). At block 2315, medications are identified which are required for each patient but not stocked in ISBs in the cabinet associated with the patient. At block 2320, a target level for each item is determined based on the schedule and dosage of the medication order and a target days supply. At block 2325, an amount of the items for each patient is determined based on current quantity in the PSB for the patient and the target level.

Figure 18:
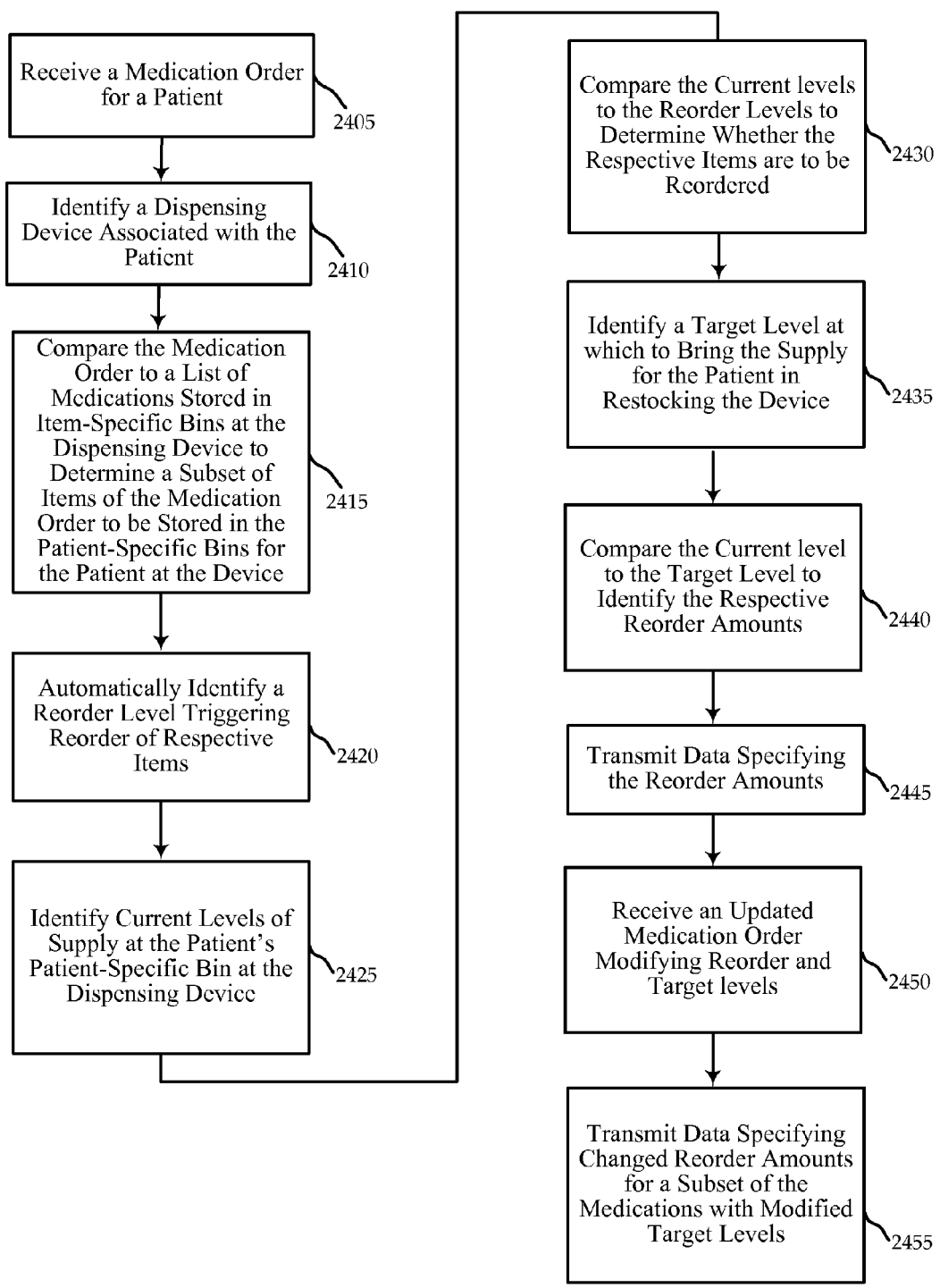
FIG. 18 is a flow diagram illustrating an alternative method of determining reorder amounts according to various embodiments of the invention.

Referring next to FIG. 18, an embodiment of a method 2400 of determining reorder amounts is described. This method 2400 may, for example, be performed in whole or in part by the central server computer system 105, the computer associated with a dispensing device 120 or 220, or any combination thereof.

At block 2405, a medication order is received for the patient. At block 2410, a dispensing device associated with the patient is identified (e.g., based on an association between a room and the dispensing device). At block 2415, the received medication order is compared to a list of medications stored in ISBs at the dispensing device to determine those items of the medication order that are to be stored in the PSBs for the patient at the device.

At block 2420, the reorder levels triggering reorder of respective items is automatically identified. At block 2425, current levels of supply are identified for the respective items at the patient's PSB at the dispensing device (e.g., via transmissions from the device). At block 2430, the current levels are compared to the reorder levels to determine whether each of the respective items is to be reordered At block 2435, a target level is identified, the target level indicating the level to which to bring the supply of each respective item for the patient in restocking the device. At block 2440, the current level is compared to the target level to identify the respective reorder amounts. At block 2445, data is transmitted specifying the reorder amounts. At block 2450, an updated medication order is received (e.g., before the restocking has actually occurred), the order modifying reorder and target levels. At block 2455, data is transmitted specifying changed reorder amounts for only a subset of the medications with modified target levels.

III. Patient-Specific Bin Assignment: Various methods for assigning a PSB in a dispensing device to a patient are described. In one embodiment, a room or area to be occupied by a patient is associated with a dispensing device (e.g., via the rooms table 210-a). One or more available PSBs in the dispensing device are automatically identified when one or more medications are to be stored for the patient. An available PSB in the dispensing device is then be assigned to the patient.

A set of example embodiments will now be described with reference to FIG. 2. It is worth noting, however, that the functions described may be performed by the central server computer system 105 of FIG. 1A or 2, the computer associated with a dispensing device 120 or 220 of FIG. 1A, 1B, or 2, or any combination thereof. The system 200 includes a number of dispensing devices 220 in communication with a central server computer system 105 at a healthcare facility. Each dispensing device 220 may be associated with one or more rooms or areas, and a patient (among a number of patients at the healthcare facility) is assigned to one of the rooms. A particular nursing unit cabinet 220-c is associated with the room assigned to the patient (e.g., via rooms table 210-a). In other embodiments, a range of other types of dispensing devices 120, 220 may be used, configured to dispense medications to areas or other groups of rooms in a healthcare facility.

In one embodiment, the nursing unit cabinet 220-c associated with the patient includes one or more PSBs assigned for exclusive use to a patient, and one or more ISBs each allocated for an item available to be used by the plurality of patients. An ISB is a bin which may be assigned to an item independent of the item's relation to a patient (e.g., it may be for use among two or more patients). The central server computer system 105 may dynamically re-allocate the bins for patient- or item-specific use, or the allocation may be static.

The central server computer system 105 may automatically identify one or more available PSBs from the bins within the cabinet 220-c. To do so, the central server computer system 105 may receive data from the cabinet 220-c, or elsewhere, identifying whether particular PSBs are currently assigned. Thus, the central server computer system 105 or the cabinet 220-c computer may monitor the assignments and usage. The central server computer system 105 may assign one or more of the available PSBs to the patient.

In one embodiment, the assignment of the PSB to the patient is based on a selection from a number of available PSBs by a user through a graphical or other interface at the cabinet 220-c. The central server computer system 105 may transmit a selectable user interface configured to display the identified PSBs, and receive a selection via the selectable user interface (e.g., transmitted from the cabinet 220-c). In an alternative embodiment, an assignment of an available PSB to the patient is made automatically and transmitted to the cabinet 220-c or user.

Once assigned, the central server computer system 105 may be configured to receive information (e.g., transmitted from a cabinet 220-c) indicating that an assigned PSB has insufficient available capacity for the medications to be stored. The system 105 may be configured to automatically identify one or more additional available bins to provide sufficient storage capacity for the identified medications.

In one embodiment, a central server computer system 105 may determine that the cabinet 220-c associated with the room does not currently include one or more available bins allocated as PSBs. In this instance, the system 105 may allocate one or more available bins (e.g., as PSBs based on the determination). Thus, the central server computer system 105 may assign a PSB from this allocation of bins as well.

The central server computer system 105 may receive a listing of medications to be stored for the patient in one or more PSBs (perhaps from a medication order or a restock list). Such a listing may be based on current or future orders. To identify medications of the listing that are to be stored in PSBs, a comparison may be made to a listing of the medications at the cabinet 220-c stored in ISBs (e.g., as common stock). The central server computer system may transmit data identifying medications of the listing to be stored in one or more PSBs.

The central server computer system 105 may determine storage requirements associated with the received listing of items. Storage requirements may include, for example, control level restrictions, user level control access requirements, other physical or technical security requirements, storage type requirements (e.g., refrigeration, the physical configuration, etc.), storage restrictions (e.g., respiratory or other item group restrictions), and storage capacity requirements. The automatic identification of available PSBs may be based on the determined storage requirements (e.g., matching the characteristics of the available PSBs to the storage requirements of the received listing). Thus, in certain embodiments, only those available PSBs meeting certain storage requirements are identified as available.

The central server computer system 105 may also determine whether identified PSBs are eligible to store the particular medications to be stored for the patient, and conversely determine whether the patient is eligible for assignment to the identified available bin. This eligibility may be based on status issues for the patient (e.g., the assignment limitations associated with active, interim, or inactive status). Thus, in certain embodiments, only those available PSBs meeting certain eligibility criteria are identified as available for a patient.

In another embodiment, the central server computer system 105 may determine that the PSBs assigned to the patient in the cabinet 220-c have insufficient available capacity for identified medications. The system may also determine that the cabinet 220-c associated with the room does not currently include an available bin allocated as a PSB and configured with sufficient capacity to store the identified medications. Because of such issues, one or more available bins in the cabinet 220-c may be re-allocated as PSBs. This re-allocation may be based on a determination of sufficient storage capacity at the bin to be re-allocated. In other embodiments, bins may be automatically re-allocated (from ISBs to PSBs, or vice-versa) based on current or future projections for patient-specific storage at the cabinet 220-c or wider group of dispensing devices 220.

When a user is ready to stock a cabinet 220-c, the user may log-in or otherwise register at the cabinet 220-c. Alternatively, a user may initiate an action (e.g., a restock, or a first use of a multi-use item) which requires an identification of a PSB. The central server computer system 105 may then automatically identify an already assigned PSB for storage of medications for the patient, transmitting the identification to the cabinet. Similarly, a computer at the cabinet 220-c may be configured to automatically direct the user, as well.

Figure 19:
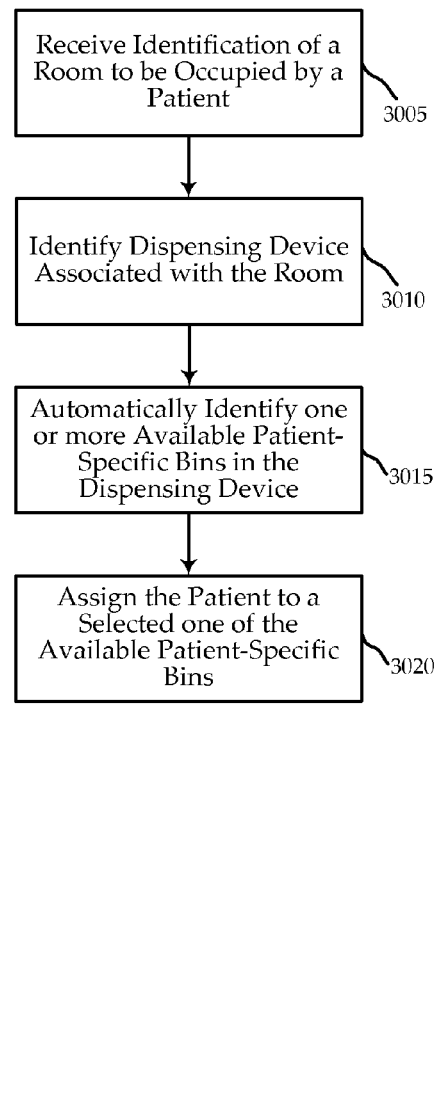
FIG. 19 is a flow diagram illustrating a method of patient-specific bin assignment according to various embodiments of the invention.

Referring next to FIG. 19, one embodiment of a method 3000 of assigning a bin to a patient is illustrated. This method 3000 may, for example, be performed in whole or in part by the central server computer system 105 of FIG. 1A or 2. Alternatively, the method 3000 may, for example, be performed in whole or in part by a computer associated with a dispensing device 120 or 220 of FIG. 1A, 1B, or 2.

At block 3005, identification of a room to be occupied by a patient is received. At block 3010, a dispensing device associated with the room is identified. At block 3015, one or more available PSBs in the dispensing device are automatically identified. At block 3020, the patient is assigned to a selected one of the available PSBs.

Figure 20:
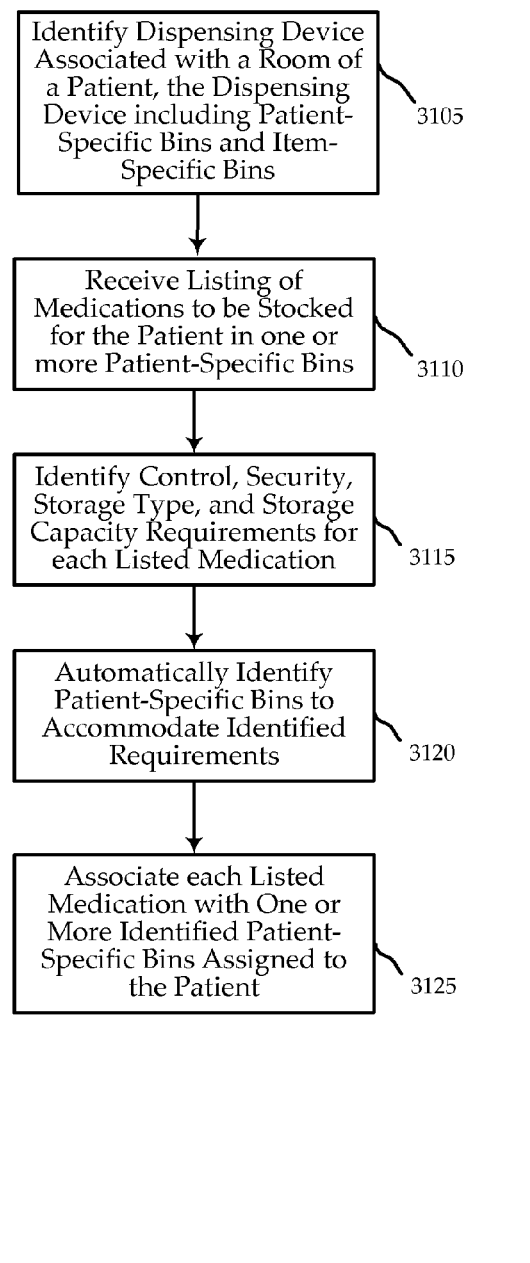
FIG. 20 is a flow diagram illustrating a method of bin assignment according to various embodiments of the invention.

Referring next to FIG. 20, another embodiment of a method 3100 of assigning a bin is illustrated. This method 3100 may, for example, be performed in whole or in part by the central server computer system 105, the computer associated with a dispensing device 120 or 220, or any combination thereof.

At block 3105, a dispensing device associated with a room of a patient is identified, the dispensing device including PSBs and ISBs. At block 3110, a listing of medications to be stocked for the patient in one or more PSBs is received. At block 3115, control, security, storage type, and storage capacity requirements for each listed medication are identified. At block 3120, PSBs able to accommodate the requirements are automatically identified. In some embodiments, only PSBs associated with a given item group may store items from that item group. At block 3125, each listed medication is associated with one or more of the automatically identified PSBs assigned to the patient.

Figure 21:
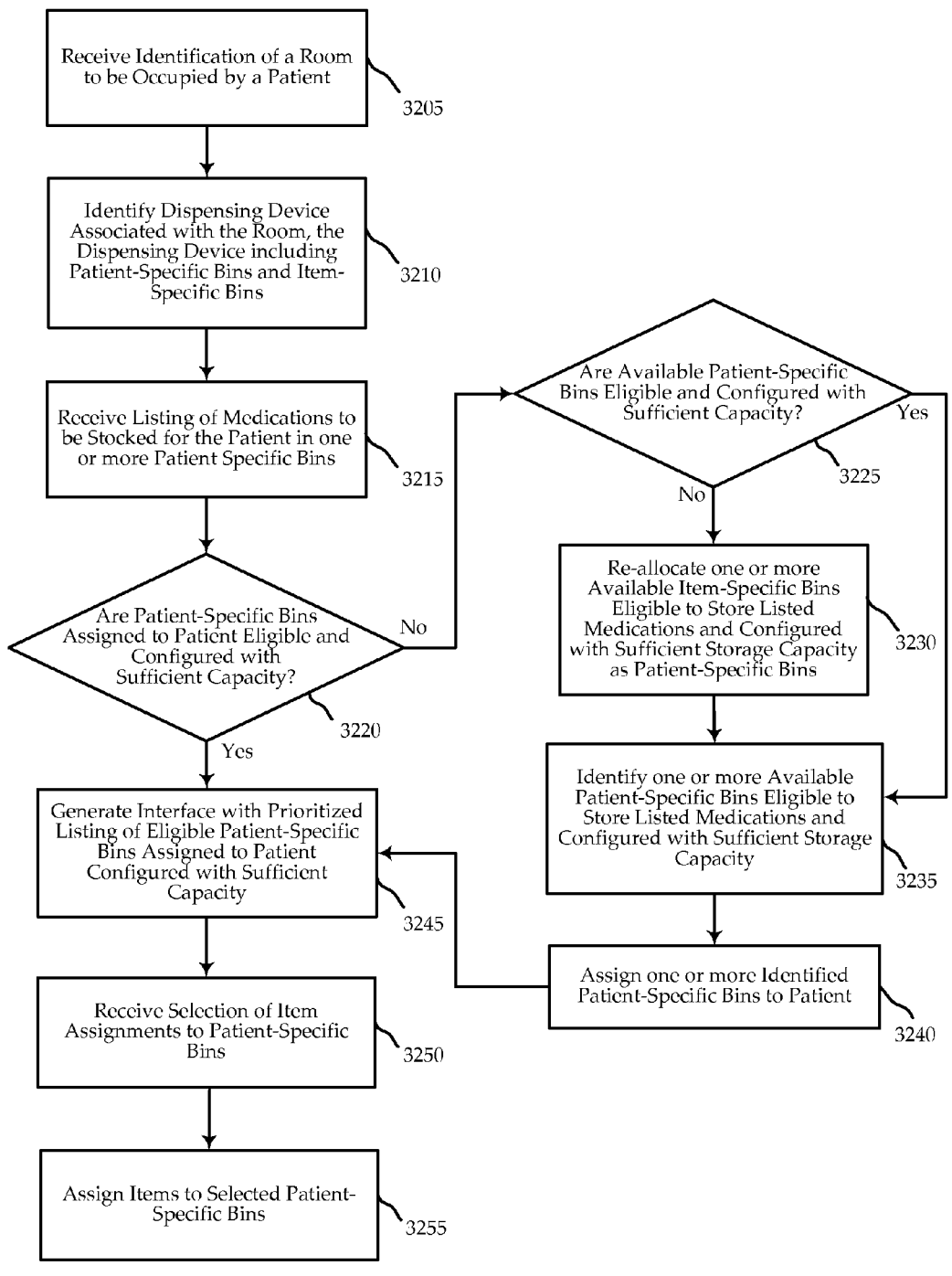
FIG. 21 is a flow diagram illustrating an alternative method of patient-specific bin assignment according to various embodiments of the invention.

Turning to FIG. 21, an alternative embodiment of a method 3200 of assigning a PSB is illustrated. This method 3200 may, for example, be performed in whole or in part by the central server computer system 105, the computer associated with a dispensing device 120 or 220, or any combination thereof.

At block 3205, identification of a room to be occupied by a patient is received. At block 3210, a dispensing device associated with the room is identified, the dispensing device including PSBs and ISBs. At block 3215, a listing of medications to be stocked for the patient in one or more PSBs is received. At block 3220, a determination is made as to whether PSBs currently assigned to the patient are eligible to store one or more items of the listing and also are configured with sufficient storage capacity. If so, the process jumps to block 3245 to generate an interface with a prioritized listing of one or more PSBs assigned to a patient which are both eligible and configured with sufficient capacity.

If the PSBs currently assigned to the patient are insufficient, a determination is made at block 3225 as to whether there are available PSBs both eligible to store the listed items and configured with sufficient capacity. If no such bins are available, the process continues at block 3230, where one or more available ISBs eligible to store listed medications and configured with sufficient storage capacity are re-allocated as PSBs (or, in another embodiment, empty PSBs assigned to other patients may be identified and converted to available PSBs). From either block 3225 or block 3230, the process continues at block 3235, wherein one or more of the available PSBs are identified as eligible to store listed medications and configured with sufficient storage capacity. At block 3240, at least one of the PSBs identified at block 3235 is automatically assigned to the patient. From block 3240, the process advances to block 3245 to generate an interface with prioritized listing of one or more eligible PSBs assigned to the patient configured with sufficient capacity.

From block 3245 (regardless of the manner in which it was reached), the method proceeds to block 3250, where a selection of item assignments to PSBs is received via the interface. At block 3255, items are assigned to selected PSBs. In other embodiments, the selection and assignment of items to PSBs may be automatic.

Figure 22:
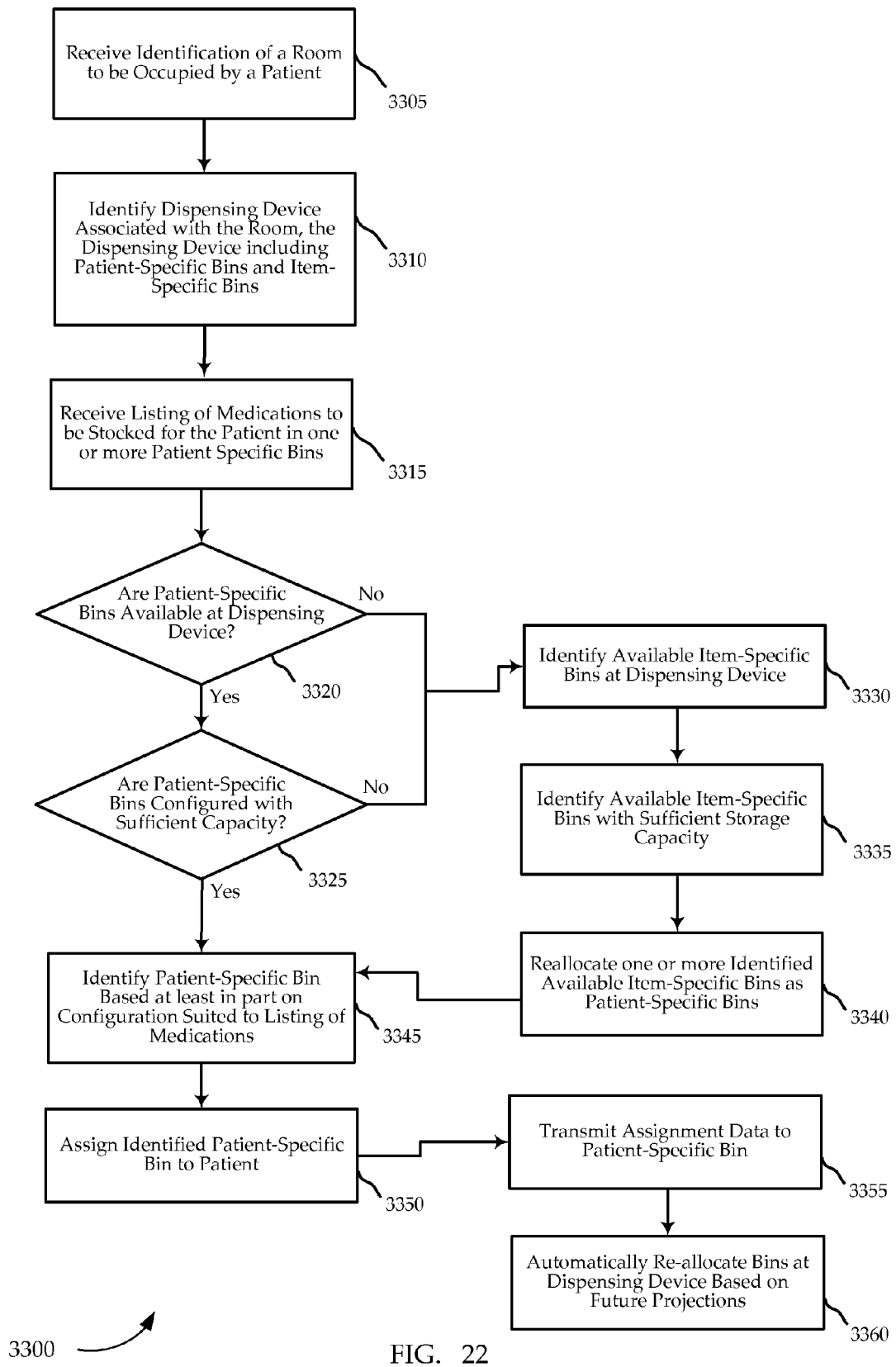
FIG. 22 is a flow diagram illustrating a method of identifying bins for patient-specific bin assignment according to various embodiments of the invention.

Referring next to FIG. 22, an embodiment of a method 3300 of assigning a PSB is illustrated. As above, the method 3300 may, for example, be performed in whole or in part by the central server computer system 105, the computer associated with a dispensing device 120 or 220, or any combination thereof.

At block 3305, an identification of a room to be occupied by a patient is received. At block 3310, a dispensing device associated with a room of the patient is identified, the dispensing device including PSBs and ISBs. At block 3315, a listing of medications to be stocked for the patient in one or more PSBs is received.

At block 3320, a determination is made whether PSBs are available at the dispensing device. If so, at block 3325 a determination is made whether PSBs are configured with sufficient capacity. If so, at block 3345, PSBs are identified, the identification prioritizing a configuration better suited to store the items of the listing of medications.

If no PSBs (e.g., either assigned or unassigned) are available, or if those available are configured with insufficient capacity, available ISBs are identified at the dispensing device at block 3330. At block 3335, those available ISBs with sufficient storage capacity are identified. At block 3340, one or more identified available ISBs are allocated for use as PSBs. From block 3340, one of the newly allocated PSBs is identified at block 3345, the identification prioritizing a configuration better suited to listing of medications.

From block 3345 (regardless of the manner in which it was reached), the PSB is assigned to the patient at block 3350. At block 3355, the assignment information is transmitted to the PSB. At block 3360, bins at the dispensing device are automatically re-allocated based on future projections (e.g., projections based on estimated future use).

IV. Management of Patient Transfers: There are various systems, methods and device configurations for managing the location of medications associated with the transfer of a patient to a new location. The functions described related to managing such a transfer may be performed by the central server computer system 105 of FIG. 1A or 2, the computer of dispensing device 120 or 220 of FIG. 1A. 1B, or 2, or a combination thereof. The steps may be performed by the computer of the dispensing device 120 or 220 associated with the originating or terminating location.

In one embodiment, the process is initiated when information is received indicating that the patient is to be transferred from a current room served by a first cabinet to a new room served by a second cabinet. An identification is made of medications assigned to the patient that are stored at the first cabinet and are to be transferred. The bin configuration for such medications at the first cabinet is identified and stored. The stored bin configuration data may then be applied to the second cabinet for bin assignment purposes (the second cabinet inheriting one or more PSB attributes from the first cabinet), and thereby leveraging the tuning performed at the first cabinet.

In one embodiment, the process is triggered when information is received (e.g., at the central server computer system 105) that a patient is to be transferred to a new room or area served by a different dispensing device 120. This may be a patient transfer that has occurred in the past, will occur in the future, or is currently in process (e.g., when a patient is en route). Particular components may, but need not, possess real-time data regarding the physical location of the patient. By way of example, a central server computer system 105 may receive a set of data which is generated as notice of a transfer (e.g., automatically created by user action at a dispensing device 120 and transmitted to the central server computer system 105).

The central server computer system 105 may identify medications stored in the one or more PSBs assigned to the patient at the originating dispensing device, and store a set of data identifying the bin configuration. To perform this identification, the central server computer system 105 may automatically identify (e.g., in response to a transfer notification) medications to be transferred from the first originating device to the destination dispensing device for the patient. The bin configuration data may be limited to bins storing medications to be transferred. The central server computer system 105 may also automatically identify discontinued medications for the patient, which may be removed and returned. The bins containing only discontinued items may be excluded from the stored bin configuration data.

This bin configuration data may include characteristics of each PSB storing the identified items (bin type, bin size, bin location, security, etc.). It may include a list of the items stored in respective PSBs, characteristics of each item stored (amount, control level, security requirements, refrigeration requirement, storage needs, etc.), and any other capacity utilization data (e.g., proportion of capacity used). The bin configuration data may be collected by accessing or otherwise auditing information on the patient or dispensing device in data store 110 or a central dispensing unit 115 (e.g., accessing an active or future medication order). As addressed above, identification and bin configuration may be initiated by the receipt of the transfer notification, or may otherwise occur before or after receipt of the transfer notice. In one embodiment, the change of status of a bin (e.g., from active to interim) may trigger the identification of medications and the storage of bin configuration data before or after actual patient transfer.

The bin configuration may then be applied to the dispensing device associated with transfer location, so that tuning performed at the originating location may be transferred. For example, the central server computer system 105 may be configured to apply the stored set of bin configuration data by automatically identifying a bin configuration for the second dispensing device based on the configuration of certain PSBs assigned to the patient at the originating dispensing device. All, or only part, of the bin configuration data may be used in assigning bins at the dispensing device at the transfer location. For example, items in different PSBs at the originating device may be combined into a single bin at the transfer location, while items with different control levels may be placed in separate bins. Thus, the original PSB configuration may be leveraged to varying degrees, as it may be identical, have only certain parts mirrored, or only have aspects used in a more limited manner.

There are a number of factors in determining how bin configuration data is applied to the destination dispensing device 120. The destination device 120 may have a different configuration, so in some instances only certain aspects of the original bin configuration may be transferable. The destination device 120 may already be storing medications in locations that prevent or inhibit identical configurations from being used. In some instances, bins may be re-allocated (e.g., from ISBs or other bin types) to PSBs to allow aspects of the originating bin configuration to be applied to the destination device 120, or for other purposes.

In one embodiment, the proportion of capacity used for certain bins or sets of bins at the originating device 120 may be determined. The application of the bin configuration data to the destination device 120 may be limited to only those bins or sets of bins using greater than a certain proportion of capacity (e.g., only apply bins over 50% full, and consolidate remaining medications). Thus, there may be rules providing that only bins filled over a threshold proportion of capacity are applied to the second dispensing device. The preceding embodiments only represent examples of the different extent to which tuning may be leveraged.

The listing of medications to be transferred and the configuration data may be transmitted (e.g., by the central server computer system 105) to the destination dispensing device 120. The transmitted configuration data may identify specific bins for storage of each of the items from the listing of medications. The destination device 120 may be a PSB which inherits certain attributes of the originating dispensing device, or may be a non-PSB cabinet which uses the information in another manner (e.g., to identify storage needs).

It is also worth noting that bin configuration data may be applied to other devices in addition to the destination device 120. For example, consider an example in which medications are identified which are to be stored in a different dispensing device. If all or part of these medications are similar to the medications stored in the originating device 120 (e.g., have greater than a threshold correlation with medications stored for the patient in that device), the stored bin configuration data from the originating device 120 may be applied to the different dispensing device. In this way, tuning performed on certain medications may be leveraged beyond the destination device 120.

Figure 23:
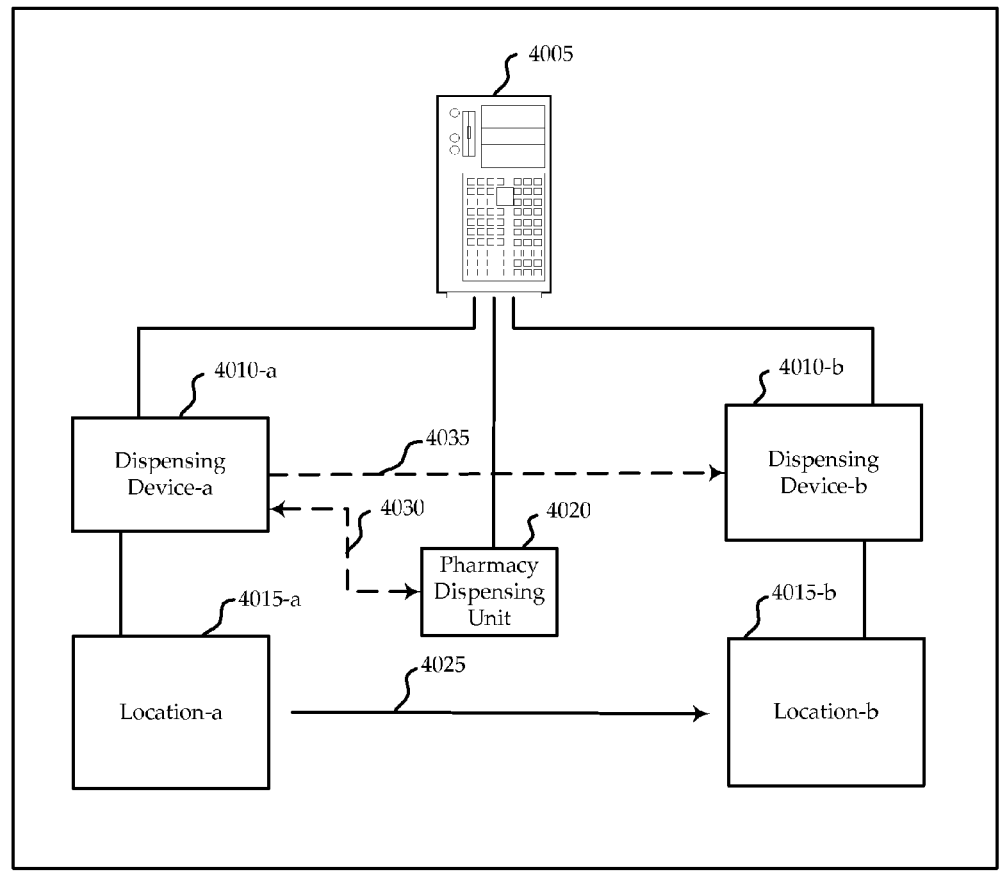
FIG. 23 is a block diagram illustrating a system for managing medications during a patient transfer between rooms served by different dispensing devices according to various embodiments of the invention.

Turning to FIG. 23, an example of a system 4000 is illustrated for managing medications during a patient transfer between rooms served by different dispensing devices. The illustrated system 4000 includes two dispensing devices, dispensing device-a 4010-$a$ and dispensing device-b 4010-$b$. Each device may, for example, be a dispensing device 120 or 220 of FIG. 1A, 1B, or 2, and thus may be a cabinet with a number of bins for dispensing medical supplies (e.g., pharmaceuticals, other medications, or other supplies for a patient at a healthcare facility). For purposes of example, assume that the items to be transferred are medications.

The system 4000 also includes a central server computer system 4005, which is communicatively connected with each dispensing device 4010. The central server computer system 4005 may be the central server computer system 105 of FIG. 1A or 2. The system also includes a pharmacy dispensing unit 4020, which may be the central dispensing unit 115 of FIG. 1A, 1B, or 2. The pharmacy dispensing unit 4020 is also communicatively connected to the central server computer system 4005. The system may include any other number of connected dispensing devices (not shown), and thus the illustrated embodiment is for purposes of example only. Moreover, the following illustrates functionality for purposes of example only, and many other scenarios are possible.

Dispensing device-a 4010-$a$ may be associated with location-a 4015-$a$. This association may indicate that dispensing device-a 4010-$a$ is a cabinet at a nursing station serving a set of rooms which includes location-a 4015-$a$. Assume that in this example, a patient at the healthcare facility is initially located in a room within location-a 4015-$a$, and the central server computer system 4005 may reflect this association. However, in other embodiments, location-a 4015-$a$ may be a past or future location for the patient, or be another type of room or location (e.g., an operating room, an emergency room, a transitory location between two rooms, etc.).

A medication order may be generated for the patient and routed to the pharmacy dispensing unit 4020. The medications specified in the order may then be placed in a cart at the pharmacy dispensing unit 4020 for delivery 4030 to dispensing device-a 4010-$a$. Medication is then stocked and/or restocked for the patient in one or more PSBs at dispensing device-a 4010-$a$.

The patient is then scheduled to be transferred 4025 from location-a 4015-$a$ to location-b 4015-$b$. Either before, during, or after the physical transfer of the patient and/or the transfer of certain medications, bin configuration data is stored for PSBs of the patient at dispensing device-a 4010-$a$. The bin configuration information may be limited to PSBs holding medications to be transferred, and perhaps meeting other criteria (as noted above). At least some medications stored in PSBs at dispensing device-a 4010-$a$ are transferred 4035 to a new dispensing device associated with the new location (more specifically, dispensing device-b 4010-$b$ associated with the transfer room at location-b 4015-$b$).

The bin configuration data from dispensing device-a 4010-$a$ may then be applied, to differing degrees, in assigning PSBs to hold the transferred medications at dispensing device-b 4010-$b$. The tuning performed at dispensing device-a 4010-$a$ may be analyzed to determine which aspects should be applied at dispensing device-b 4010-$b$. As discussed above, bin configuration may be mirrored or have only certain aspects applied.

An example of the bin configuration data that may be stored and analyzed is illustrated in FIG. 24. In this embodiment, the bin configuration data is stored as a table 4100. The bin configuration data may be stored by and/or transmitted to or from the central server computer system 105 of FIG. 1A or 2 or the computer of dispensing device 120 or 220 of FIG. 1A, 1B, or 2.

The bin configuration data includes information regarding bin type 4105, bin storage space 4110, bin security 4115, and bin location in cabinet 4120. Other embodiments may include more or fewer bin characteristics. The bin configuration data may also include the types of medications stored 4125, the amount 4130, and the security requirements 4135. In other embodiments, more or fewer medication characteristics may be included. Capacity utilization information 4140 may also be included for each, or for a set, of bins.

Figure 25:
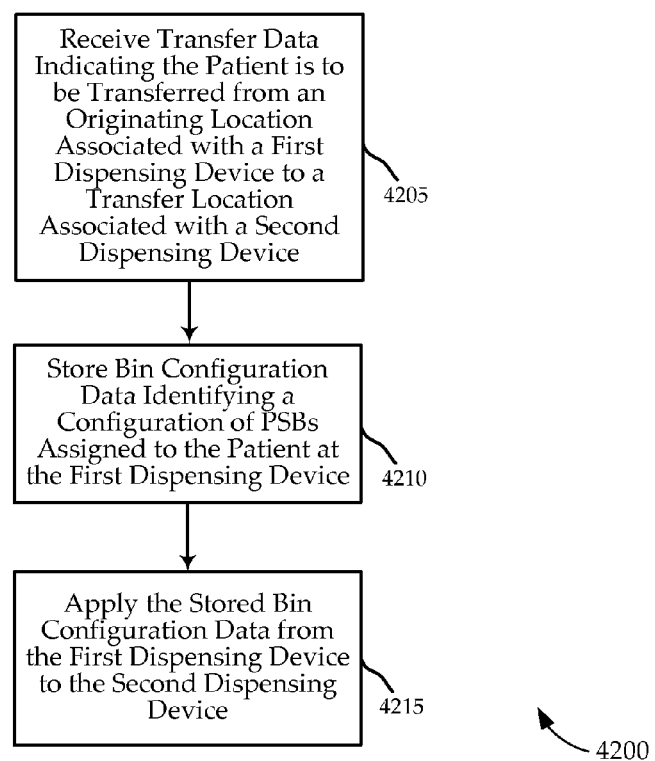
FIG. 25 is a flow diagram illustrating a method of managing a patient transfers according to various embodiments of the invention.

Referring next to FIG. 25, one embodiment of a method 4200 of managing a patient transfer is illustrated. This method 4200 may, for example, be performed in whole or in part by the central server computer system 105, the computer associated with a dispensing device 120, or 220, or any combination thereof. Also, it is worth noting that in this and in other embodiments, various steps may be excluded, and the order may be rearranged.

At block 4205, transfer data is received indicating that a patient is to be transferred from an originating location associated with a first dispensing device to a transfer location associated with a second dispensing device. At block 4210, bin configuration data is stored identifying a configuration of PSBs assigned to the patient at the first dispensing device. At block 4215, the stored bin configuration data from the first dispensing device is applied to the second dispensing device.

Figure 26:
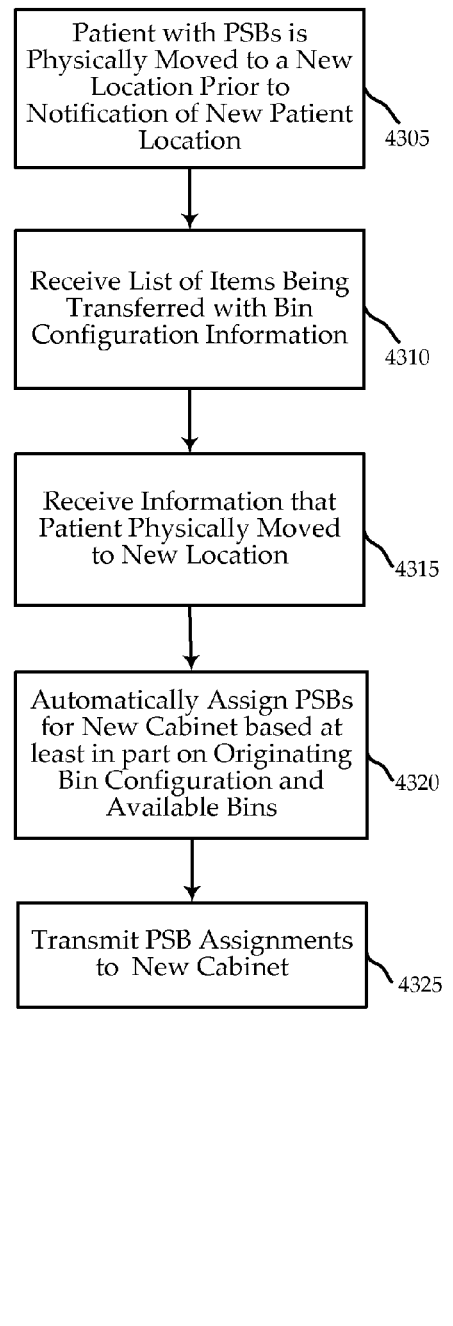
FIG. 26 is a flow diagram illustrating a method of assigning patient-specific bins at a dispensing device associated with the transfer destination for a patient according to various embodiments of the invention.

Referring next to FIG. 26, an example of a method 4300 of assigning PSBs at a dispensing device associated with the transfer destination for a patient is shown. In this embodiment, the dispensing device is a cabinet. This method 4300 may, for example, be performed in whole or in part by the central server computer system 105, the computer associated with a dispensing device 120 or 220, or any combination thereof.

At block 4305, a patient with assigned PSBs is physically moved to a new location prior to notification of new patient location. The assigned PSBs may be at the cabinet associated with the patient's previous location and, thus, that cabinet may remain as the currently active cabinet even after the patient has physically been moved. At block 4310, the bin configuration at the cabinet associated with the patient's previous location may be received (e.g., by the central server computer system 105 from the currently active cabinet). This bin configuration information may include the list of items to be transferred.

At block 4315, information is received that the patient has physically moved to a new location. The new location may be identified with the received information. At block 4320, PSBs for a new cabinet associated with the new location are automatically assigned, based at least in part on the received bin configuration and available bins at the new cabinet. In this manner, the received bin configuration information may be applied to the new cabinet. At block 4325, the PSB assignments are transmitted to the new cabinet.

Figure 27:
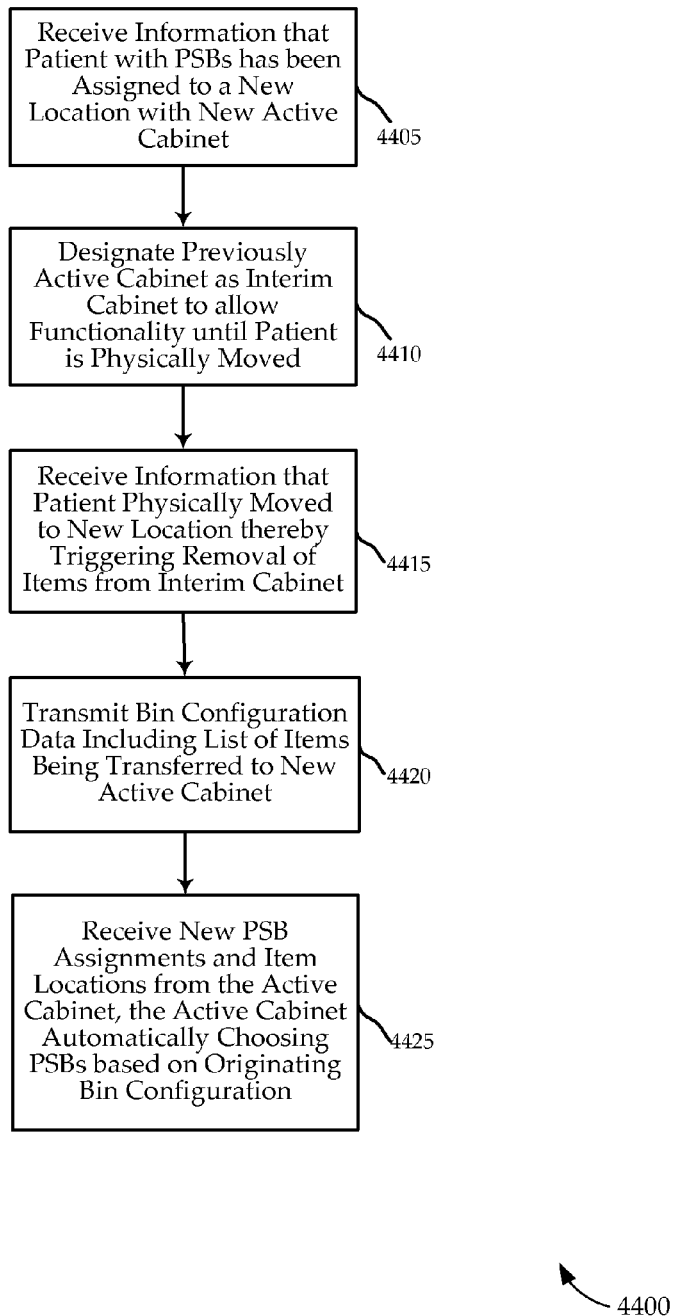
FIG. 27 is a flow diagram illustrating an alternative method of assigning patient-specific bins at a dispensing device associated with the transfer destination for a patient according to various embodiments of the invention.

Referring next to FIG. 27, an example of an alternative method 4400 of assigning PSBs at a dispensing device associated with the transfer destination for a patient is shown. In this embodiment, the dispensing device is again a cabinet. This method 4400 may, for example, be performed by the central server computer system 105, a computer of dispensing device 120 or 220, or any combination thereof.

At block 4405, information is received that a patient with PSBs has been assigned to a new location before a physical move to a new location. The assigned PSBs may be at the cabinet associated with the patient's current, but temporary, location. This may be any form of notification of a transfer. The cabinet associated with the new location may thereby become the active cabinet, despite the fact that the patient has yet to depart from his current location.

At block 4410, the previously active cabinet (e.g., associated with the location where patient and his or her PSBs are located) is designated as the interim cabinet to allow continued functionality until the patient is physically moved. At block 4415, information is received that the patient has physically moved to the new location, triggering removal of items from the interim cabinet. Upon removal, inactive items may be identified (perhaps by the central server computer system 105) and returned (e.g., to a pharmacy or return bin). The list of items to be transferred may be maintained by the central server computer system 105, or received from the interim cabinet (which may then become inactive).

At block 4420, the bin configuration information (including the list of items being transferred) is transmitted to the newly active cabinet (e.g., by the central server computer system 105). This active cabinet computer may assign PSBs to the patient and direct placement of the items automatically based on the originating bin configuration. In this manner, the bin configuration information may be applied to the new cabinet by the computer at the active cabinet. At block 4425, the new PSB assignments and item locations are received (e.g., by the central server computer 105) from the active cabinet.

Figure 28:
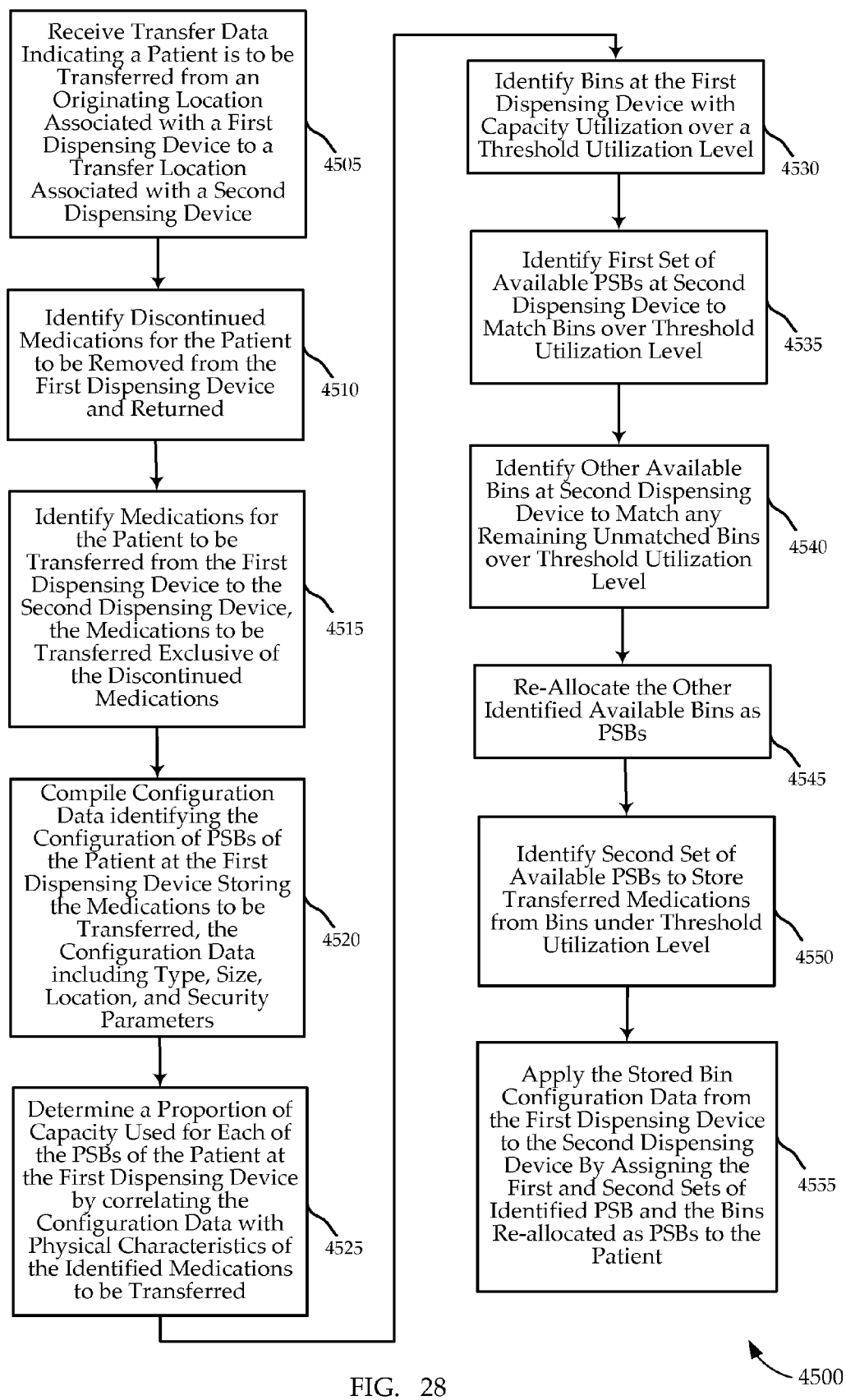
FIG. 28 is a flow diagram illustrating a method of applying bin configuration data to a dispensing device associated with the transfer destination for a patient according to various embodiments of the invention.

Referring next to FIG. 28, an example of an alternative method 4500 of applying bin configuration data to a dispensing device associated with the transfer destination for a patient is shown. In this embodiment, the dispensing device is again a cabinet. This method 4500 may, for example, be performed by the central server computer system 105, a computer of dispensing device 120 or 220, or any combination thereof.

At block 4505, transfer data is received indicating that a patient is to be transferred (in the past, or in the future) from an originating location associated with a first dispensing device to a transfer location associated with a second dispensing device. At block 4510, discontinued medications for the patient to be removed from the first dispensing device are identified. This may be done by comparing the active medication order to the listing of medications stored in the PSBs to identify medications that are discontinued. At block 4515, medications for the patient to be transferred from the first dispensing device to the second dispensing device are identified, the medications to be transferred exclusive of the discontinued medications.

At block 4520, bin configuration data is compiled identifying the configuration of the PSBs of the patient at the first dispensing device storing the medications to be transferred, the configuration data including type, size, location, and security parameters. This compilation may be performed by auditing a record (e.g., the bins table 210-*b* and/or items table 210-*c*) of medications to be transferred and the PSBs storing such medications. At block 4525, the proportion of capacity used for each of the patient's PSBs at the first dispensing device is determined by correlating the configuration data with physical characteristics of the identified medications (or container thereof) to be transferred. The capacity utilization may be determined by analyzing the bin size in light of the physical dimensions of the medicine(s) and/or container(s) stored therein.

At block 4530, those bins of the patient at the first dispensing device with capacity utilization over a threshold utilization level are identified (e.g., useable space utilization above 70%). At block 4535, a first set of available PSBs at the second dispensing device is identified which matches bins over the threshold utilization level. However, in this embodiment assume that there are not enough available PSBs of proper sizes/characteristics to match all of the bins from the first dispensing device that are above the threshold utilization level.

Therefore, at block 4540, other available bins (e.g., available ISBs, or PSBs currently assigned to a patient and not in use) at the second dispensing device are identified that match any remaining unmatched bins over the threshold utilization level. At block 4545, the other identified available bins at the second dispensing device are re-allocated as available PSBs. At block 4550, a second set of available PSBs at the second device is identified to store transferred medications from the bins at the first dispensing device under threshold utilization level. At block 4555, the stored bin configuration data from the first dispensing device is applied to the second dispensing device by assigning the first and second sets of identified PSBs and the bins re-allocated as PSBs to the patient.

V. Removal or Return of Items Associated with a Patient-Specific Bin: In other embodiments, functionality is described for the removal and return of medications that has been allocated or assigned to specific patients. Various procedures are set forth for the removal of items from PSBs. Also, procedures are described for the return of items which are prepared and ready to be stocked or restocked in PSBs (e.g., medications in a cart ready to be placed in a PSB). The removal and return of such medications may be referred to as a cleanup.

In certain embodiments, items are removed or returned to a central dispensing unit (e.g., a pharmacy) because there is a discontinued or otherwise changed medication order, or surplus medication in a PSB. The removal or return may also be initiated by a transfer or discharge. The cleanup functionality described herein may be performed by the central server computer system 105 of FIG. 1A or 2, a dispensing device 120 or 220 computer of FIG. 1A, 1B, or 2, or a combination thereof.

There are a variety of actions that may trigger a cleanup. For example, a cleanup may be triggered by an input request of a user to stock or restock a patient's PSBs at a dispensing device 120. The attempt by a user to transfer items to a new active dispensing device 120 may also trigger cleanup at the originating or transfer location. A notification that a patient will be soon be discharged, or an attempt to return a patient's own medicine to a patient upon discharge, may trigger cleanup. A change to a medication order (e.g., discontinuing a medication or changing a dose) may do so, as well. A cleanup may be triggered as part of a regularly scheduled cleanup. The central server computer system 105 or dispensing device 120 computer may be configured to have a variety of other actions trigger a cleanup, as well.

By way of example, a central server computer system 105 may receive a set of data which is generated as notice of a triggering event for a patient (e.g., automatically created by user action at a dispensing device 120 and transmitted to the central server computer system 105). The central server computer system 105 may identify medications stored in the one or more PSBs assigned to the patient (or medications in possession of a user to be stocked or restocked therein), and may also identify a medication order associated with the patient. These identifications may, for example, be made by accessing information on the patient or dispensing device in data store 110 or a central dispensing unit 115. The identifications may be initiated by the receipt of the triggering data, or may occur before receipt of the triggering data.

When a cleanup is triggered, a determination may be made whether the patient is to be discharged. If so, the medications and other supplies of the patient stored in the PSBs may be identified, and their removal destinations specified (e.g., return to pharmacy, return to patient, etc.). A determination may also be made whether the patient is to be transferred within the healthcare facility. If so, items stored in the PSBs without an active medication order (e.g., discontinued medications) may be identified along with a removal destination. This identification may be performed by comparing the list of items stored in a PSB for the patient to a medication order. The remaining items to be transferred, and the current bin configuration, may be stored and/or transmitted (e.g., transmitted to the new dispensing device).

The central server computer system 105 may determine that a patient is not to be transferred or discharged (e.g., determining that the patient is remaining at the healthcare facility because no notice of discharge is currently associated with the patient). Absent discharge or transfer, cleanup may be triggered during the stocking, restocking, or periodic cleaning of the PSB for a particular patient, set of patients, or cabinet generally. In any case, the items in PSBs that have been discontinued, and other surplus items, may be identified, along with a removal destination. Similarly, items in a cart to be stocked or restocked at a dispensing device 120 may be identified and rerouted because they have been discontinued or there is a surplus. These identifications of discontinued or surplus items may be performed by comparing the list of items stored in a PSB for the patient to a medication order.

Thus, the central server computer system 105 may automatically identify, in response to the received set of triggering data, a subset of the medications stored in PSBs that have been discontinued according to the medication order. Thus, the discontinued medications already stored in the dispensing device 120, or currently set to be stocked or restocked at the device, may be identified. Similarly, if an item is oversupplied (e.g., because of a change in a medication order), the amount of oversupply may be identified, and a user may be directed to remove some of the items.

The central server computer system 105 may also identify return locations for discontinued medications (e.g., by accessing a set of rules stored in the data stores 110 regarding appropriate return locations). The central server computer system 105 may also transmit, to a dispensing device associated with the patient, data directing removal or return of the medications and identifying the return locations.

For each item removed and/or returned, the central server computer system 105 may be configured to automatically track the item, assembling the information and storing it in the data stores 110. The central server computer system 105 may receive information that a particular item has arrived at a particular destination (e.g., an identifier for the item may be read at the transfer, return, pharmacy, or other location, and transmitted to the central server computer system 105). Items removed during cleanup may be tracked in an ongoing manner, or this information may be assembled periodically. Thus, removed items which have not reached their destinations may be tracked in real time or periodically.

Figure 29:
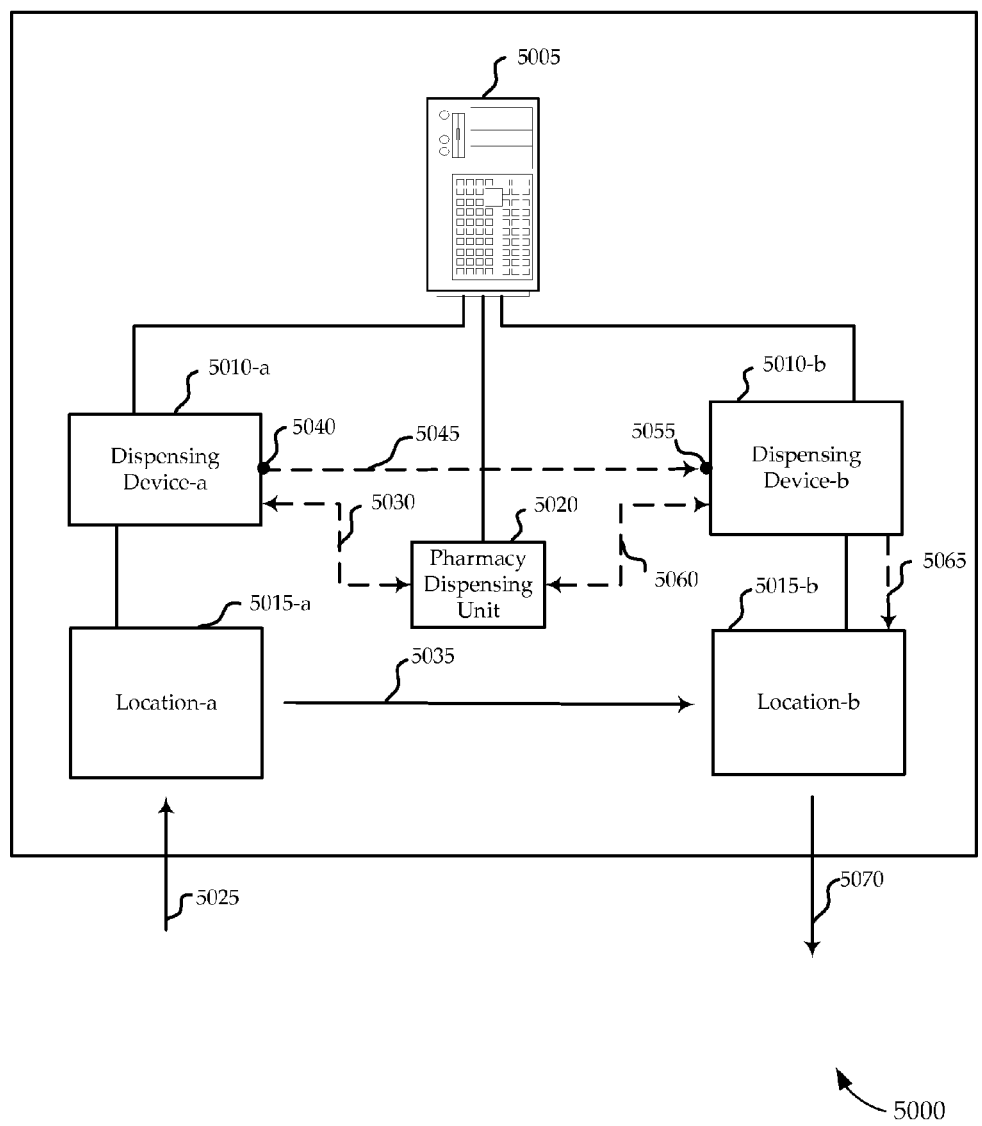
FIG. 29 is a block diagram illustrating a system for removing and/or returning medications stored or ready to be stored in a dispensing device which includes patient-specific bins according to various embodiments of the invention.

Turning to FIG. 29, an example of a system 5000 is illustrated for removing and/or returning medications stored (or ready to be stored) in a dispensing device which includes PSBs. The illustrated system 5000 includes two dispensing devices, dispensing device-a 5010-*a* and dispensing device-b 5010-*b*. Each device may, for example, be a dispensing device 120, 220 of FIG. 1A, 1B, or 2, and thus may be a cabinet with a number of bins for dispensing medical supplies (e.g., pharmaceuticals, other medications, or other supplies for a patient at a healthcare facility). For purposes of example, assume that the items to be removed and/or returned are medications.

The system 5000 also includes a central server computer system 5005, which is communicatively connected with each dispensing device 5010. The central server computer system 5005 may be the central server computer system 105 of FIG. 1A, 1B, or 2. The system also includes a pharmacy dispensing unit 5020, which may be the central dispensing unit 115 of FIG. 1A, 1B, or 2. The pharmacy dispensing unit 5020 is also communicatively connected to the central server computer system 5005. The system may include any other number of connected dispensing devices (not shown), and thus the illustrated embodiment is for purposes of example only. Moreover, the following illustrates functionality for purposes of example only, and many other scenarios are possible.

Dispensing device-a 5010-*a* may be associated with location-a 5015-*a*. This association may indicate that dispensing device-a 5010-*a* is a cabinet at a nursing station serving a set of rooms which include location-a 5015-*a*. Assume that in this example, a patient arrives at the healthcare facility, and is physically moved 5025 into one of the rooms of location-a 5015-*a*, and the central server computer system 5005 may reflect this association. However, in other embodiments, location-a 5015-*a* may be a past or future location for the patient, or be another type of room or location (e.g., an operating room, emergency room, a transitory location between two rooms, etc.).

At some time after arrival of the patient at location-a 5105-*a*, a patient's own medication may be stocked for the patient in a PSB at dispensing device-a 5010-*a*. A medication order or orders may be generated for the patient, and routed to the pharmacy dispensing unit 5020. The medication or medications specified in the order(s) may then be placed in a cart at the pharmacy dispensing unit 5020 for delivery 5030 to dispensing device-a 5010-*a*. A medication order then changes while the medications are en route, discontinuing certain medications (e.g., medication order may be discontinued, or a subset of items therein may be discontinued). When a user attempts to stock the device, the cleanup is triggered, and the discontinued medications being delivered are instead identified for return (e.g., return 5030 to the pharmacy dispensing unit 5020).

While the patient remains at location-a, a new medication order is generated for the patient, and routed to the pharmacy dispensing unit 5020. As noted above, the term "medication order" may be an order associated with one, or more, medications. Thus, a number of medication orders may be generated for a particular patient at a given time at a device 5010, or a single medication order may be analyzed including a number of medications. Thus, it may be assumed that a reference to a "medication order" may be an order associated with a number of medications, or to a number of orders each associated with one or more medications. The new medication order adds certain new medications, and discontinues others. New medications specified in the order, as well as medications to be restocked, may then be placed in a cart at the pharmacy dispensing unit 5020 for delivery 5030 to dispensing device-a 5010-*a*. When a user attempts to restock the device, the cleanup is triggered again, and the discontinued medications are identified for removal and return (e.g., return 5030 to the central dispensing unit 5020).

The patient is then scheduled to be transferred 5035 from location-a 5015-*a* to location-b 5015-*b*. Assume that a new medication order then discontinues certain medications. Either before, or after, the patient is physically transferred 5035 to a new room at location-b 5015-*b*, the medications stored in PSBs at dispensing device-a 5010-*a* are to be transferred 5045 to a new dispensing device associated with the new location (more specifically, dispensing device-b 5010-*b* associated with the transfer room at location-b 5015-*b*). As a user attempts to physically remove 5040 the medications stored in PSBs at dispensing device-a 5010-*a* for transfer, a cleanup is triggered. The discontinued medications may be identified for return 5030 to the pharmacy dispensing unit 5020.

The medication order again changes while the transferred medications are en route, discontinuing certain medications being transferred. When a user attempts to store 5055 the transferred medications at dispensing device-b 5010-*b*, the cleanup is triggered, and the discontinued medications are identified and returned (e.g., returned 5030 to the central dispensing unit 5020). The remaining transferred medications are then stored in dispensing device-b 5010-*b*.

After the transferred medications are stored, assume that a regularly scheduled restock is to occur for the patient at dispensing device-b 5010-*b*. Medications to be restocked may then be placed in a cart at the pharmacy dispensing unit 5020 for delivery 5060 to dispensing device-a 5010-*a*. However, the medication order again changes while the medications are en route, discontinuing certain medications that are currently set to be restocked. When a user attempts to restock dispensing device-b 5010-*b*, the cleanup is triggered again, and the discontinued medications currently being restocked are identified for return 5060 to the central dispensing unit 5020. Also, the remaining discontinued medications stored in dispensing device-b 5010-*b* are identified for removal and return to the central dispensing unit 5020.

The patient is then scheduled for discharge, and a notice of discharge is received at the central server computer system 5005. Medications to be given to the patient upon discharge are identified (e.g., a patient's own medication, or other active medications). As the patient is discharged 5070, the patient is given 5065 these identified medications.

Figure 30:
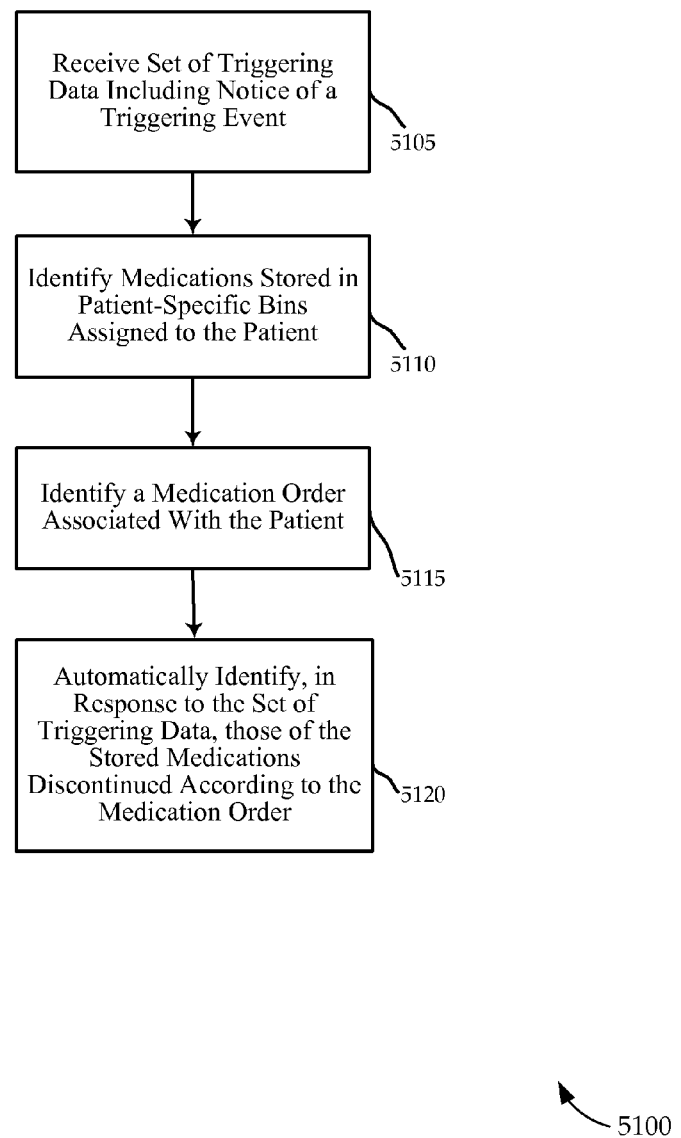
FIG. 30 is a flow diagram illustrating a method of identifying discontinued items from a PSB assigned to a patient according to various embodiments of the invention.

Referring to FIG. 30, one embodiment of a method 5100 of identifying discontinued items from a PSB assigned to a patient is illustrated. This method 5100 may, for example, be performed in whole or in part by the central server computer system 105 of FIG. 1A or 2 or the computer of dispensing device 120 or 220 of FIG. 1A, 1B, or 2. Also, it is worth noting that in this and in other embodiments, various steps may be excluded, and the order may be rearranged.

At block 5105, a set of triggering data is received including notice of a triggering event. At block 5110, medications stored in a PSB assigned to the patient are identified. At block 5115, a medication order associated with the patient is identified. At block 5120, in response to the set of triggering data, those of the stored medications which have been discontinued according to the medication order are automatically identified.

Figure 31:
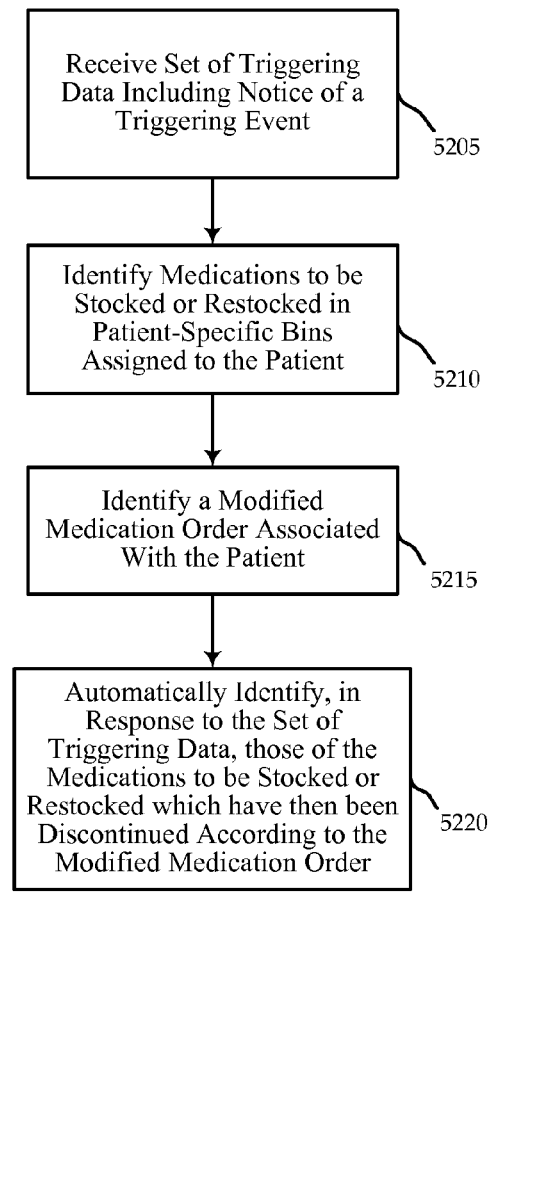
FIG. 31 is a flow diagram illustrating an alternative method of identifying discontinued items from a PSB assigned to a patient according to various embodiments of the invention.

Referring to FIG. 31, one embodiment of a method 5200 of returning items to be stocked a PSB assigned to a patient is illustrated. This method 5200 may, for example, be performed in whole or in part by the central server computer system 105, the computer associated with a dispensing device 120 or 220, or any combination thereof.

At block 5205, a set of triggering data is received including notice of a triggering event. At block 5210, medications to be stocked or restocked for the patient in PSBs assigned to the patient are identified. At block 5215, a medication order associated with the patient is identified. At block 5220, in response to the set of triggering data, those medications to be stocked or restocked which have then been discontinued according to the medication order are automatically identified.

Figure 32:
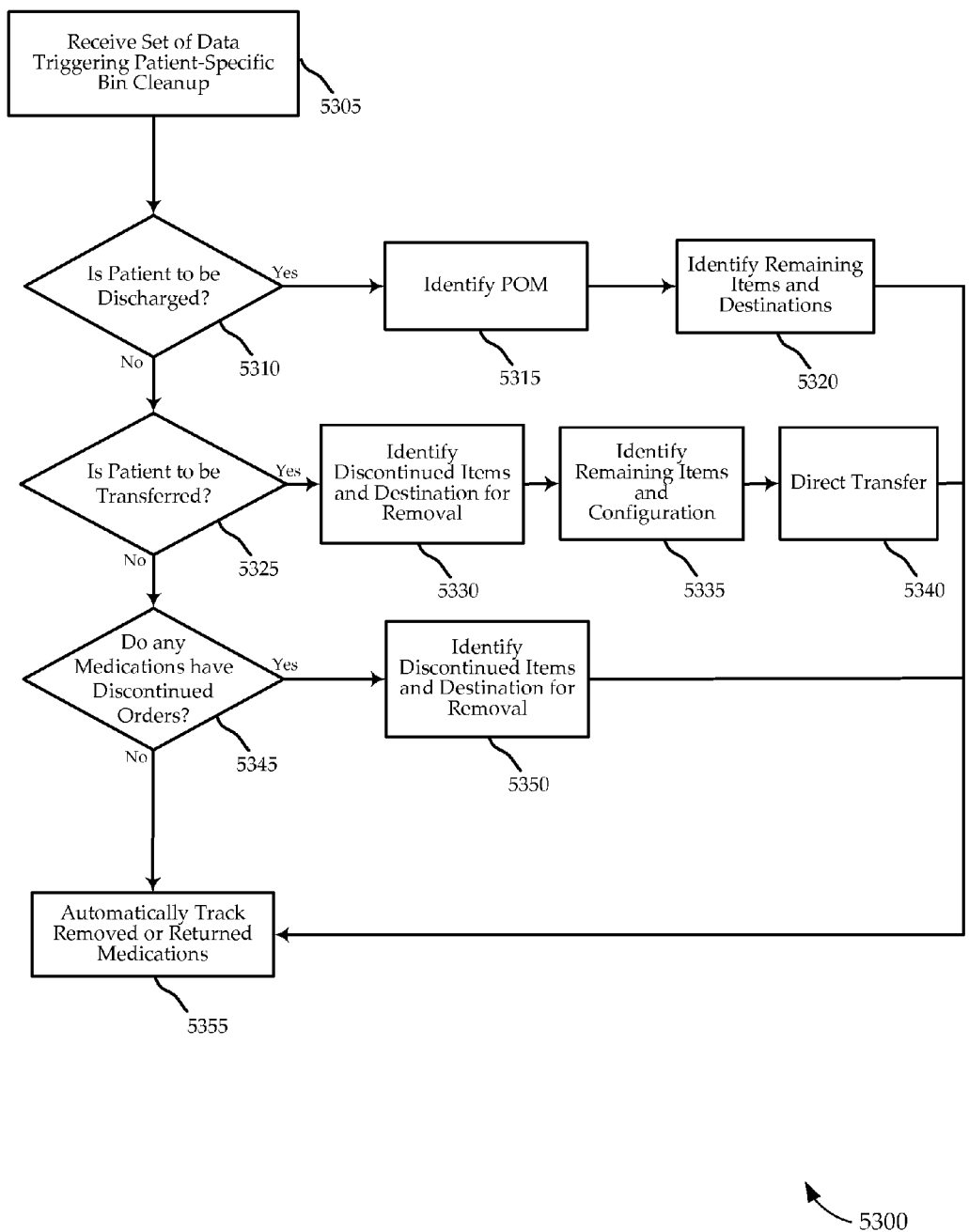
FIG. 32 is a flow diagram illustrating a method of identifying items for removal from a PSB assigned to a patient according to various embodiments of the invention.

Referring to FIG. 32, one embodiment of a method 5300 of managing cleanup of a dispensing device with PSBs is illustrated. This method 5300 may, for example, be performed in whole or in part by the central server computer system 105, the computer associated with a dispensing device 120 or 220, or any combination thereof.

At block 5305, a set of data is received which triggers cleanup for the PSBs of a particular patient. At block 5310, a determination is made whether the patient is to be discharged. If so, at block 5315, the patient's own medication (e.g., medication brought to the healthcare facility by a patient and under an active or future medication order) may be identified for return to the patient. At block 5320, the items remaining in the patent-specific bins (and perhaps other items that were to be stocked or restocked in the PSBs) are identified, as well as their destinations.

If the patient is not to be discharged, a determination is made at block 5325 regarding whether the patient is scheduled to be (or has been) transferred from the room or area associated with the dispensing device. If so, at block 5330, discontinued medications (e.g., medications located in PSBs or medications to be stocked or restocked in the PSBs) are identified, along with their removal destination. At block 5335, the remaining items and their current bin configuration may be identified and stored. At block 5340, the transfer of the remaining items is directed (and, perhaps, transmitted to the dispensing device).

If the patient is not to be discharged or transferred, a determination is made at block 5345 regarding whether any medication to be stored for the patient in the PSBs (or to be stocked or restocked therein) are discontinued. If so, at block 5350, inactive items are identified, along with their removal destination. At block 5355, any removed items are tracked in an ongoing or periodic manner.

Figure 33:
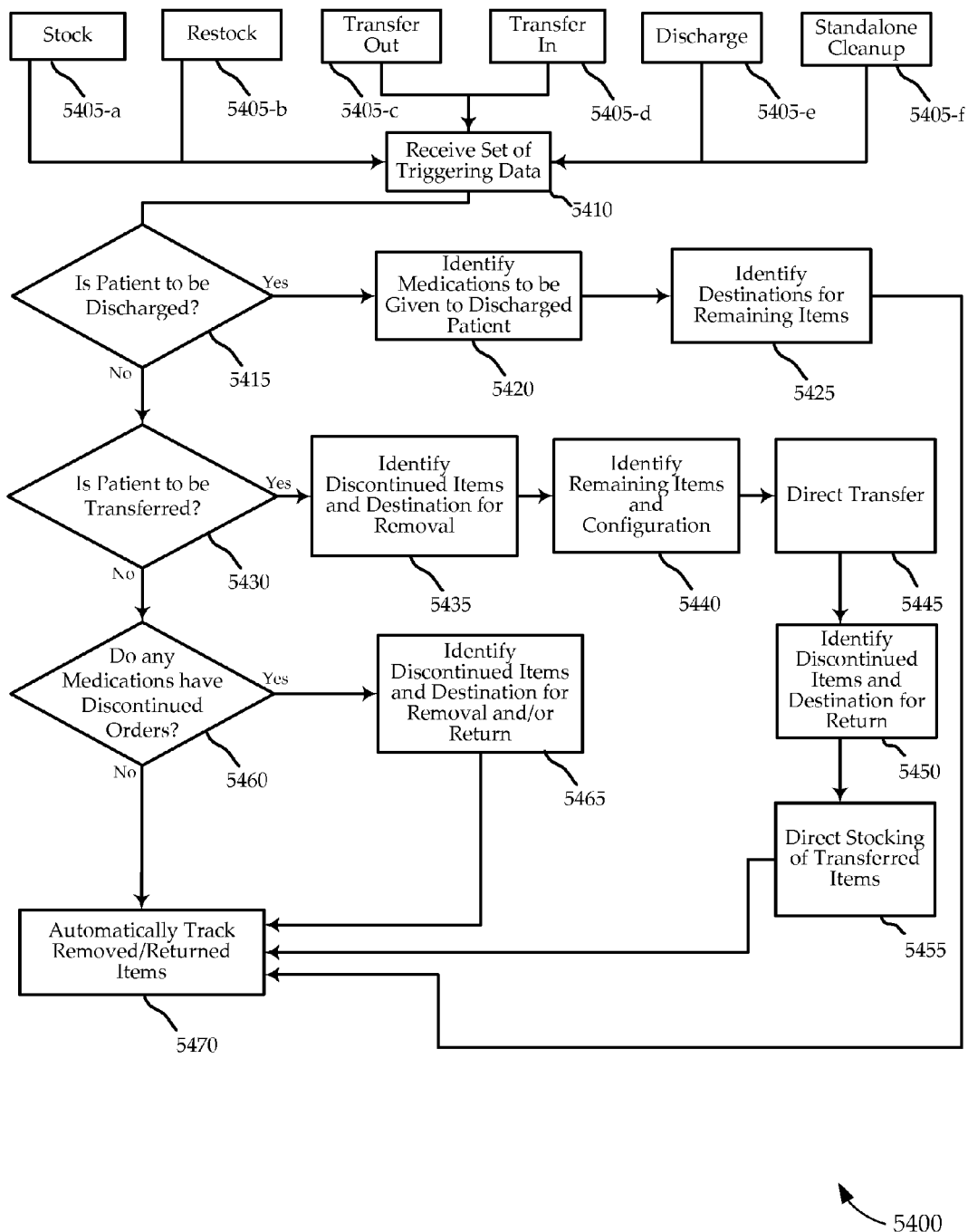
FIG. 33 is a flow diagram illustrating a method of identifying items for removal from a PSB assigned to a patient or for return according to various embodiments of the invention.

Referring to FIG. 33, an alternative method 5400 of managing cleanup of a dispensing device with PSBs is illustrated. This method 5400 may, for example, be performed in whole or in part by the central server computer system 105, the computer associated with a dispensing device 120 or 220, or any combination thereof.

At block 5405, a user may attempt to stock, restock, or remove items from a dispensing device, transfer medications in or out of a dispensing device, or discharge a patient. In one embodiment, this action may cause a set of triggering data to be transmitted providing notice of the triggering event. At block 5410, the set of triggering data is received, which initiates cleanup for the PSBs of the particular patient. At block 5415, a determination is made whether the patient is to be discharged. If so, at block 5420, the medication (e.g., POM or other medication stocked from the healthcare facility to be provided to the patient) may be identified for return to the patient. At block 5425, the items remaining in the patent-specific bins (and perhaps other items that were to be stocked or restocked in the PSBs) are identified, as well as their destinations.

If the patient is not to be discharged, a determination is made at block 5430 regarding whether the patient is scheduled to be (or has been) transferred from a room or area associated with the dispensing device. If so, at block 5435, discontinued medications for the patient located in PSBs are identified, along with their removal destination. At block 5440, the remaining active items and their current bin configuration may be identified and stored. At block 5445, the transfer of the remaining items is directed (and, perhaps, transmitted to the dispensing device). A user may then attempt to stock the transferred medications to the new dispensing device associated with the new room or area. At block 5450, discontinued medications of the transferred medications are identified, along with their destination for return. Thus, if the medication order is modified in the process of transfer, the discontinued or otherwise inactive or oversupplied items may be identified and returned (e.g., to the pharmacy) before they are stocked. At block 5455, the remaining transferred items may be stocked at the new dispensing device.

If the patient is not to be discharged or transferred, a determination is made at block 5460 regarding whether any medication is to be stored for the patient in the PSBs (or to be stocked or restocked therein) are discontinued. If so, at block 5465, discontinued items are identified, along with their removal destination. At block 5470, any removed or returned items are tracked in an ongoing or periodic manner.

VI. Handling of POM: In another set of embodiments, various procedures are described for the handling of medications brought to a healthcare facility by a patient (often referred to as a patient's own medication, or "POM"). In one embodiment, these are medications brought by a patient and authorized by the prescriber to be administered while hospitalized. These procedures may be performed by the central server computer system 105 of FIG. 1A or 2, a computer of dispensing device 120 or 220 of FIG. 1A, 1B, or 2, or any combination thereof.

In one embodiment, medications are brought into a healthcare facility by, for, or on behalf of a patient. These medications may be designated as POM by a user attempting to store them in a dispensing device, or by other healthcare facility personnel when the medication is collected from the patient upon admittance. By way of example, consider FIG. 1A, and note that a user at the dispensing device 120 or a pharmacist at a central dispensing unit 115 may input the designation when entering the medications into the system 100. A set of data including the designation and an identifier for the type of medication may be transmitted from the input device to the central server computer system 105. As set forth in more detail below, novel storage and removal procedures may be used for POM designated medications at PSBs.

As described above, a patient may be associated with a dispensing device 120, perhaps based on the location of his or her room, or on other factors. A dispensing device 120 may include a number of bins allocated as PSBs and/or ISBs. The POM designation, along with an associated patient identifier, PSB, and amount and type information for the medication, may be stored in the data stores 110 by the central server computer system 105. Information may also be stored in the dispensing device 120 computer. The central server computer system 105 may monitor, track, and direct use of the medications stored in the dispensing devices 120. It is worth noting that some, or all, or such functions may be off loaded to a dispensing device 120 computer.

When an item has a POM designation, the central server computer system 105 may be configured to exclude the item from the restocking process. For example, in one embodiment, an item with a POM designation is not be restocked until it is used up. In such a case, a restock directive (e.g., generated by the central server computer system 105) would be implemented only when the supply is used up, at which time the POM designation for the item would be removed. Thus restocking of an item may be suspended or otherwise prohibited until the quantity on hand information is equal to zero. Once the medication with the POM designation is used up, the standard restocking may occur.

The system 100 may, therefore, be configured to manage and hold items with a POM designation separately from medications and other supplies in PSBs. There may be functionality to prevent designated medications from being stored in the same PSBs as medication stocked from the healthcare facility. The bins for PSBs holding POM designated items may be distinguished from bins holding other items.

In another embodiment, an item with a POM designation may instead be restocked when it falls below a threshold level. This threshold level may, but need not, be a different level than would be applied to a medication stocked from the healthcare facility. For example, restocking rules may dictate that for a given medication with a POM designation, a restock will occur when supply falls below 2 days, while restock would otherwise occur for the given medication when supply falls below 3 days. While restocking rules may differ, other rules for both the medication stocked from the healthcare facility and the designated medication may be the same. For example, allergy rules, contraindication rules, storage security requirement rules, and so on may be the same.

Thus, in light of the above, the same (or similar) types of medications may be stored for a patient in two different PSBs at the same time, one with a POM designation and another without. The central server computer system 105 or dispensing device 120 computer may be configured to direct use all of the POM designated items before the same or similar restocked items are used (e.g., suspending use of the restocked items until the POM designated items are used up).

When a patient with POM items is transferred, the POM designation may be retained during and after the patient is transferred. In one embodiment, notice may be received that a patient will transfer from a first location to a second location at the healthcare facility. In response to the notice, a set of data may be transmitted (e.g., from the central server computer system) directing the move of the designated medication from a first dispensing device associated with the first location to a second dispensing device associated with the second location. The designation may be automatically retained during the move. Thus, the POM designation may be transferred to the new dispensing device and a newly assigned PSB when there is a move. The POM designation may be maintained whether the medication transfer occurs before, after, or at overlapping times with the patient transfer.

When a patient is going to be discharged, a central server computer system 105 may receive a notice that the patient is to be discharged. This notice may be a set of data sent from a dispensing device 120 or other connected device (e.g., a device in communication with the central server computer system 105), indicating that the patient will be discharged, and perhaps specifying a time or range of times. When a patient is discharged, the central server computer system 105 may be configured to identify automatically any items with POM designations stored in PSBs for the patient, so a user may return the POM item to the patient. In one embodiment, the central server computer system 105 may determine whether the designated medication(s) are under an active or future medication order, and only direct the return of those medications that remain under such an order. Once the designated medications (and associated PSBs) have been identified for return to the patient or retention, a set of data may be transmitted (e.g., to the dispensing device 120 computer) directing the return or retention of the designated medication.

Figure 34:
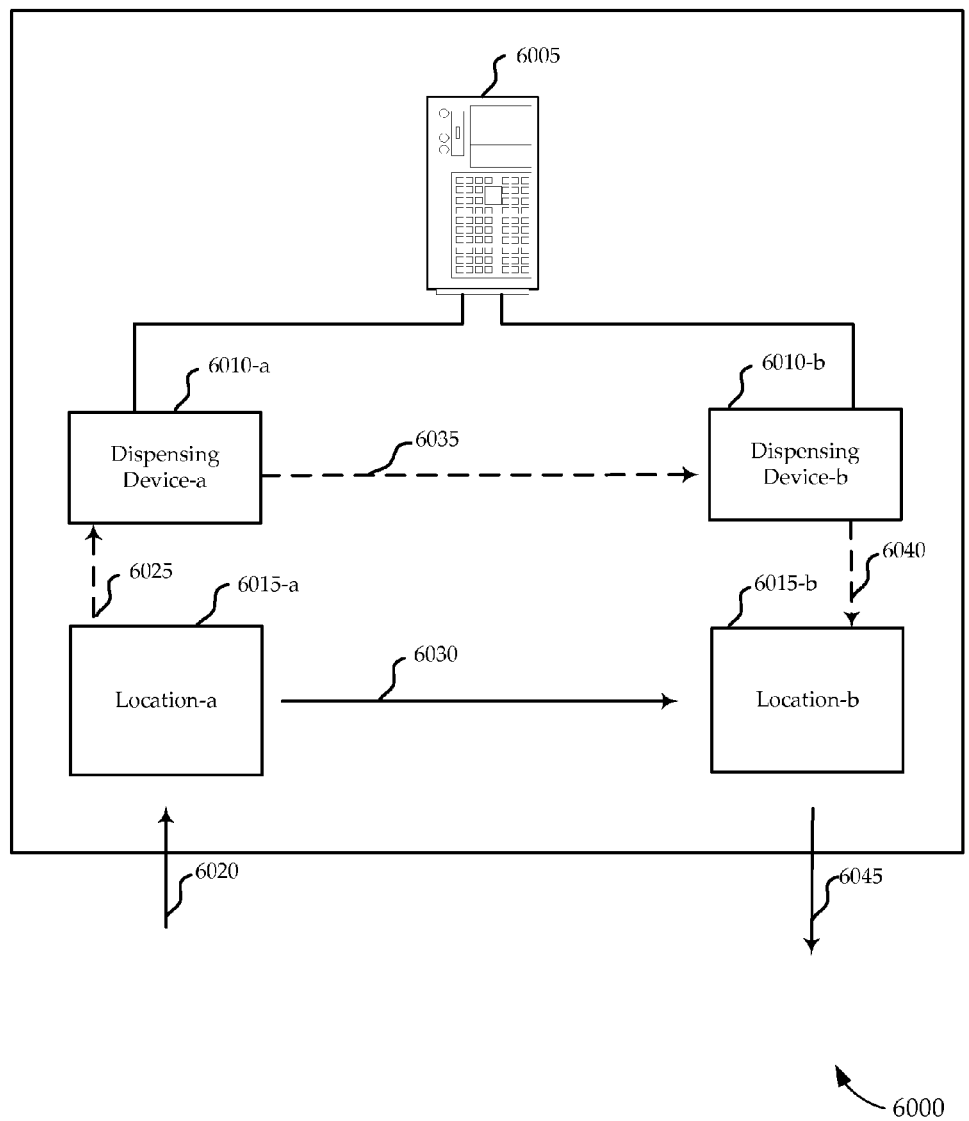
FIG. 34 is a block diagram illustrating a system for designating an item as a patient's own medicine to be stored in a dispensing device which includes patient-specific bins according to various embodiments of the invention.

Turning to FIG. 34, an example of a system 6000 is illustrated for designating a POM to be stored in a dispensing device which includes PSBs. The illustrated system 6000 includes two dispensing devices, dispensing device-a 6010-*a* and dispensing device-b 6010-*b*. Each device may, for example, be a dispensing device 120 or 220 of FIG. 1A, 1B, or 2, and thus may be a cabinet with a number of bins for dispensing medical supplies (e.g., pharmaceuticals, other medications, or other supplies for a patient at a healthcare facility). The bins may be allocated or assigned as PSBs or ISBs, or have other designations. For purposes of this example, assume that the items are medications.

The system 6000 also includes a central server computer system 6005, which is communicatively connected with each dispensing device 6010. The central server computer system 6005 may be the central server computer system 105 of FIG. 1A or 2. The system may include any other number of connected dispensing devices (not shown), and thus the illustrated embodiment is for purposes of example only. Moreover, the following illustrates functionality for purposes of example only, and many other configurations are possible.

Dispensing device-a 6010-*a* may be associated with location-a 6015-*a*. This association may indicate that dispensing device-a 6010-*a* is a cabinet at a nursing station serving a set of rooms which includes location-a 6015-*a*. Assume that in this example, a patient arrives at the healthcare facility, is physically moved 6020 into one of the rooms of location-a 6015-*a*, and the central server computer system 6005 may reflect this association.

At some time before or after arrival of the patient at location-a 6015-*a*, POM may be stored 6025 for the patient in a PSB at dispensing device-a 6010-*a*. The PSB in which the POM is stored may be set apart from PSBs for the patient storing the medication stocked from the healthcare facility. There may be a policy to keep such medications stored in separate PSBs, preventing POM and medication stocked from the healthcare facility from being stored in the same bin. A prescription for the patient may include the type of medication making up the POM, and the POM may be administered at the healthcare facility. In one embodiment, this type of medication for the patient is not restocked until the POM is used up; in other embodiments, the restocking levels for a POM may differ from restocking levels of the same medications stocked from the healthcare facility. The specific restocking levels may depend on the type of medication, the rate of use, the time required for restocking, and other related factors.

The patient may then be scheduled to be transferred 6030 from location-a 6015-*a* to location-b 6015-*b*. Either before, or after, the patient is physically transferred 6030 to a new room at location-b 6015-*b*, the POM stored in PSBs at dispensing device-a 6010-*a* is transferred 6035 to a new dispensing device associated with the new location (more specifically, dispensing device-b 6010-*b* associated with the transfer room at location-b 6015-*b*). The transferred POM may be transferred together with medication stocked from the healthcare facility. The designation for each POM may be retained during the transfer, and/or reapplied after the transfer.

When a user stores the transferred medications at dispensing device-b 6010-*b*, the central server computer system 6005 may again direct that the POM be stored separately (e.g., in separate bins) from the medications stocked from the healthcare facility. The transferred medications are then stored in dispensing device-b 6010-*b*. Again, restocking may occur for the transferred medications (including POM), but may differ depending on the restocking policies of the healthcare facility and the type of POM transferred.

The patient is then scheduled for discharge, and a notice of discharge is received at the central server computer system 6005. Medications to be given to the patient upon discharge are identified (e.g., POM, or other active medications), and the POM may be identified for return based on the identification. A set of data identifying these medications may be transmitted to the dispensing device 6010-*b*. Before the patient is discharged 6045, the patient is given 6040 these identified medications.

Figure 35:
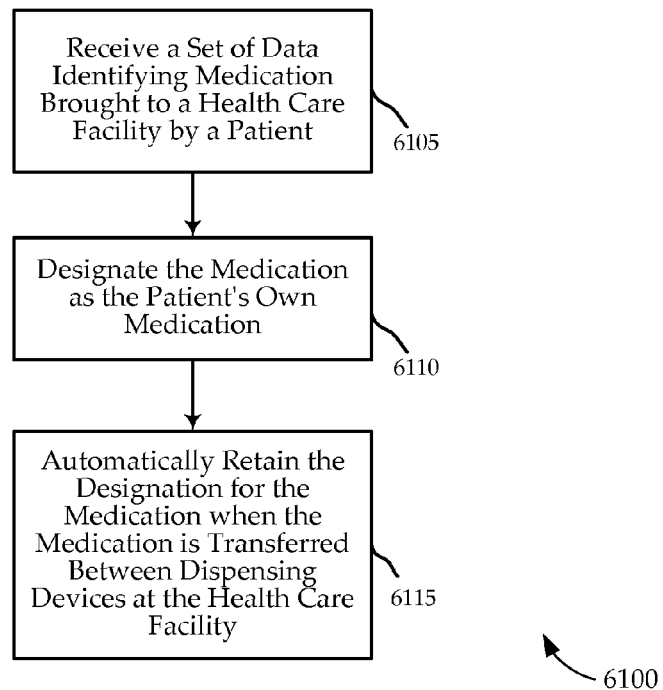
FIG. 35 is a flow diagram illustrating a method of designating medication as a patient's own medication according to various embodiments of the invention.

Referring next to FIG. 35, one embodiment of a method 6100 of designating medication as a patient's own medication is illustrated. This method 6100 may, for example, be performed in whole or in part by the central server computer system 105 of FIG. 1A or 2. Alternatively, the method 6100 may, for example, be performed in whole or in part by a computer associated with a dispensing device 120 or 220 of FIG. 1A, 1B, or 2. Also, it is worth noting that in this and other method embodiments, various steps may be excluded, and the order may be rearranged.

At block 6105, a set of data is received that identifies medication brought to a healthcare facility by a patient. At block 6110, the medication is designated as the patient's own medication. At block 6115, the designation for the medication is automatically retained when the medication is transferred between dispensing devices at the healthcare facility.

Figure 36:
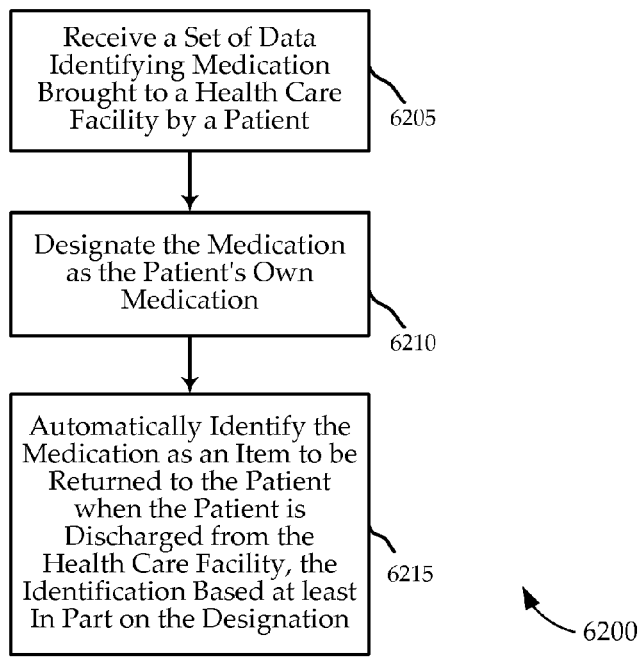
FIG. 36 is a flow diagram illustrating a method of designating medication to be returned to a patient according to various embodiments of the invention.

Referring to FIG. 36, an example of a method 6200 of designating medication to be returned to a patient is shown. By way of example, this method 6200 may, for example, be performed in whole or in part by the central server computer system 105, the computer associated with a dispensing device 120 or 220, or any combination thereof.

At block 6205, a set of data is received that identifies medication brought to a healthcare facility by a patient. At block 6210, the medication is designated as POM. At block 6215, the medication is automatically identified as an item to be returned to the patient when the patient is discharged from the healthcare facility, the identification based at least in part on the designation.

Figure 37:
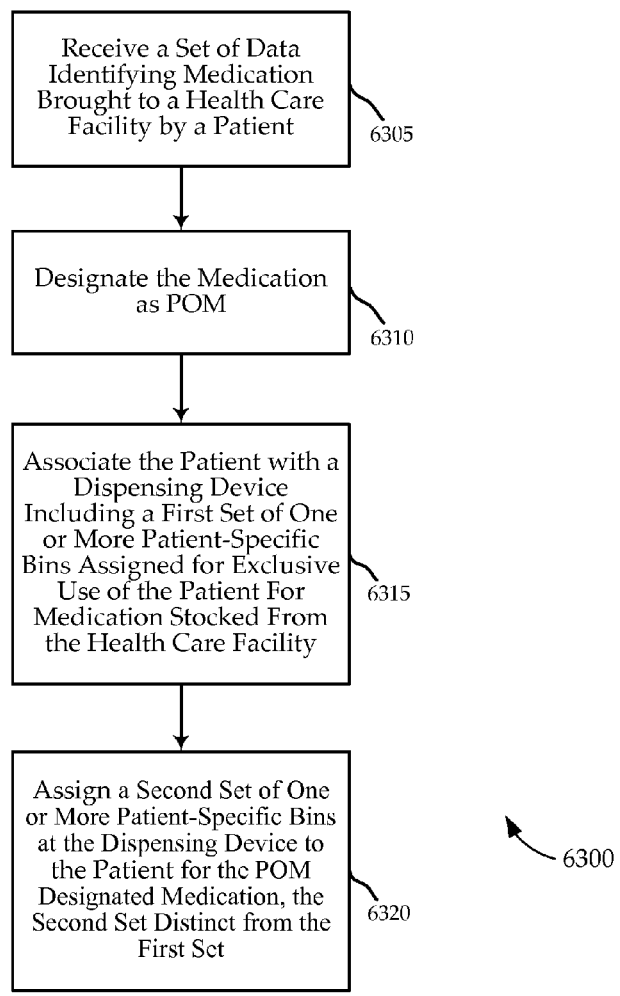
FIG. 37 is a flow diagram illustrating a method of differentiating between certain medications in the assignment of patient-specific bins according to various embodiments of the invention.

Referring to FIG. 37, an example of a method 6300 of differentiating between certain medications in the assignment of PSBs is shown. This method 6300 may, for example, be performed in whole or in part by the central server computer system 105, the computer associated with a dispensing device 120 or 220, or any combination thereof.

As in other embodiments, at block 6305, a set of data is received that identifies medication brought to a healthcare facility by a patient. At block 6310, the medication is designated as POM for the patient. At block 6315, the patient is associated with a dispensing device (e.g., based on an association between a room and a dispensing device). The dispensing device includes a first set of one or more PSBs assigned for exclusive use of the patient for medication stocked from the healthcare facility. At block 6320, a second set of one or more PSBs at the dispensing device is assigned to the patient for storage of the POM designated medication, the second set distinct from the first set. Thus, there may be a rule to assign POM designated items to different PSBs than the standard items to be stocked from the healthcare facility. The rule may be automated, or enforced by the user or healthcare facility.

Figure 38:
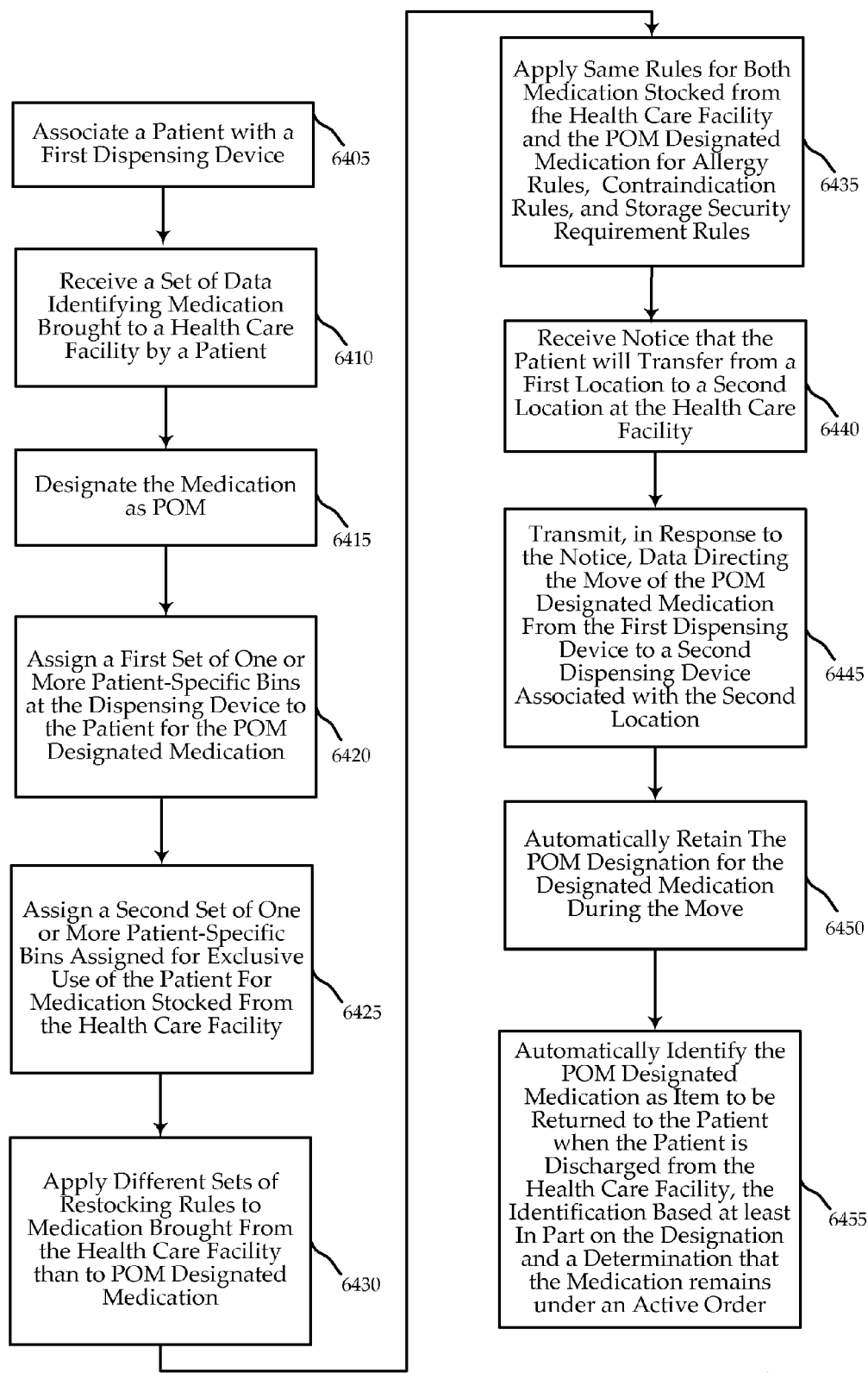
FIG. 38 is a flow diagram illustrating an alternative method of designating medication as a patient's own medication according to various embodiments of the invention.

Referring to FIG. 38, an alternative embodiment of a method 6400 of designating medication as a patient's own medication is shown. As in other embodiments, this method 6400 may, for example, be performed in whole or in part by the central server computer system 105, the computer associated with a dispensing device 120 or 220, or any combination thereof.

At block 6405, a patient is associated with a first dispensing device. At block 6410, a set of data is received that identifies medication brought to a healthcare facility by a patient. At block 6415, the medication is designated as POM for the patient. At block 6420, a first set of one or more PSBs at the dispensing device is assigned to the patient for the POM designated medication. At block 6425, a second set of one or more PSBs is assigned for exclusive use of the patient for medication stocked from the healthcare facility.

At block 6430, different sets of restocking rules are applied to medication from the healthcare facility than to the POM designated medication. At block 6435, certain rules are applied to both medication stocked from the healthcare facility and the POM designated medication, the same set of rules including allergy rules, contraindication rules, and storage security requirement rules.

At block 6440, a notice is received that the patient will transfer from a first location to a second location at the healthcare facility. At block 6445, data is transmitted, in response to the notice, directing the move of the POM designated medication from the first dispensing device to a second dispensing device associated with the second location. At block 6450, the POM designation for the medication is automatically retained during the move. At block 6455, the POM designated medication is identified as an item to be returned to the patient when the patient is discharged from the healthcare facility, the identification based at least in part on the designation and a determination that the medication remains under an active order.

Figure 39:
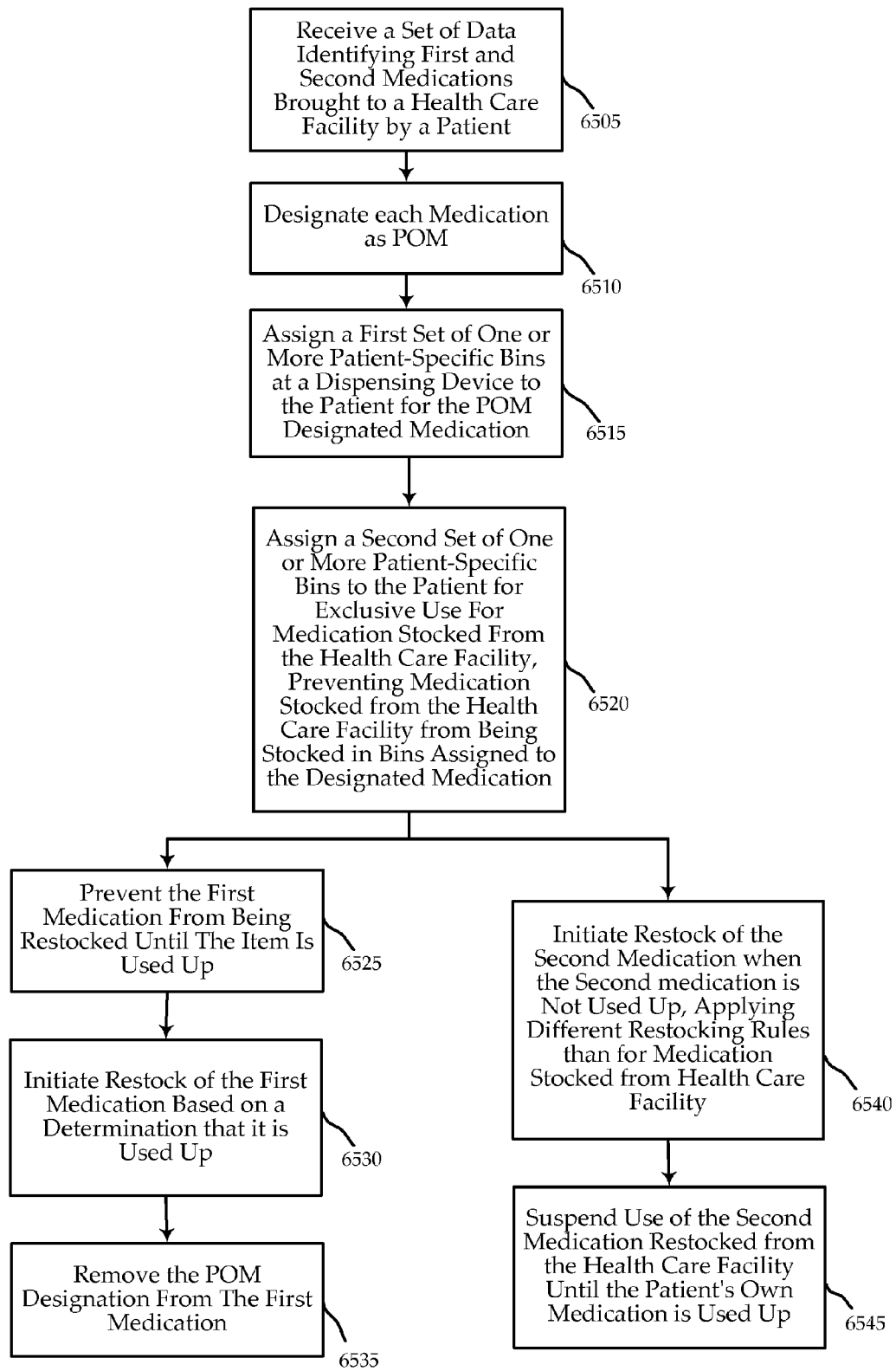
FIG. 39 is a flow diagram illustrating a method of managing medication designated as a patient's own medication according to various embodiments of the invention.

Referring to FIG. 39, yet another alternative example of a method 6500 of designating medication as a patient's own medication is shown. As in other embodiments, this method 6500 may, for example, be performed in whole or in part by the central server computer system 105, the computer associated with a dispensing device 120 or 220, or any combination thereof.

At block 6505, a set of data is received that identifies first and second medications brought to a healthcare facility by a patient. At block 6510, the first and second medications are each designated as POM. At block 6515, a first set of one or more PSBs at a dispensing device is assigned to the patient for the POM designated medications. At block 6520, a second set of one or more PSBs is assigned to the patient for exclusive use for medication stocked from the healthcare facility. A rule prevents medication stocked from the healthcare facility from being stocked in bins assigned to the designated medication.

At block 6525, the first medication is prevented from being restocked until the item is used up. At block 6530, restocking of the first medication is initiated based on a determination that it is used up. At block 6535, the designation is removed from the restocked first medication.

Other restocking rules are applied for the second medication (e.g., based on the type of medication, regularity of use, etc.). At block 6540, restock of the second medication is initiated when the second medication is not used up, and different restocking rules (e.g., waiting until the medication is more depleted before restocking) are applied for the second medication than for medication stocked from healthcare facility. At block 6545, use (e.g., user access or patient use) of the second medication restocked from the healthcare facility is suspended until the POM designated stock is used up.

VII. Handling of Multi-Use Items: In another set of embodiments, various procedures are described for the handling of multi-use items. Multi-use items are typically dispensers of medication configured for multiple administrations to the same patient, and may include both the medication and a container configured to dispense the medication for the patient. Examples may include topical creams, eye drops, and inhalers.

In one embodiment, an unused multi-use item may be initially stored in an ISB available to a number of patients at a dispensing device. When notice is received of a first use by a patient of the previously unused multi-use item, return of the used multi-use item is directed to a PSB for the patient in the dispensing device. Once used, the multi-use item is to be assigned for exclusive use of the patient, and managed accordingly. In some embodiments, a system differentiates a multi-use item from a container or dispenser that includes multiple doses that are used or shared by multiple patients. The following procedures described for multi-use items may be performed by the central server computer system 105 of FIG. 1A or 2, a computer associated with dispensing device 120 or 220 of FIG. 1A, 1B, or 2, or any combination thereof.

In one embodiment, a multi-use item (e.g., a dispenser of medication such as a tube of topical cream, eye drops, or an inhaler) is identified. The dispenser of medication (or a stored identifier for the dispenser, e.g., in data stores 110) is associated with a designation indicating that the item is a multi-use item. The multi-use item may be designated as such by a user attempting to store the item in a dispensing device (e.g., by indicating the designation via an input on a dispensing device 120 or 220 computer), or by other healthcare facility personnel when the medication is stored or received at the healthcare facility. By way of example, consider FIG. 1A, and note that a user at the dispensing device 120 or a pharmacist at a central dispensing unit 115 may input the designation when entering the medications into the system 100.

A set of data including the designation and/or an identifier for the type of medication may be processed and transmitted from an input device (e.g., a dispensing device 120 computer) to the central server computer system 105, and may be stored in data stores 110. Alternatively, the item may be automatically recognized as a multi-use item (e.g., via a look-up of the identifier for the item received at the central server computer system 105), and the designation may be made automatically. Thus, the unused multi-use item may be identified and designated by information received from any number of sources.

As discussed above, a central server computer system 105 may be in communication with a number of dispensing devices 120. A patient may be associated with a dispensing device 120, perhaps based on the location of his or her room or area, among other factors. A dispensing device 120 may include a number of bins allocated as PSBs and ISBs. The multi-use designation, along with an associated patient identifier, PSB identifier, and amount and type information for the medication, may be stored in the data stores 110 by the central server computer system 105. The central server computer system 105 may monitor, track, and direct use of the medications stored in the dispensing devices 120. It is worth noting that some, or all, of such functions may be off loaded to a dispensing device 120 computer.

When an unused item has a multi-use designation, the unused item may be stocked in an ISB, and thus may be available for any of the patients associated with the dispensing device 120. For example, an unused dispenser of eye drops may be stored in an ISB for use of any of the patients associated with the device. The central server computer system 105 may receive data indicating that the unused item will be stored at the dispensing device 120, and may identify the ISB for storage of the item. The central server computer system 105 may transmit a first set of instruction data directing storage of the unused item in the identified ISB, or the ISB may be identified by a dispensing device 120 computer. Alternatively, the multi-use item may come directly or indirectly from the central dispensing unit 115, and not be placed initially in an ISB.

Therefore, a user may be directed to the ISB by the central server computer system 105 or dispensing device 120 computer in response to a request to obtain the medication. A user (e.g., a nurse, or the patient himself) may use the previously unused multi-use item stored in the ISB. Information about the use may be input to and processed by the dispensing device 120 computer or other input device. A message may then be sent (e.g., from the dispensing device 120 computer) indicating the initial use by the patient. A second set of instruction data may be generated, and perhaps transmitted, directing storage of the used multi-use item in a PSB assigned to the patient at the dispensing device 120. Thus, in response to a received use input or message, the multi-use item may be assigned to the first patient for exclusive use. The PSB where the item is to be stored may be identified after the message indicating the initial use is received, and this identification may be received by a user at the dispensing device 120. PSBs for storage of the used multi-use item may be distinct from single-use medications stored from the healthcare facility, and there may be logic preventing them from being stored together.

Thus, a set of data may be received (e.g., at the dispensing device 120, or at the central server computer system 105 from a user at the dispensing device 120) that includes a request to obtain the medication for administration to the first patient. In response to the request, the central server computer system 105 or dispensing device 120 computer may then automatically identify the location of the multi-use item. For example, data stores 110 or other memory may be queried to determine whether the patient is associated with a used dispenser of the medication at the dispensing device 120 (e.g., in the case when a patient has already used the medication). If no used dispenser of the medication assigned to the patient is available (e.g., it is used up), the ISB storing the unused dispenser of medication may be automatically identified.

After a use of a multi-use item and/or in response to the request to obtain the medication, a determination may be made as to whether the dispenser of medication stored in the PSB for the patient is used up. This determination may be performed with a query to the user, and the resulting response to the query. When it is determined that additional medication remains in the dispenser for the patient, the medication may be excluded from restocking at the PSB. When it is determined that no additional medication remains in the dispenser for the patient, an ISB may be identified containing an additional unused dispenser of the medication.

For each used dispenser of medication designated a multi-use item, use of medication may be tracked. Thus, use may be tracked for one or more patients, for one or more designated multi-use items, and at one or more dispensing devices. In this way, certain restocking thresholds may be set so that enough unused medication of each type will be stored in an ISB as it is needed. This tracking and advance restocking may be more suited to dispensing devices serving a larger number of rooms, to medications used more regularly, and/or to medications of more critical importance to a given set of patients. These factors may each be used to control the threshold restock level.

Threshold restocking levels may be modified based on individual or group determinations. For example, consider a patient who is using a multi-use item that is deemed to be of critical importance for the well-being of the patient, but is used very rarely by other patients. The use of the item by the patient may be monitored, and the item restocked in an ISB when the remaining amount falls below a threshold level (e.g., 25% remaining) that will assure additional stock is available when the item is depleted. Compare this with patients who are each using a multi-use item that is used very regularly by other patients. The use of the item by each of the patients may be monitored, and the items restocked in an ISB based on group threshold characteristics. For example, assume that there are three patients who will be using an item up at different times. Instead of restocking three different times, there may instead be a single restocking of three items (perhaps with a different threshold).

The designation for multi-use items may be retained for a dispenser of medication as a patient is transferred within a healthcare facility, and may further be retained until the medication is used up. A set of data may also be received (e.g., at a central server computer system 105 or dispensing device 120 computer) indicating that the patient is to be discharged from the healthcare facility (perhaps indicating a time or range of times for the discharge). A determination may be made as to whether the medication remains under an active (or future) medication order. Based on the determination, a user (e.g., a nurse or other discharge personnel) may be directed to provide the used dispenser of medication to the patient upon discharge.

Figure 40:
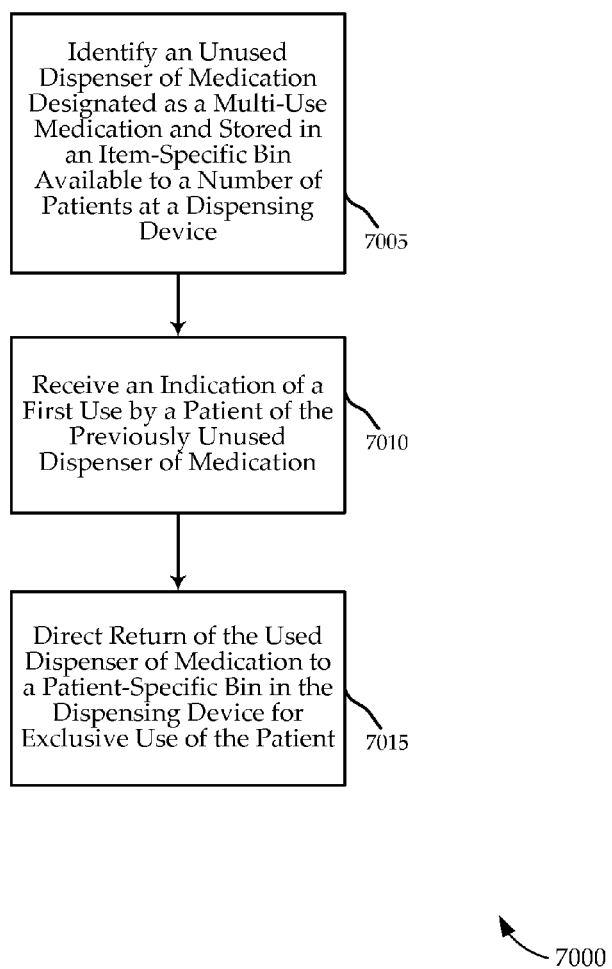
FIG. 40 is a flow diagram illustrating a method of managing the storage of multi-use items according to various embodiments of the invention.

Referring next to FIG. 40, one embodiment of a method 7000 of managing the storage of multi-use items is illustrated. This method 7000 may, for example, be performed in whole or in part by the central server computer system 105 of FIG. 1A or 2. Alternatively, the method 7000 may, for example, be performed in whole or in part by a computer associated with a dispensing device 120 or 220 of FIG. 1A, 1B, or 2. Also, it is worth noting that in this and other method embodiments, various steps may be excluded, and the order may be rearranged.

At block 7005, an unused dispenser of medication is identified which is designated as a multi-use medication and stored in an item-specific bin available to a number of patients at a dispensing device. At block 7010, notice is received of a first use by a patient of the previously unused dispenser of medication. At block 7015, return of the used dispenser of medication is directed to a PSB in the dispensing device and the dispenser is assigned for exclusive use of the patient.

Figure 41:
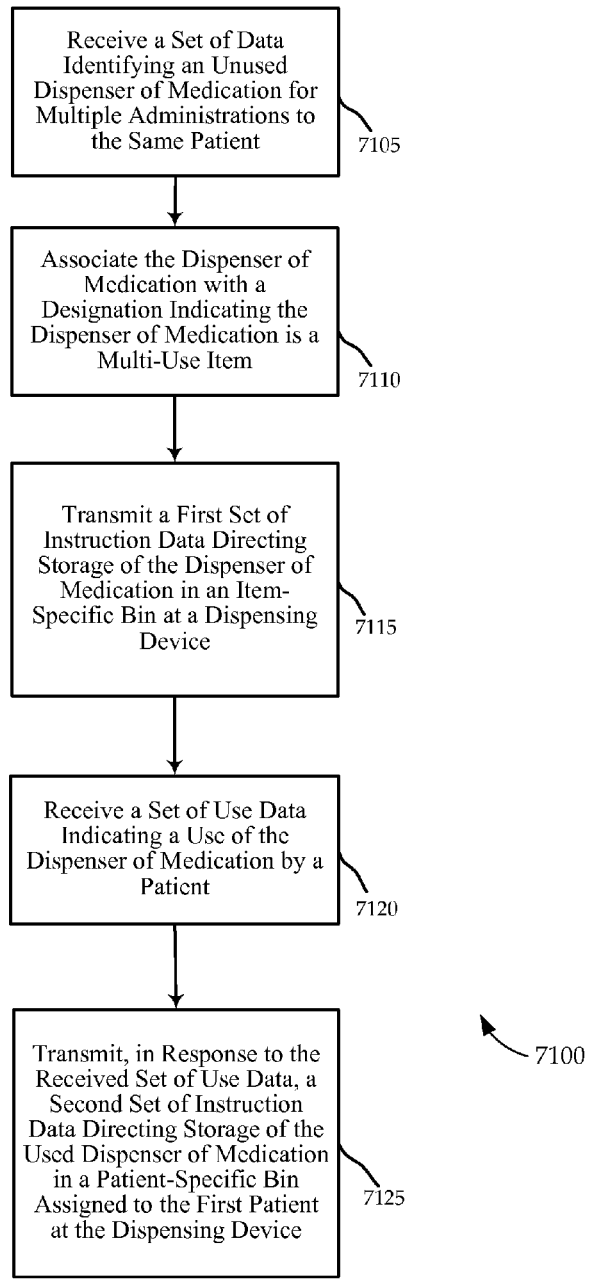
FIG. 41 is a flow diagram illustrating a method of designating and storing multi-use items according to various embodiments of the invention.

Referring to FIG. 41, an example of a method 7100 of designating and storing multi-use items is shown. By way of example, this method 7100 may be performed in whole or in part by the central server computer system 105, the computer associated with a dispensing device 120 or 220, or any combination thereof.

At block 7105, a set of data is received identifying an unused dispenser of medication for multiple administrations to a same patient. At block 7110, the dispenser of medication is associated with a designation indicating the dispenser of medication is a multi-use item. At block 7115, a first set of instruction data is transmitted directing storage of the dispenser of medication in an ISB at a dispensing device. At block 7120, a set of use data is received indicating a use of the dispenser of medication by a patient. At block 7125, in response to the received set of use data, a second set of instruction data is transmitted directing storage of the used dispenser of medication in a PSB assigned to the first patient at the dispensing device.

Figure 42:
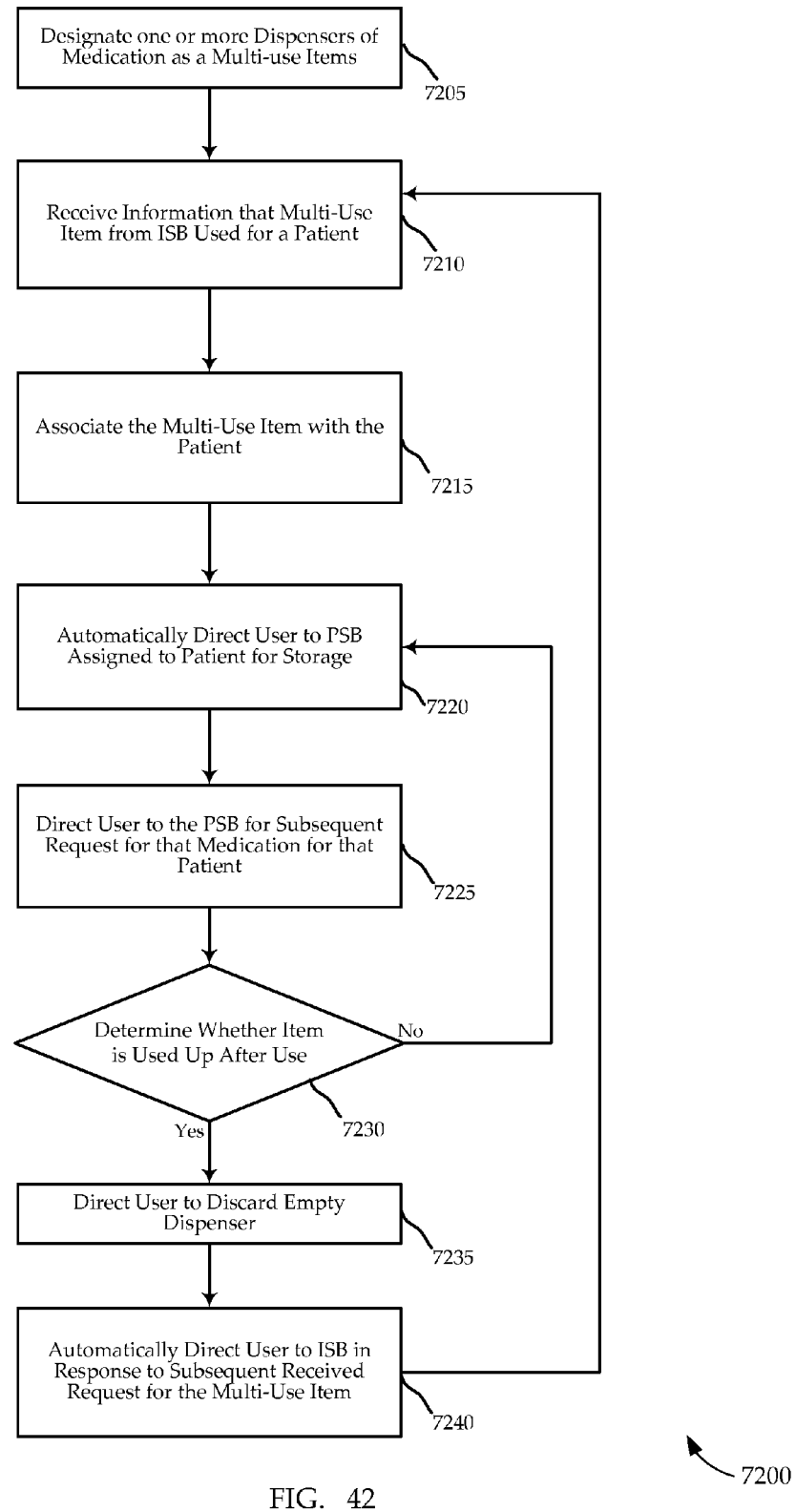
FIG. 42 is a flow diagram illustrating a method of differentiating and managing multi-use items according to various embodiments of the invention.

Referring to FIG. 42, an example of a method 7200 of differentiating and managing multi-use items is shown. This method 7200 may, for example, be performed in whole or in part by the central server computer system 105, the computer associated with a dispensing device 120 or 220, or any combination thereof.

At block 7205, a dispenser of medication is designated as a multi-use item. This designation may be input by a user, or made automatically based on a look-up of characteristics of the item. At block 7210, information is received that the multi-use item stored in an ISB is used for a patient. This use information may be explicit, or inferred from data input by a user (e.g., a nurse) to a dispensing device. The multi-use item is then associated with the patient at block 7215.

At block 7220, the user (e.g., a nurse who administered the previously unused multi-use item to the patient) is automatically directed to a PSB for storage of the multi-use item, the PSB assigned to the patient. For a subsequent request for that medication for that patient, the user is directed to the PSB at block 7225.

After a second use, a determination may be made as to whether the medication is used up at block 7230. If it is determined that the medication is not used up, the process returns to block 7220, where the user is directed to return the item. Subsequent requests and returns for the medication will be directed to the PSB until a determination is made that the medication is used up. Once it is determined that the item is used up, the user may be directed to discard the empty dispenser at block 7235. Then, a subsequent request for the medication for the patient may be automatically directed to an ISB storing an unused dispenser of the medication at block 7240, and the process may revert to block 7210.

Figure 43:
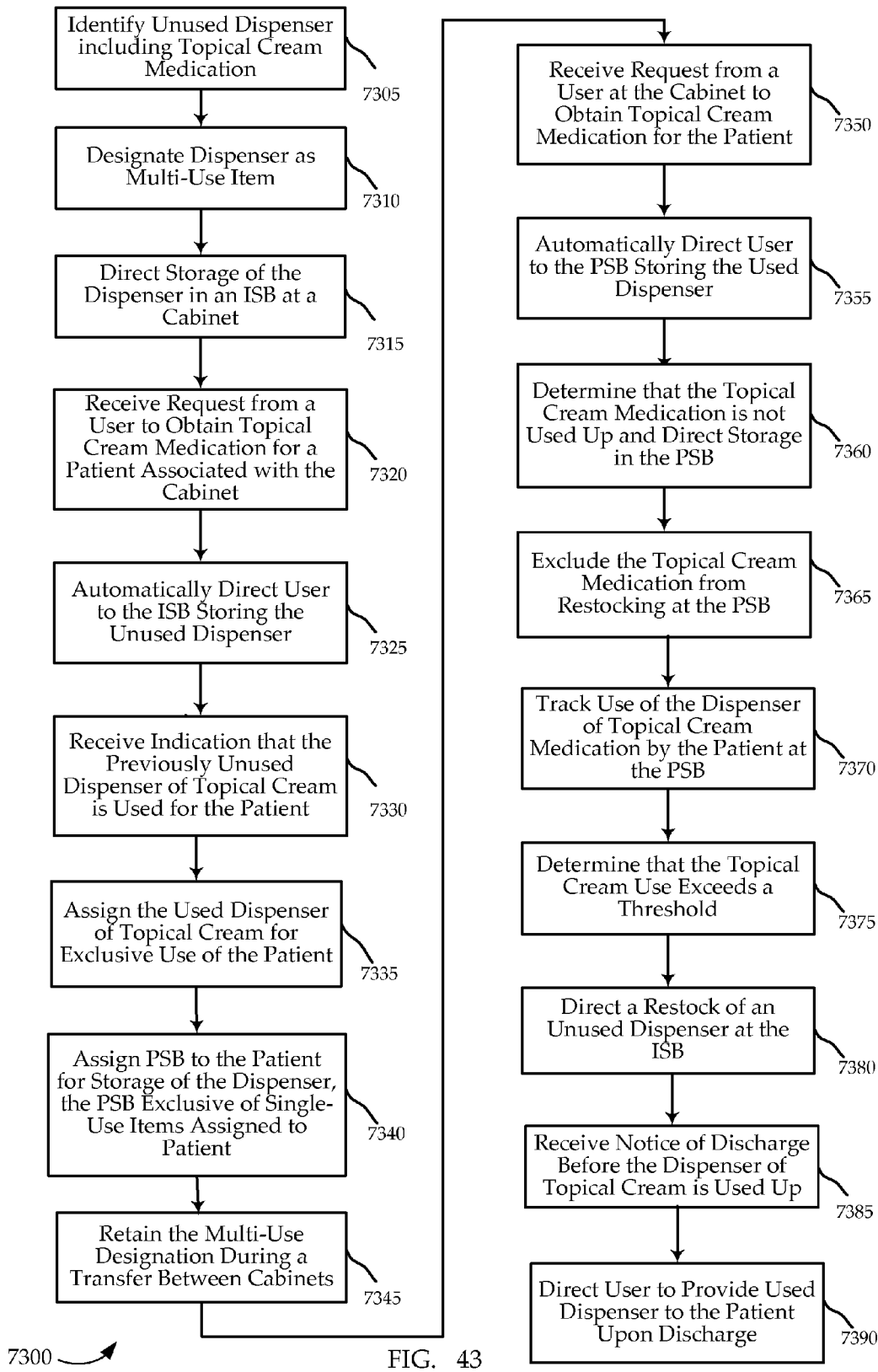
FIG. 43 is a flow diagram illustrating a method of managing medication with a multi-use designation through the patient life cycle according to various embodiments of the invention.

Referring next to FIG. 43, an alternative embodiment of a method 7300 of managing medications with a multi-use designation is shown. As in other embodiments, this method 7300 may be performed by the central server computer system 105, a dispensing device 120 or 220 computer, or any combination thereof. It is worth emphasizing that the order of the steps may be changed, and in certain embodiments steps may be dropped or added.

At block 7305, an unused dispenser of topical cream medication is identified (e.g., during a stocking or restocking procedure). At block 7310, the dispenser is designated as a multi-use item. The designation may be automatic, or may be selected by a user (e.g., via a user interface for the computer integrated with a cabinet). At block 7315, the storage of the dispenser is directed to an ISB at a cabinet (e.g., the cabinet serving a number of rooms at a healthcare facility)

At block 7320, a request is received from a user (e.g., a nurse) to obtain topical cream medication for a patient associated with the cabinet. For example, the received request may be in the form of an input by a user at the cabinet, or in the form of a set of data indicative of the request received from the cabinet. At block 7325, the user is automatically directed to the ISB storing the unused dispenser.

At block 7330, notice is received that the previously unused dispenser of topical cream is used for the patient. This notice may be in the form of a set of data received from the device, or may be an input from a user. The notice may be implicit or explicit. At block 7335, the used dispenser of topical cream is assigned for exclusive use of the patient. At block 7340, a PSB at the cabinet is assigned to the patient for storage of the dispenser, the PSB exclusive of single-use items assigned to patient. Items with multi-use designations may be prevented from being stored in the same PSB as single-use items. The user may be directed to the PSB for return of the used dispenser.

At block 7345, the multi-use designation may be retained during a transfer of the dispenser between cabinets (e.g., when there is a patient transfer). At block 7350, a request is received from a user at the cabinet to obtain topical cream medication for the patient. Again, the received request may be in the form of an input received from a user at the cabinet, or in the form of a set of data including the request received from the cabinet. At block 7355, the user is automatically directed to the PSB storing the used dispenser. This may be performed by sending a set of instructions to the cabinet (e.g., sent from a central server computer system), or may be performed by the cabinet itself.

At block 7360, a determination is made that the topical cream medication is not used up, and storage is directed to the PSB. This determination and direction may be performed locally by the computer integrated with the cabinet, or received from a remote source (e.g., a central server computer system). At block 7365, when a restocking procedure occurs for the cabinet, the topical cream medication is excluded from restocking at the PSB based on the multi-use designation.

At block 7370, use of the dispenser of topical cream medication by the patient is tracked at the PSB. At block 7375, it is determined that the topical cream use exceeds a threshold (e.g., medication is 75% used up, medication is 90% used up, less than one day's supply remains, less than two days' supply remains, etc.). At block 7380, a restock of an unused dispenser of the topical cream medication is ordered at the ISB. This restock may be done in an attempt to ensure that there is an unused dispenser for the patient available in an ISB when his topical cream medication runs out.

However, at block 7385, notice of discharge is received before the dispenser of topical cream is used up. This notice may be an input by a user, or perhaps a set of data indicating that a user will be discharged at a time or range of times. A determination may be made whether the user remains under an active medication order. At block 7390, a user is directed to provide the used dispenser to the patient upon discharge.

In one embodiment, the multi-use item may be charged to the patient upon initial use only, and not charged on a per-application basis.

VIII. Bin Allocation: Various systems, methods, and device configurations are described for managing the allocation between PSBs and other bins at a dispensing device. The functions described related to managing such an allocation may be performed by the central server computer system 105 of FIG. 1A or 2, the computer of dispensing device 120 or 220 of FIG. 1A, 1B, or 2, or any combination thereof.

In one embodiment, a current bin allocation at a cabinet is identified. This may be performed by identifying those bins at a cabinet allocated as PSBs and ISBs. Occupancy rates associated with the PSBs are determined. These occupancy rates may reflect the current PSB occupancy rate at the cabinet, but may also be based on past and future occupancy data adjusted to the current bin allocation. As these PSB occupancy rates increase, the ability of a user to store medications in PSBs may be adversely affected. Certain occupancy rates may trigger a re-allocation of bins at the device, increasing the allocation of PSBs. Alternatively, such occupancy rates may automatically trigger one or more messages to a user or cabinet advising re-allocation. In other embodiments, a message may be sent on a scheduled basis, or be offered in response to a user inquiry.

The assessment and re-allocation process described herein may occur for a particular dispensing device, set of dispensing devices, or across a healthcare facility. Thus, although much of following discussion relates to allocation of PSBs and ISBs at a particular dispensing device, a similar analysis and allocation may be made for a set of dispensing devices, or facility wide. Also, while the re-allocation process may be described herein as an automatic bin re-allocation, in other embodiments the steps of automated re-allocation may be replaced with an automated transmission of a message advising or directing the re-allocation. Therefore, there may be different levels of automation in the process: automated re-allocation, automated re-allocation advisory messages, or automated messages in response to user inquiries.

At a particular dispensing device (e.g., dispensing device 120 of FIG. 1A or 1B), assume that there is an existing allocation of ISBs and PSBs. Information regarding a current bin allocation at a device may be collected and stored by the central server computer system 105, the dispensing device 120, or any combination thereof. For example, a central server computer system 105 may identify bins allocated as PSBs and ISBs by querying the dispensing device 120, or by accessing data on such allocations stored in data stores 110. This data may reflect the current bin allocation on a real-time, or delayed, basis. The current bin allocation data may also reflect a type designation of each of the bins at a device (e.g., according to size, storage capacity, control levels, protected bins, refrigeration capabilities, POM or multi-use designations, security levels, etc).

The dispensing device 120 and its bins (e.g., PSBs and ISBs) may be monitored or queried to determine the current occupancy rate (e.g., via remote monitoring by a central server computer system 105). The dispensing device 120 may also transmit data to the central server computer system 105 indicating occupancy changes at the device (e.g., when a user stocks or removes an item). Occupancy data may, but need not, be categorized for various bin types at the dispensing device 120. In one embodiment, the occupancy rate is calculated by analyzing the percentage of bins storing one or more items.

Bins may be re-allocated as PSBs or ISBs, or messages may be transmitted advising such re-allocations, based on current occupancy rates. For example, current PSB occupancy rates over a threshold (e.g., 80% or 90%) may trigger this re-allocation or messaging. The re-allocation or re-allocation directives may be performed or advised specifically for each type of PSB, and the triggering threshold may be different for different types of bins. Typically, ISBs of a given type will be re-allocated as PSBs of the same type, and vice versa. However, in another embodiment, type designations at bins available for re-allocation (e.g., because of under-utilization) are modified based on the current higher occupancy rates for bins of different designation types. For example, high security bins may be re-allocated as lower security bins and may have security features temporarily disabled.

An analysis may also be performed to estimate a turn-away rate for a given current occupancy rate. In one embodiment, a turn-away rate is the rate at which users will be unable to store medications in PSBs at the dispensing device. Current occupancy rate data may be analyzed in light of past turn-away data to estimate an impact of the occupancy rate. The turn-away data may be collected for each type of PSB, or may be collected generally across all PSBs. The turn-away data may be used to set the threshold levels triggering messaging or re-allocation. The timing and selection of bins for re-allocation may, therefore, be based at least in part on the turn-away rate.

In addition to real-time monitoring, bin occupancy may be monitored over time (e.g., by the central server computer system) to evaluate past occupancy rates for PSBs and ISBs at a dispensing device 120. This past occupancy rate data may then be stored in data stores 110 and/or the dispensing device 120. The past occupancy rate data may be used to compute average occupancy rates at PSBs. This average occupancy rate data may reflect occupancy rates for different bin types. Also, average past occupancy rates may be calculated over one or more previous time periods, and may illustrate a seasonally adjusted average, an average at certain times of the day or week, a cabinet-specific average, a facility-wide average, or an otherwise calculated average occupancy rate.

The past occupancy rates may be analyzed to determine a variance in occupancy rates for the PSBs. This variance may be a variance in the average occupancy rate, a day-to-day variance, seasonal variance, a variance within periods, or other measures of variance. The average past occupancy rates and the variance measures may be used separately or in combination to determine when and how bins are to be re-allocated at a dispensing device.

This past occupancy rate data may also include data indicating the rate of turn-aways (e.g., according to bin type or for a cabinet as a whole) associated with different occupancy rates. It may also assess the effect of the turn-aways (e.g., issues related to being redirected to another cabinet, time delays in reallocating bins at the dispensing device, etc.). This range of past occupancy rate data may be structured to allow queries regarding the past allocations of PSBs and ISBs at the dispensing device 120.

In one embodiment, PSBs or ISBs may be re-allocated (or the re-allocation advised) based on the past occupancy rate data. For example, the current bin allocation may be evaluated in light of past occupancy rates. This may be achieved by correlating the current bin allocation with past occupancy rates, perhaps adjusted to account for differences in the number of patients served, characteristics of those patients, and the number of available bins. Those skilled in the art will recognize that past occupancy rates may be expressed in a number of ways (e.g., as the ratio of PSBs used per patient).

An automatic re-allocation or re-allocation message is triggered, in one embodiment, when these past PSB occupancy rates exceed a threshold. The threshold may be different for different types of bins. Thus, while the re-allocation based on past occupancy rates may be performed for PSBs generally, it may also be directed to certain types of PSBs. By way of example, past occupancy rates may be used to identify historically under-utilized ISBs, and re-allocate them as PSBs.

In addition to current and past occupancy rate data, future patient or medication information may also be used in the re-allocation (or suggested re-allocation) of PSBs or ISBs. Information may be analyzed about new, transferred, or existing patients scheduled to occupy rooms served by a dispensing device 120. Information on their known medication orders may be analyzed to determine storage needs (e.g., analyzing medications from the medication order that will be active during the future period). In addition, medications and/or storage needs may be estimated for such patients given their medical conditions. Future occupancy rates may be determined based on information gathered for scheduled patients.

In addition, estimates may be made of medications and storage needs of future unscheduled patients to be served from the dispensing device. For example, such estimates may be based on typical needs for the average or estimated number of unscheduled patients to be served from the device. Future occupancy rates may be determined based on these estimates for unscheduled patients.

As set forth above for past and current occupancy rate data, PSBs or ISBs may be re-allocated based on the future occupancy rate data, as well. For example, the current bin allocation may be evaluated in light of future occupancy rates. An automatic re-allocation is triggered, in one embodiment, when these future PSB occupancy rates exceed a threshold (which may be different for different types of bins).

The re-allocations and suggested re-allocations described herein may be made immediately without application of any time restraints. However, in one embodiment the re-allocation is scheduled or advised to occur at a future time (e.g., scheduled to occur for an dispensing device of an ER over a busy weekend). In another embodiment, a re-allocation is scheduled to recur at a number of future times.

In many instances set forth above, ISBs are re-allocated as PSBs. However, it is worth noting that the principles outlined above may be applied in the reverse direction, as well. For example, when occupancy rates attributed to a current bin allocation indicate that PSBs are under-utilized while ISBs are over-utilized, PSBs may be re-allocated as ISBs.

Figure 44:
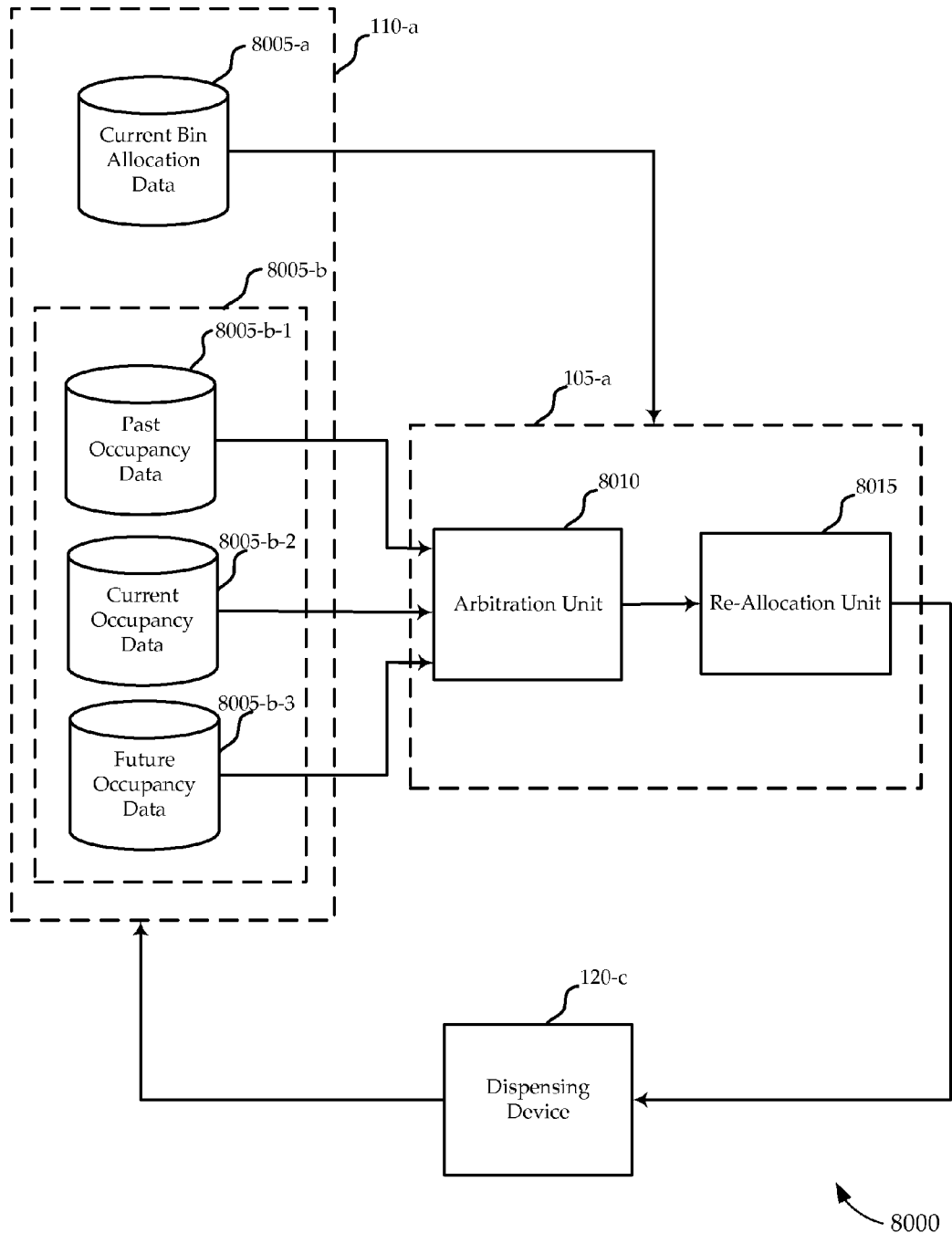
FIG. 44 is a block diagram illustrating a system for re-allocating bins according to various embodiments of the invention.

Turning to FIG. 44, a block diagram illustrates an example implementation of a system 8000 configured to re-allocate bins. In one embodiment, the functional components are integrated with data stores 110-a and the central computer system 105-a of FIG. 1.

Data stores 110-a include a data store 8005-a holding current bin configuration data for a dispensing device 120-c or set of devices. Data stores 110-a also include a data store 8005-b holding the occupancy rate data for a dispensing device 120-c or set of devices. The data store 8005-b that is storing the occupancy rate data includes data stores for past occupancy rate data 8005-b-1, current occupancy rate data 8005-b-2, and future occupancy rate data 8005-b-3. Data stores 110-a may receive bin configuration data and occupancy data from dispensing device 120-c.

Data stores 110-a are in communication with a central server computer system 105-a. The occupancy data (e.g., for a particular dispensing device 120 or bin type therein) from data store 8005-b may be transmitted to or accessed from the central server computer system 105. An arbitration unit 8010 within the central server computer system 105 may process the received occupancy data, attributing different weights to past, current, or future occupancy data. Certain aspects of the data may be filtered out, while other aspects may be weighted more heavily.

The occupancy data, after being processed by the arbitration unit 8010, may be forwarded to a re-allocation unit 8015 within the central server computer system 105. The bin configuration data (e.g., for a particular dispensing device 120 or bin type therein) from data store 8005-a may be transmitted to or accessed from the central server computer system 105. The re-allocation unit 8015 may use the received bin configuration data, in conjunction with the weighted occupancy rate data, to determine the timing and identify the bins for re-allocation.

Although the current bin configuration data store 8005-a, past occupancy rate data store 8005-b-1, current occupancy rate data store 8005-b-2, and future occupancy rate data store 8005-b-3 are shown as components of data store 110-a, in other embodiments any subset of this data may be stored locally at a dispensing device 120, or elsewhere. Similarly, although arbitration unit 8010 and re-allocation unit 8015 are shown as components of central server computer system 105, in other embodiments any subset of this functionality may be performed locally at a dispensing device 120, or elsewhere. Thus, data storage and processing functions may flow through the systems.

Figure 45:
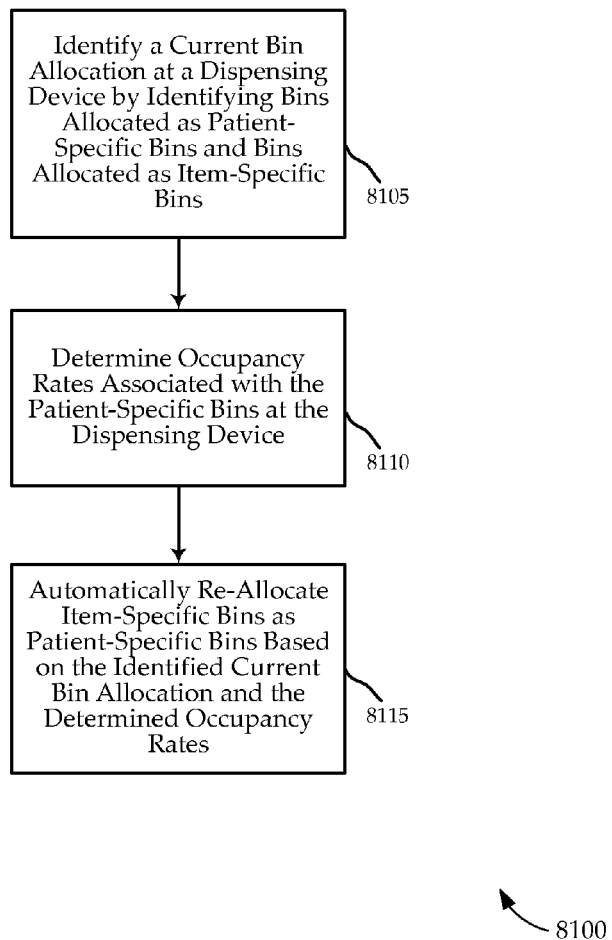
FIG. 45 is a flow diagram illustrating a method of allocating bins at a dispensing device according to various embodiments of the invention.

Referring next to FIG. 45, one embodiment of a method 8100 of allocating bins at a dispensing device is illustrated. This method 8100 may, for example, be performed in whole or in part by the central server computer system 105 or the computer of dispensing device 120 or 220 of FIG. 1A, 1B, or 2. Also, it is worth noting that in this and in other embodiments, various steps may be excluded, and the order may be rearranged.

At block 8105, a current bin allocation is identified for a dispensing device by identifying bins allocated as PSBs and bins allocated as ISBs. At block 8110, occupancy rates associated with the PSBs at the dispensing device are determined. At block 8115, item-specific bins are automatically re-allocated as PSBs based on the identified current bin allocation and the determined occupancy rates.

Figure 46:
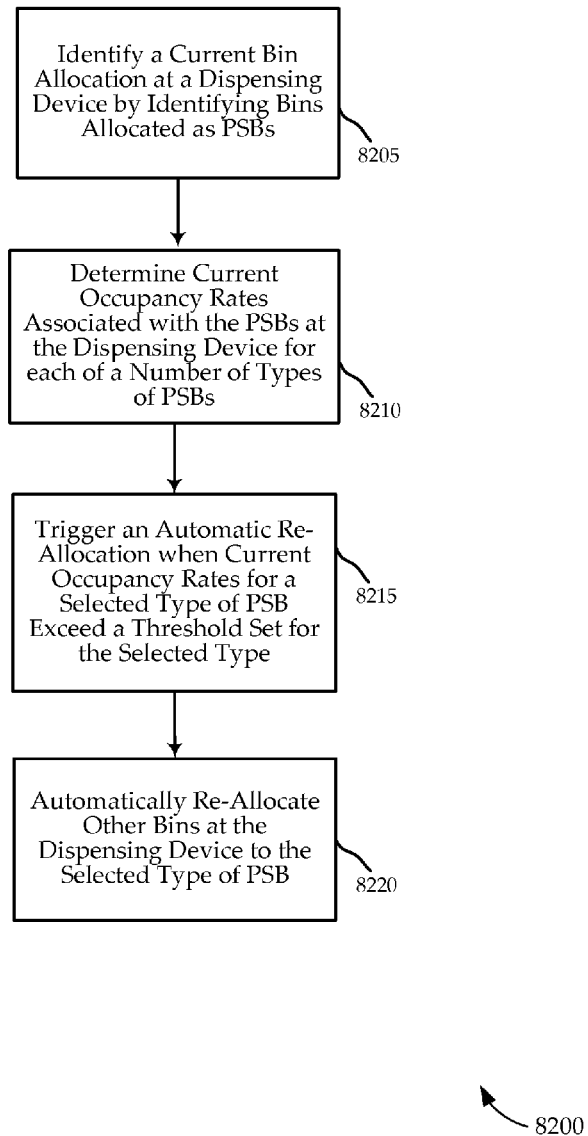
FIG. 46 is a flow diagram illustrating a method of allocating bins at a dispensing device based on current occupancy rates according to various embodiments of the invention.

Referring next to FIG. 46, an example of a method 8200 of allocating bins at a dispensing device based on current occupancy rates is illustrated. This method 8200 may, for example, be performed by the central server computer system 105, a computer of dispensing device 120 or 220, or any combination thereof. This method 8200 may be an embodiment of the method 8100 performed with respect to FIG. 45.

At block 8205, current bin allocation is identified for a dispensing device by identifying bins allocated as PSBs. At block 8210, current occupancy rates associated with the PSBs at the dispensing device are determined for each of a number of types of PSBs. At block 8215, an automatic re-allocation is triggered when current occupancy rates for a selected type of PSB exceed a threshold set for the selected type. The threshold occupancy levels may vary for different types of PSBs.

At block 8220, other bins at the dispensing device are automatically re-allocated as the selected type of PSB. This re-allocation may be from non-PSBs of the selected type designation (i.e., they may be bins of the same type). This re-allocation may, but need not, be targeted at bin types (PSBs or non-PSBs) that have low occupancy rates. In one embodiment, certain bin types may be changed when bins of a given type have relatively high or low occupancy rates (e.g., bins with high security options may store low security items).

Figure 47:
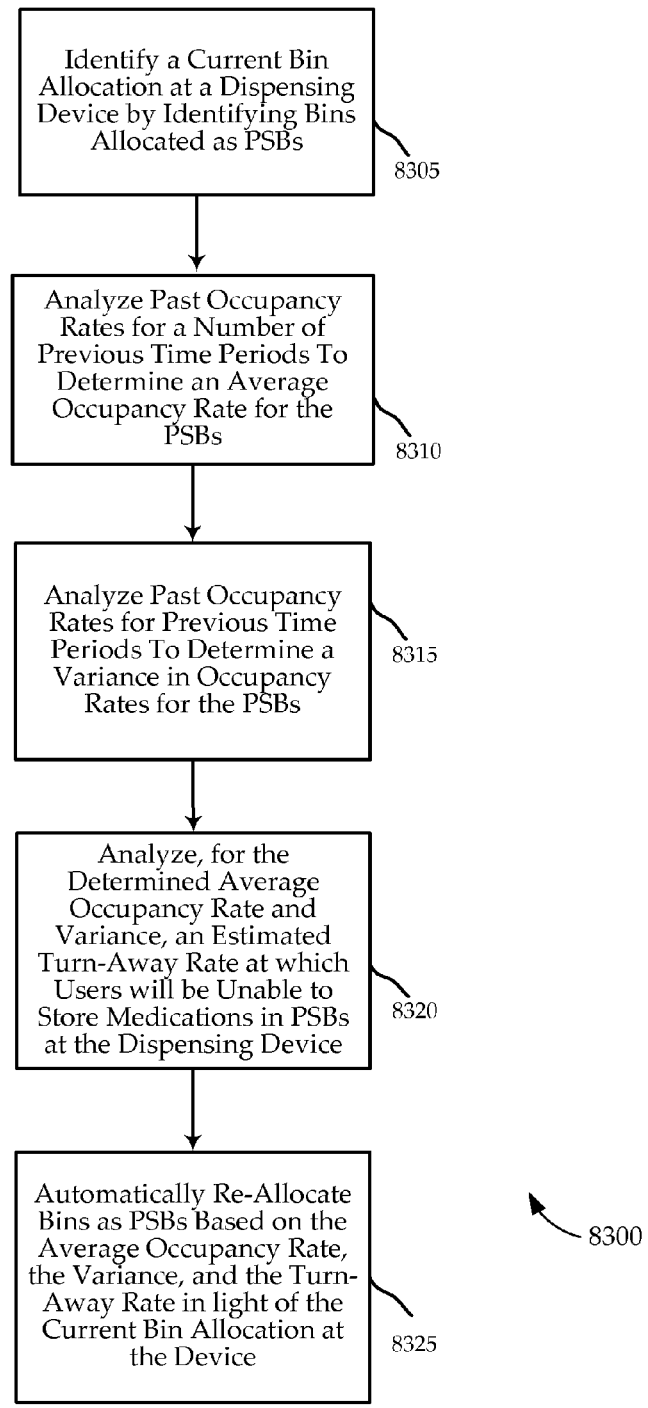
FIG. 47 is a flow diagram illustrating a method of allocating bins at a dispensing device based on past occupancy rates according to various embodiments of the invention.

Referring next to FIG. 47, an example of a method 8300 of allocating bins at a dispensing device based on past occupancy rates is illustrated. This method 8300 may, for example, be performed by the central server computer system 105, a computer of dispensing device 120 or 220, or any combination thereof. This method 8300 may be an embodiment of the method 8100 performed with respect to FIG. 45.

At block 8305, a current bin allocation is identified for a dispensing device by identifying bins allocated as PSBs. At block 8310, past occupancy rates are analyzed for a number of previous time periods to determine an average occupancy rate for the PSBs (e.g., as applied to the current bin configuration). At block 8315, past occupancy rates are analyzed for previous time periods to determine a variance in occupancy rates for the PSBs. This variance may be a variance in the average occupancy rate, a day-to-day variance, seasonal variance, a variance within periods, or other measures of variance.

At block 8320, an estimated turn-away rate at which users will be unable to store medications in PSBs at the dispensing device is analyzed. In one embodiment, the turn-away rate estimate is based on the average occupancy rate and variance. At block 8325, bins are automatically re-allocated as PSBs based on the average occupancy rate, the variance, and the turn-away rate in light of the current bin allocation at the device. In other embodiments, the weights of each factor may be varied depending on cabinet, bin, or patient characteristics. Moreover, note that only a subset of these factors are used in some embodiments.

Figure 48:
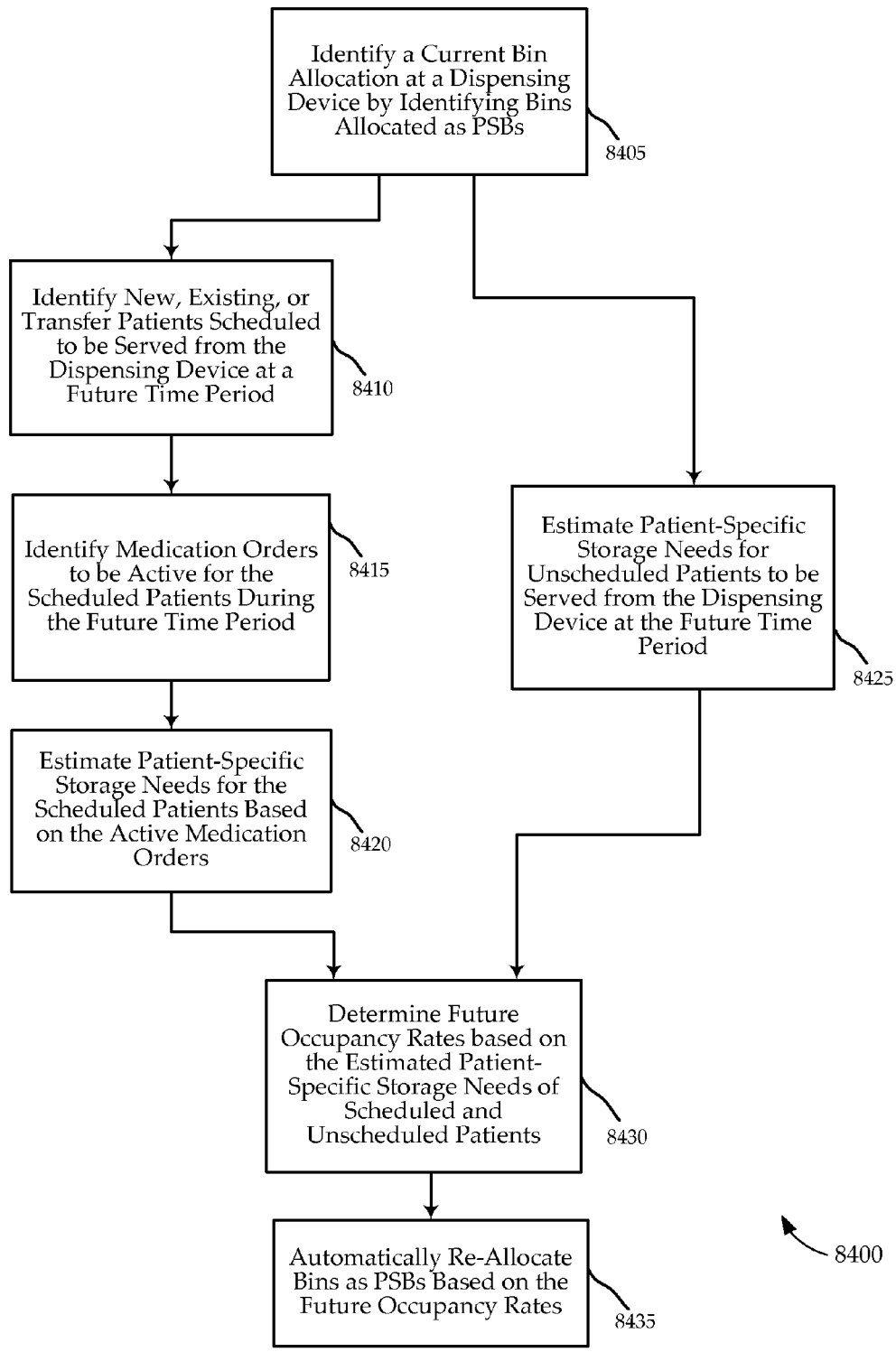
FIG. 48 is a flow diagram illustrating a method of allocating bins at a dispensing device based on future occupancy rates according to various embodiments of the invention.

Turning to FIG. 48, an example of a method 8400 of allocating bins at a dispensing device based on future occupancy rates is illustrated. This method 8400 may, for example, be performed by the central server computer system 105, a computer of dispensing device 120 or 220, or any combination thereof. This method 8400 may be an embodiment of the method 8100 performed with respect to FIG. 45.

At block 8405, a current bin allocation is identified for a dispensing device 120 by identifying bins allocated as PSBs. At block 8410, new, existing, and/or transfer patients are identified who are scheduled to be served from the dispensing device at a future time period. At block 8415, medication orders set to be active for the scheduled patients during the future time period are identified. At block 8420, patient-specific storage needs are estimated for the scheduled patients based on the active medication orders. Additional patient-specific storage needs for the scheduled patients may be estimated (e.g., based on typical needs for patients similar to the scheduled patients).

At block 8425, patient-specific storage needs are estimated for unscheduled patients likely be served from the dispensing device at the future time period (e.g., based on typical needs for the average or estimated number of unscheduled patients likely to be served from the device). At block 8430, future occupancy rates are estimated for the PSBs at the dispensing device based on the estimated patient-specific storage needs of scheduled and unscheduled patients. At block 8435, bins are automatically re-allocated as PSBs based on the future occupancy rates.

Figure 49:
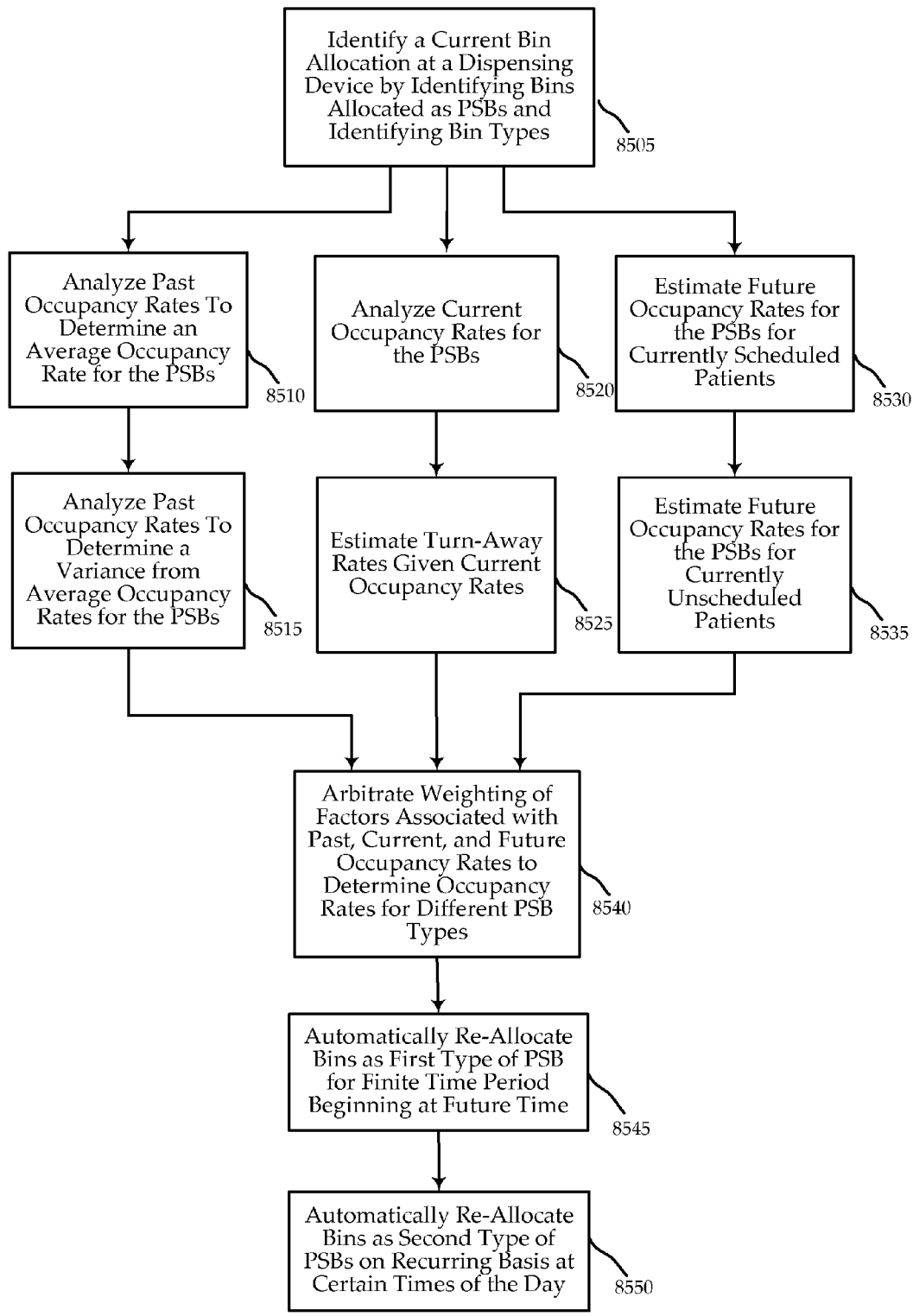
FIG. 49 is a flow diagram illustrating a method of allocating bins at a dispensing device based on a combination of past, current, or future occupancy rates according to various embodiments of the invention.

Turning to FIG. 49, an example of a method 8500 of allocating bins at a dispensing device based a combination of past, current, or future occupancy rates is illustrated. This method 8500 may, for example, be performed by the central server computer system 105, a computer of dispensing device 120 or 220, or any combination thereof. This method 8500 may be an embodiment of the method 8100 performed with respect to FIG. 45.

At block 8505, a current bin allocation is identified for a dispensing device by identifying bins allocated as PSBs and identifying bin types. This method 8500 may then make use of any subset or weighted combination of past, current, and/or future occupancy rates for PSBs of the device.

At block 8510, past occupancy rates are analyzed to determine an average occupancy rate for the PSBs. This may be an average over a time period, a seasonally adjusted average, an average at certain times of the day or week, a cabinet-specific average, a facility-wide average, or an otherwise calculated average occupancy rate. At block 8515, past occupancy rates are analyzed to determine a variance from average occupancy rates for the PSBs.

At block 8520, current occupancy rates are analyzed for the PSBs. This may be on a real-time query, or on recent polling data. At block 8525, turn-away rates for the PSBs are estimated in light of the current occupancy rates. The turn-away rate is a rate in which a user trying to store items in a PSB will be unable to store medications in PSBs at the dispensing device.

At block 8530, future occupancy rates are estimated for the PSBs for patients currently scheduled to be served from the device during a future time period. At block 8535, future occupancy rates are estimated for the PSBs based on storage needs of an estimate of patients to be served from the device during a future time period, yet who are not currently on the schedule.

At block 8540, factors associated with past, current, and future occupancy rates are used, with different weights, to determine occupancy rates for different PSB types. At block 8545, bins are automatically re-allocated as a first type of PSB for a finite time period beginning at a future time. At block 8550, bins are automatically re-allocated as a second type of PSBs on a recurring basis (e.g., flip-flopping between PSB and ISB allocation at certain times of the day). Any of the automated re-allocation, as described with reference to FIGS. 45-49 may, instead be an automated transmission of a re-allocation message to direct re-allocation to a user, the dispensing device, or the central server computer system.

Figure 50:
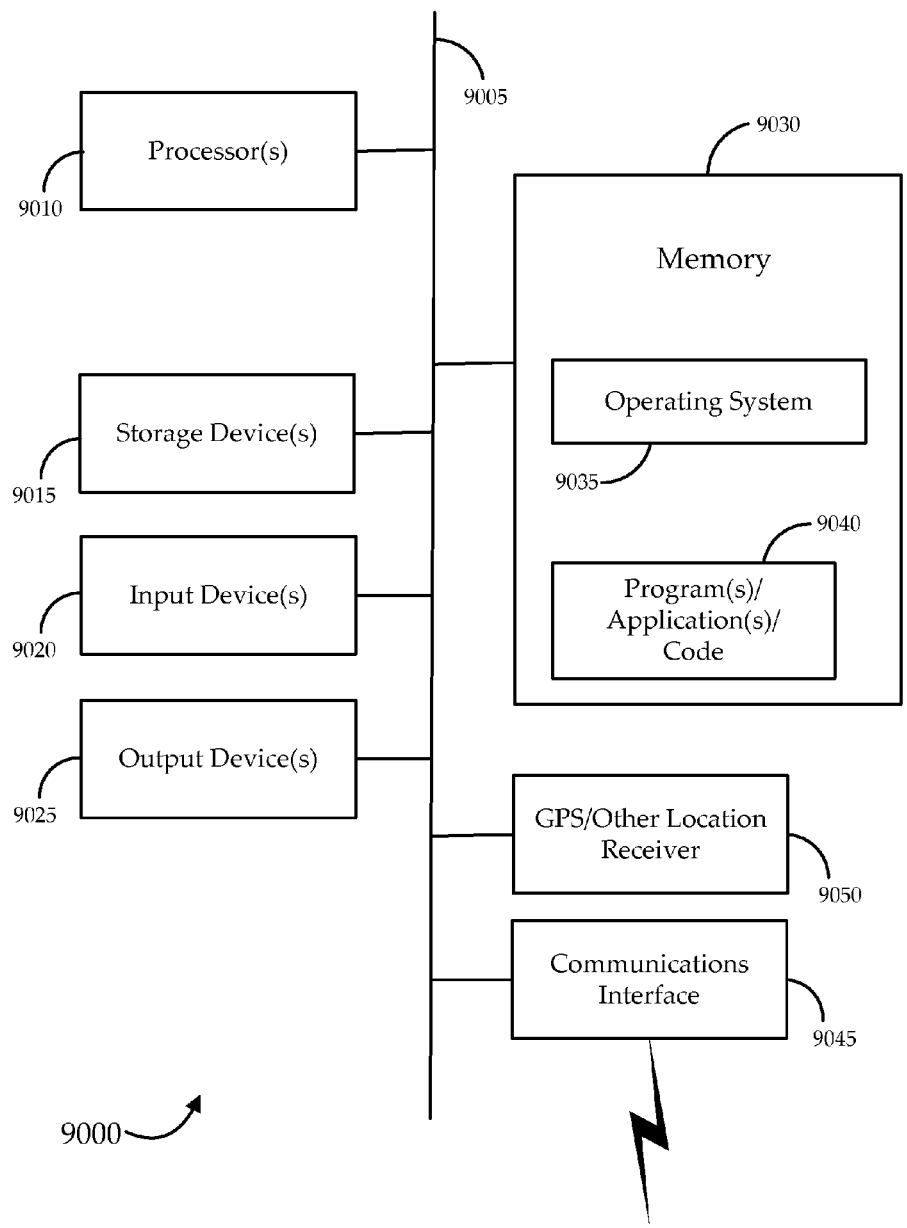
FIG. 50 is a schematic diagram that illustrates a representative device structure that may be used in various embodiments of the present invention.

A device structure 9000 that may be used for a central server computer system 105 of FIG. 1A or 2, the computer of the patient dispensing device 120 or 220 of FIG. 1A, 1B, or 2, the computer of the central dispensing unit 115 of FIG. 1A or 1B, or other computing devices or functional or processing units described herein, is illustrated with the schematic diagram of FIG. 50. This drawing broadly illustrates how individual system elements of each of the aforementioned devices may be implemented, whether in a separated or more integrated manner.

The example structure is shown made up of hardware elements that are electrically coupled via bus 9005, including processor(s) 9010 (which may be, or may include, a DSP or special-purpose processor), storage device(s) 9015, input device(s) 9020, and output device(s) 9025. The storage device (s) 9015 may be a machine-readable storage media reader connected to any machine-readable storage medium, the combination comprehensively representing remote, local, fixed, or removable storage devices or storage media for temporarily or more permanently containing computer-readable information. The communications systems interface 9045 may interface to a wired, wireless, or other type of interfacing connection that permits data to be exchanged with other devices. The communications system(s) 9045 may permit data to be exchanged with a network. There may also be a GPS or other location based receiver 9050, configured to transmit location information about a device that may be leveraged for various purposes.

The structure 9000 may also include additional software elements, shown as being currently located within working memory 9030, including an operating system 9035 and other code 9040, such as programs or applications designed to implement methods of the invention. It will be apparent to those skilled in the art that substantial variations may be used in accordance with specific requirements. For example, customized hardware might also be used, or particular elements might be implemented in hardware, software (including portable software, such as applets), or both. Thus, any functionality described herein may be implemented with one or more Application Specific Integrated Circuits (ASICs) adapted to perform some or all of the applicable functions in hardware. Alternatively, the functions may be performed by one or more other processing units (or cores), on one or more integrated circuits. In other embodiments, other types of integrated circuits may be used (e.g., Structured/Platform ASICs, Field Programmable Gate Arrays (FPGAs) and other Semi-Custom ICs), which may be programmed in any manner known in the art.

It should be noted that the methods, systems and devices discussed above are intended to be interpreted as examples only. It must be stressed that various embodiments may omit, substitute, or add various procedures or components as appropriate. For instance, it should be appreciated that in alternative embodiments, the methods may be performed in an order different than that described, and that various steps may be added, omitted or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known circuits, processes, algorithms, structures, and techniques have been shown without unnecessary detail in order to avoid obscuring the embodiments.

Also, it is noted that the embodiments may be described as a process which is depicted as a flowchart, a flow diagram, a structure diagram, or a block diagram. Although a flowchart may describe the operations as a sequential process, many of the operations can be performed in parallel or concurrently. In addition, the order of the operations may be rearranged. A process is terminated when its operations are completed, but could have additional steps not included in the figure.

Moreover, as disclosed herein, the term "memory" may represent one or more devices for storing data, including read-only memory (ROM), random access memory (RAM), magnetic RAM, core memory, magnetic disk storage mediums, optical storage mediums, flash memory devices or other machine-readable mediums for storing information. The term "machine-readable medium" includes, but is not limited to, portable or fixed storage devices, optical storage devices, wireless channels, a sim card, other smart cards, and various other mediums capable of storing, containing or carrying instructions or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine-readable medium such as a storage medium. Processors may perform the necessary tasks.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be required before the above elements are considered. Accordingly, the above description should not be taken as limiting the scope of the invention.

What is claimed is:

1. A system for determining selected items from a medication order to be reordered, the system comprising:
a dispensing device of a plurality of dispensing devices at a healthcare facility, the dispensing device including:
one or more patient-specific bins assigned for exclusive use to a patient of a plurality of patients; and
one or more item-specific bins each allocated for an item available to be used by the plurality of patients; and
a central server computer system, communicatively coupled to the dispensing device, and configured to:
receive an active medication order for the patient;
receive a future medication order for the patient;
compare the active medication order to a listing of medications stored in the one or more item-specific bins at the dispensing device to determine a subset of items of the active medication order to be stored in the one or more patient-specific bins at the device;
automatically identify, for at least one of the items of the subset, a reorder level triggering reorder of respective items;
determine, for each of the at least one of the items, whether the one or more patient-specific bins for the patient at the device are at or below the identified reorder levels; and
determine, based on the active medication order and the future medication order, a target level for one or more items determined to be at or below the identified reorder levels, the target level identifying a quantity of the one or more items to store in the one or more patient-specific bins.

2. The system of claim 1, wherein the central computer system is further configured to:
receive data from the dispensing device identifying a current level of supply for the subset of items of the active medication order, wherein the received data is used in the determination of whether the patient-specific bins for the patient at the device are at or below the identified reorder levels.

3. The system of claim 1, wherein the central computer system is further configured to:
identify, for each of one or more items determined to be at or below the identified reorder levels at the dispensing device, a reorder amount for the patient at the dispensing device.

4. The system of claim 3, wherein the central computer system is further configured to:
transmit the reorder amount;
modify the reorder amount based at least in part on an updated medication order; and
transmit the modified reorder amount.

5. The system of claim 1, wherein the central computer system is further configured to:
identify, for each of one or more items determined to be at or below the identified reorder levels at the dispensing device, a reorder amount for the patient at the dispensing device by comparing the target level to a current level of supply.

6. The system of claim 1, wherein the central computer system is further configured to:
utilize the active medication order to determine a rate of use by the patient for the at least one of the subset of items, wherein the rate of use is utilized to identify the target level.

7. The system of claim 1, wherein the central computer system is further configured to:
identify a target days supply for the one or more items determined to be at or below the identified reorder levels at the dispensing device, wherein the target days supply is used to identify the target level.

8. The system of claim 1, wherein the central computer system is further configured to:
utilize the active medication order to determine the rate of use by the patient for the at least one of the subset of items, wherein the rate of use is utilized to identify the reorder level.

9. The system of claim 1, wherein the central computer system is further configured to:
modify a reorder level based at least in part on a changed rate of use by the patient for the at least one of the subset of items.

10. The system of claim 1, wherein,
the one or more patient-specific bins are assigned to the patient for temporary use.

11. A method of determining selected items from a medication order to be reordered, the method comprising:
receiving an active medication order for a patient associated with a dispensing device;
receiving a future medication order for the patient;
comparing the active medication order to a listing of medications stored in item-specific bins at the dispensing device to determine a subset of items of the active medication order to be stored in patient-specific bins at the device;
automatically identifying, for at least one of the items of the subset, a reorder level triggering reorder of respective items;
receiving data from the dispensing device identifying a current level of supply for the subset of items of the medication order; and
determining, for each of the at least one of the items, whether the patient-specific bins for the patient at the device are at or below the identified reorder levels, wherein the received data is used in determining whether the patient-specific bins are at or below the identified reorder levels; and
determining, based on the active medication order and the future medication order, a target level for one or more items determined to be at or below the identified reorder levels at the dispensing device, the target level identifying a quantity of the one or more items to store in the patient-specific bins.

12. The method of claim 11, further comprising:
identifying, for each of one or more items determined to be at or below the identified reorder levels at the dispensing device, a reorder amount for the patient at the dispensing device.

13. The method of claim 11, further comprising:
identifying, for each of one or more items determined to be at or below the identified reorder levels at the dispensing device, a reorder amount for the patient at the dispensing device by comparing the target level to a current level of supply.

14. The method of claim 11, further comprising:
utilizing the active medication order to determine a rate of use by the patient for the at least one of the subset of items, wherein the rate of use is utilized to identify the target level.

15. The method of claim 11, further comprising:
identifying a target days supply for the one or more items determined to be at or below the identified reorder levels at the dispensing device, wherein the target days supply is used to identify the target level.

16. The method of claim 11, further comprising:
determining whether supply levels for each of the one or more items for the patient at the dispensing device are above the target level.

17. The method of claim 16, further comprising:
utilizing the active medication order to determine a remaining use for the items above the target level; and
transmitting data directing the removal of at least some of items above the target level based at least in part on the remaining use.

18. The method of claim 11, further comprising:
utilizing the active medication order to determine the rate of use by the patient for the at least one of the subset of items, wherein the rate of use is utilized to identify the reorder level.

19. The method of claim 11, further comprising:
modifying a reorder level based at least in part on a changed rate of use by the patient for the at least one of the subset of items.

20. The method of claim 11, further comprising:
identifying a minimum days supply for each of the at least one of the items of the subset to identify the reorder level.

21. A device for determining a reorder amount, the device comprising:
a receiving unit configured to receive an active medication order for a patient associated with a dispensing device and to receive a future medication order for the patient;
a processing unit, communicatively coupled with the receiving unit, and configured to:
compare the active medication order to a listing of medications stored in item-specific bins at the dispensing device to determine a subset of items of the active medication order to be stored in patient-specific bins at the device;
automatically identify, for at least one of the items of the subset, a reorder level triggering reorder of respective items;
receive data identifying a current level of supply for the subset of items of the medication order;
determine, for each of the at least one of the items, whether the patient-specific bins for the patient at the device are at or below the identified reorder levels;
determine, based on the active medication order and the future medication order, a target level for each of one or more items determined to be at or below the identified reorder levels at the dispensing device, the target level identifying a quantity of the one or more items to store in the patient-specific bins;
identify, based on the current level of supply and the target levels, a reorder amount for each of the one or more items determined to be at or below the identified reorder levels; and
a transmitting unit, communicatively coupled with the processing unit, and configured to transmit data specifying the reorder amount.

* * * * *